United States Patent [19]

Meyer

[11] Patent Number: 5,089,400
[45] Date of Patent: Feb. 18, 1992

[54] POLYPEPTIDES AND PROCESS FOR THE PRODUCTION THEREOF

[75] Inventor: François Meyer, Zurich, Switzerland

[73] Assignee: Ciba-Geigy Corporation, Ardsley, N.Y.

[21] Appl. No.: 320,185

[22] Filed: Mar. 7, 1989

Related U.S. Application Data

[60] Division of Ser. No. 787,892, Oct. 16, 1985, abandoned, and a continuation-in-part of Ser. No. 422,112, Sep. 23, 1982, abandoned.

[30] Foreign Application Priority Data

| Oct. 3, 1981 | [GB] | United Kingdom | 8129937 |
| Mar. 26, 1982 | [GB] | United Kingdom | 8208988 |
| Sep. 1, 1982 | [GB] | United Kingdom | 8224871 |

[51] Int. Cl.⁵ .................. C12P 21/02; C12N 15/00; C12N 15/20; C12N 15/21; C12N 15/70
[52] U.S. Cl. .................. 435/69.51; 435/91; 435/172.3; 435/240.1; 435/252.3; 435/252.33; 435/320.1; 536/27; 935/11
[58] Field of Search .......... 435/252.3, 252.31–252.35, 435/240.1, 240.2, 91, 172.1, 172.3, 69.51, 811, 320.1, 254, 255, 256; 536/27; 530/351; 935/11, 70-75

[56] References Cited

FOREIGN PATENT DOCUMENTS 0041313 12/1981 European Pat. Off. ......... 435/172.3
0051873 5/1982 European Pat. Off. ......... 435/172.3

OTHER PUBLICATIONS

Maniatis et al; Cell 15: 687 (1978).
M. Streuli et al., Proc. Natl. Acad. Sci. U.S.A. 78, 2848–2852 (1981).
M. D. Edge et al., Nature 292, 756–761 (1981).

*Primary Examiner*—James Martinell
*Attorney, Agent, or Firm*—JoAnn Villamizar

[57] ABSTRACT

Recombinant DNA molecules and hosts transformed with them are described which produce polypeptides displaying a human lymphoblastoid interferon activity. There are also provided processes for the preparation of said recombinant DNA molecules, said hosts, and said lymphoblastoid interferon-like polypeptides. The polypeptides of the invention are useful as immunomodulators, especially as antiviral, antitumor and anticancer agents.

27 Claims, 13 Drawing Sheets

```
  1
MET ALA LEU SER PHE SER LEU LEU MET ALA VAL LEU VAL LEU SER TYR LYS SER ILE CYS SER LEU GLY
ACATCCCA ATG GCC CTG TCC TTT TCT TTA CTG ATG GCC GTG CTG GTG CTC AGC TAC AAA TCC ATC TGT TCT CTG GGC 69

CYS ASP LEU PRO GLN THR HIS SER LEU GLY ASN ARG ARG ALA LEU ILE LEU LEU ALA GLN MET GLY ARG ILE PRO
TGT GAT CTG CCT CAG ACC CAC AGC CTG GGT AAT AGG AGG GCC TTG ATA CTC CTG GCA CAA ATG GGA AGA ATC CCC 144

PRO PHE SER CYS LEU LYS ASP ARG HIS ASP PHE GLY PHE PRO GLN GLU GLU PHE ASP GLY ASN GLN PHE GLN LYS
CCT TTC TCC TGC CTG AAG GAC AGA CAT GAC TTT GGA TTT CCC CAG GAG GAG TTT GAT GGC AAC CAG TTC CAG AAG 219

ALA GLN ALA ILE SER VAL LEU HIS GLU MET ILE GLN GLN THR PHE ASN LEU PHE SER THR LYS ASP SER SER ALA
GCT CAA GCC ATC TCT GTC CTC CAT GAG ATG ATC CAG CAG ACA TTC AAT CTC TTC AGC ACA AAG GAC TCA TCT GCT 294

THR TRP GLU GLN SER LEU LEU GLU LYS PHE SER THR GLU LEU ASN GLN GLN LEU ASN ASP LEU GLU ALA CYS VAL
ACT TGG GAA CAG AGC CTC CTA GAA AAA TTT TCC ACT GAA CTT AAC CAG CAG CTG AAT GAC CTG GAA GCC TGC GTG 369

ILE GLN GLU VAL GLY VAL GLU GLU THR PRO LEU MET ASN VAL ASP SER ILE LEU ALA VAL LYS LYS TYR PHE GLN
ATA CAG GAG GTT GGG GTG GAA GAG ACT CCC CTG ATG AAT GTG GAC TCC ATC CTG GCT GTG AAG AAA TAC TTC CAA 444

ARG ILE THR LEU TYR LEU THR GLU LYS LYS TYR SER PRO CYS ALA TRP GLU VAL VAL ARG ALA GLU ILE MET ARG
AGA ATC ACT CTT TAT CTG ACA GAG AAG AAA TAC AGC CCT TGT GCC TGG GAG GTT GTC AGA GCA GAA ATC ATG AGA 519

SER PHE SER LEU SER LYS ILE PHE GLN GLU ARG LEU ARG ARG LYS GLU
TCC TTC TCT TTA TCA AAA ATT TTT CAA GAA AGA TTA AGG AGG AAG GAA TGA AACCTGTTCAACATGGAAATGATCTGTATT 601

GACTAATACACCAGTCCACACTTCTGATGACTTCTGCCATTTCTGAGTTCTCCTATAACCACCGCATGAGTTGAATCAAAATTTCAGATCTTT 700

TCAGGAGTGTAAGGAAACATGATGTTACCTGTGCAGGCACTAGTCCTTTACAGATGACCATGCTGATGTGTATATCAAAATATCAAAATATTA 799

TTTATTTATTAGATTTAAATTATTTTGTCCATGTAATATATATGTACTTTTACATTGTGTATATCAAAATATCAAAATATGTATTATTATTAGTCAATATAT 898

TATTTTCTTTTATTAATTTTACTATTATTAAAAACTTCTTATATTATTGTTATTG
```

FIG. 4

```
                                        SER SER ASN PHE GLN CYS GLN LYS LEU LEU TRP GLN LEU ASN
                                        AGC AGC AAT TTT CAG TGT CAG AAG CTC CTG TGG CAA TTG AAT    138

GLY ARG LEU GLU TYR CYS LEU LYS ASP ARG MET ASN PHE ASP ILE PRO GLU ILE LYS GLN LEU GLN GLN PHE
GGG AGG CTT GAA TAC TGC CTC AAG GAC AGG ATG AAC TTT GAC ATC CCT GAG ATT AAG CAG CTG CAG CAG TTC    213

GLN LYS GLU ASP ALA ALA LEU THR ILE TYR GLU MET LEU GLN ASN ILE PHE ALA ILE PHE ARG GLN ASP SER SER
CAG AAG GAG GAC GCC GCA TTG ACC ATC TAT GAG ATG CTC CAG AAC ATC TTT GCT ATT TTC AGA CAA GAT TCA TCT    288

SER THR GLY TRP ASN GLU THR ILE VAL GLU ASN LEU LEU ALA ASN VAL TYR HIS GLN ILE ASN HIS LEU LYS THR
AGC ACT GGC TGG AAT GAG ACT ATT GTT GAA AAC CTC CTG GCT AAT GTC TAT CAT CAG ATA AAC CAT CTG AAG ACA    363

VAL LEU GLU GLU LYS LEU GLU LYS GLU ASP PHE THR ARG GLY LYS LEU MET SER SER LEU HIS LEU LYS ARG TYR
GTC CTG GAA GAA AAA CTG GAG AAA GAA GAT TTC ACC AGG GGA AAA CTC ATG AGC AGT CTG CAC CTG AAA AGA TAT    438

TYR GLY ARG ILE LEU HIS TYR LEU LYS ALA LYS GLU TYR SER HIS CYS ALA TRP THR ILE VAL ARG VAL GLU ILE
TAT GGG AGG ATT CTG CAT TAC CTG AAG GCC AAG GAG TAC AGT CAC TGT GCC TGG ACC ATA GTC AGA GTG GAA ATC    513

LEU ARG ASN PHE TYR PHE ILE ASN ARG LEU THR GLY TYR LEU ARG ASN
CTA AGG AAC TTT TAC TTC ATT AAC AGA CTT ACA GGT TAC CTC CGA AAC TGAAGATCTCCTAGCCTGTGCCTCTGGGACTGGAC    596

AATTGCTTCAAGCATTCTTCAACCAGCAGATGCTGTTAAGTGACTGATGGCTAATGTACTGCATATGAAAGGACACTAGAAGATTTGAAATTTTTAT    695

TAAATTATGAGTTATTTTATTTATTTAAATTTATTTTGGAAAATAAATTATTTTGGTGCAAAAGTC
```

FIG. 5

```
                                                                SER SER ALA
                                                                TCA TCT GCT  294
ALA TRP ASP GLU THR LEU LEU ASP LYS PHE TYR THR GLU LEU TYR GLN GLN LEU ASN ASP LEU GLU ALA CYS VAL
GCT TGG GAT GAG ACC CTC CTA GAC AAA TTC TAC ACT GAA CTC TAC CAG CAG CTG AAT GAC CTG GAA GCC TGT GTG  369

ILE GLN GLY VAL GLY THR GLU THR PRO LEU MET LYS GLU ASP SER ILE LEU ALA VAL ARG LYS TYR PHE GLN
ATA CAG GGG GTG GGG GTG ACA GAG ACT CCC CTG ATG AAG GAG GAC TCC ATT CTG GCT GTG AGG AAA TAC TTC CAA  444

ARG ILE THR LEU LEU LYS TYR SER PRO CYS ALA TRP GLU VAL VAL ARG ALA GLU ILE MET ARG
AGA ATC ACT CTC TAT CTG AAA GAG AAG TAC AGC CCT TGT GCC TGG GAG GTT GTC AGA GCA GAA ATC ATG AGA  519

SER PHE SER LEU SER THR ASN LEU GLN GLU SER LEU ARG SER LYS GLU
TCT TTT TCT TTG TCA ACA AAC TTG CAA GAA AGT AAG GAA TGA AAACTGGTTCAACATGGAAATGATTTTCATT  601

GATTCGTATGCCAGCTCACCTTTTTATGATCTGCCATTTCAAAGACTCATGTTTCTGCTATGACCATGACACGATTTAAATCTTTTCAAATGTTTTAG  700

GAGTATTAATCAACATTGTATTCAGCTCTTAAGGCACTAGTCCCTTACAGAGGACCATGTCCTGACTGATCATTATCTATTTAAATATTTTAAAATATT  799

ATTTATTTAACTATTTTATAAAACAACTTATTTTGTTCATATTATGTCATGTGCACCTTTGCACAGTGGTTAATGTAATAAAATGTTCTTTGTATTT  898

GGTATATTTATTTGTGTTCATTGAACTTTTGCTATGGAACTTTTGTACTTGTTATTCTTTAAAATGAAATTCCAAGCCTAATTGTGCAACCTGA  997

TTACAGAATAACTGGTACACTTCATTTATCCATCAATATTATATTCAAGATATAAGTAAAAATAAACTTTCTGTAAACCAGTTG
```

```
                                                              CCCAAGGTTCAGAGTCACCCATCTCAGCAAGCCCAGAAGCATCTGCAAT
  1
    MET ALA SER PRO PHE ALA LEU LEU MET |ALA| LEU VAL VAL LEU SER CYS LYS SER SER CYS SER LEU GLY
    ATCTATG ATG GCC TCG CCC TTT GCT GCT TTA CTG ATG  GCC  CTG GTG GTG CTC AGC TGC AAG TCA AGC TGC TCT CTG GGC  69

CYS ASP LEU PRO GLU THR HIS SER ASP ASN ARG ARG THR LEU MET LEU ALA GLN MET SER ARG ILE SER
    TGT GAT CTC CCT GAG ACC CAC AGC CTG GAT AAC AGG AGG ACC TTG ATG CTG GCA CAA ATG AGC AGA ATC TCT  144

PRO SER SER CYS LEU MET ASP ARG HIS ASP PHE PRO GLY PHE PRO GLN GLU PHE ASP GLY ASN GLN PHE GLN LYS
    CCT TCC TCC TGT CTG ATG GAC AGA CAT GAC TTT CCC GGA TTT CCC CAG GAG GAG TTT GAT GGC AAC CAG TTC CAG AAG  219

ALA PRO ALA ILE SER VAL LEU HIS GLU LEU HIS GLN ILE PHE ASN LEU PHE THR THR LYS ASP SER SER ALA
    GCT CCA GCC ATC TCT GTC CTC CAT GAG CTG CAT CAG ATC TTC AAC CTC TTT ACC ACA AAA GAT TCA TCT GCT  294

ALA TRP ASP GLU ASP LEU LEU ASP LYS PHE CYS THR PRO LEU GLN LYS TYR GLN GLN LEU ASN ASP LEU GLU ALA CYS VAL
    GCT TGG GAT GAG GAC CTC CTA GAC AAA TTC TGC ACC CCT CTG CAA AAG TAC CAG CAG CTC AAT GAC CTG GAA GCC TGT GTG  369

MET GLN GLU GLU ARG VAL GLY GLU THR PRO LEU MET ASN |ALA| ASP SER ILE LEU ALA VAL LYS LYS TYR PHE ARG
    ATG CAG GAG GAG AGG GTG GGA GAA ACT CCC CTG ATG AAT  GCG  GAC TCC ATC TTG GCT GTG AAG AAA TAC TTC CGA  444

ARG ILE THR LEU TYR LEU THR GLU LYS LYS TYR SER PRO CYS ALA TRP GLU VAL VAL ARG ALA GLU ILE MET ARG
    AGA ATC ACT CTC TAT CTG ACA GAG AAG AAA TAC AGC CCT TGT GCC TGG GAG GTT GTC AGA GCA GAA ATC ATG AGA  519

SER LEU SER LEU THR ASN LEU GLN GLU ARG LEU ARG ARG LYS GLU
    TCC CTC TCT TTA TCA ACA AAC TTG CAA GAA AGA TTA AGG AGG AAG GAA TAA CACCTGGTCTCCAACATGAAACAATTCTTATTG  601

ACTCATATACCAGGTCACGCTTTCATGAATTCTGCCATTTCAAAGACTCTCACTTCTGCTATAACTATGACCATGCTGATAAACTGATTTATCTATTTA  700

AATATTTATTTAGCTATTCATAAGATTTAAATTATTTTGTTCATATAACATCTTTACACTGTGCATCTTTACACTGTGGTTAGTGTAATAAAACATGTTCCTTA  799

TATTTACTCAAATTCATTATTTA
```

ATCTGAACCAGCTCAGCAGCATCCACAAC

```
      MET ALA LEU THR PHE TYR LEU LEU VAL ALA LEU VAL VAL LEU SER TYR LYS SER PHE SER LEU GLY
  1   ATCTACA ATG GCC TTG ACT TTT TAT TTA CTG GTG GCC CTA GTG GTG CTC AGC TAC AAG TCA TTC AGC TCT GGC  69

CYS ASP LEU PRO GLN THR HIS SER LEU GLY ASN ARG ARG ALA LEU LEU ILE LEU ALA GLN MET ARG ARG ILE SER
      TGT GAT CTG CCT CAG ACT CAC AGC CTG GGT AAC AGG AGG GCC TTG ATA CTC CTG GCA CAA ATG CGA AGA ATC TCT  144

PRO PHE SER CYS LEU LYS ASP HIS ASP ARG PHE PRO GLN GLU PHE ASP LYS GLN PHE GLN LYS
      CCT TTC TCC TGC CTG AAG GAC CAT GAC AGA TTC CCC CAG GAG TTT GAT GAT AAA CAG TTC CAG AAG  219

ALA GLN ALA ILE SER VAL LEU HIS GLU MET ILE GLN THR PHE ASN LEU PHE SER THR LYS ASP SER SER ALA
      GCT CAA GCC ATC TCT GTC CTC CAT GAG ATG ATC CAG ACC TTC AAC CTC TTC AGC ACA AAG GAC TCA TCT GCT  294

ALA LEU ASP GLU THR LEU LEU ASP GLU PHE TYR ILE GLU LEU ASP GLN GLN LEU ASN ASP LEU GLU SER CYS VAL
      GCT TTG GAT GAG ACC CTT CTA GAT GAA TTC TAC ATC GAA CTT GAC CAG CAG CTG AAT GAC CTG GAG TCC TGT GTG  369

MET GLN GLU VAL GLY VAL ILE GLU VAL SER PRO LEU MET TYR GLU ASP SER ILE LEU ALA VAL ARG LYS TYR PHE GLN
      ATG CAG GAA GTG GGG GTG ATA GAG TCT CCC CTG ATG TAC GAG GAC TCC ATC CTG GCT GTG AGG AAG TAC TTC CAA  444

ARG ILE THR LEU TYR LEU THR GLU LYS LYS TYR SER SER CYS ALA TRP GLU VAL VAL ARG ALA GLU ILE MET ARG
      AGA ATC ACT CTA TAT CTG ACA GAG AAG AAA TAC AGC AGC TGT GCC TGG GAG GTT GTC AGA GCA GAA ATC ATG AGA  519

SER PHE SER LEU SER ILE ASN LEU GLN LYS ARG LEU LYS SER LYS GLU
      TCC TTC TCT TTA TCA ATC AAC TTG CAA AAA AGA TTG AAG AGT AAG GAA TGA GACTTGGTACAACACGGAAATGATTCTTATA  601

GACTAATACAGAGCTCACACTTCGACAAGTTGTGCTCTTCAAAGACCCTTGTTCTGCCAAACCATGCTATGTTTGAATCAAATGTCAAGTGT  700

TTTCAGGAGTGTTAAGCAACATCCTGTTCAGCTGCACTAGTCCCTTACAGATGACCATGCTGATGGATCTATTCATCTATTATTAAATCTT  799

TATTTAGTTAACTATCTATAGGGCTTAAATTAGTTTTGTTCATTATTATATTATGTGAACTTTTACATTGAATTGTGTAACAAAAACATGTTCTTTAT  898

AATTTATTATTTGCCTGTTTATTAAATTTTTACTATAG
```

FIG. 8

PROMOTOR β-LACTAMASE    MET

...GAGACAATAACCCTGATAAATGCTTCAATAATATTGAAAAGGAAGAGTAATG

CYS ASP LEU PRO GLN THR HIS SER LEU GLY ASN ARG ARG ALA LEU ILE LEU LEU ALA GLN MET GLY ARG ILE PRO
TGT GAT CTG CCT CAG ACC CAC AGC CTG GGT AAT AGG AGG GCC TTG ATA CTC CTG GCA CAA ATG GGA AGA ATC CCC 144

PRO PHE SER CYS LEU LYS ASP ARG HIS ASP PHE GLY PHE PRO GLN GLU PHE ASP GLY ASN GLN PHE LYS
CCT TTC TCC TGC CTG AAG GAC AGA CAT GAC TTT GGA TTT CCC CAG GAG TTT GAT GGC AAC CAG TTC CAG AAG 219

ALA GLN ALA ILE SER VAL LEU HIS GLN MET ILE GLN SER THR LYS ASP LEU PHE SER SER ALA
GCT CAA GCC ATC TCT GTC CTC CAT GAG ATG ATC CAG AGC ACA AAG GAC CTC TTC AGC TCT GCT 294

THR TRP GLU GLN SER LEU LEU GLU LYS PHE SER THR GLU LEU ASN GLN LEU ASN ASP LEU GLU ALA CYS VAL
ACT TGG GAA CAG AGC CTC CTA GAA AAA TTT TCC ACT GAA CTT AAC CAG CAG CTG AAT GAC CTG GAA GCC TGC GTG 369

ILE GLN GLY VAL GLY VAL GLU GLY THR PRO LEU MET ASN VAL ASP SER ILE LEU ALA VAL LYS TYR PHE GLN
ATA CAG GAG GTT GGG GTG GAA GAG ACT CCC CTG ATG AAT GTG GAC TCC ATC CTG GCT GTG AAG AAA TAC TTC CAA 444

ARG ILE THR LEU TYR LEU THR GLU LYS LYS TYR SER PRO CYS ALA TRP GLU VAL VAL ARG ALA GLU ILE MET ARG
AGA ATC ACT CTT TAT CTG ACA GAG AAG AAA TAC AGC CCT TGT GCC TGG GAG GTT GTC AGA GCA GAA ATC ATG AGA 519

SER PHE SER LEU SER LYS ILE PHE GLN ARG LEU ARG ARG LYS GLU
TCC TTC TCT TTA TCA AAA ATT TTT CAA GAA AGA TTA AGG AGG AAG GAA TGA AACCTGTTCAACATGGAAATGATCTGTATT 601

GACTAATACACCAGTCCACACTTCTATGACTTCTGCCATTTCAAAGACTCATTTCTCCTATAACCACCGCATGAGTTGAATCAAAATTTCAGATCTTT 700

TCAGGAGTGTAAGGAAACATCATGTTTACCTGTGCAGGCACTAGTCCTTTACAGATGACCATGCTGATAGATCTAATTATCTATCTATTGAAATATTA 799

TTTATTATTAGATTTAAATTATTTTGTCCATGTAATATTATGTGTACTTTTACATTGTTATATCAAAATATGTTATTTATATTTAGTCAATATAT 898

TATTTCTTTTATTAATTTTTACTATTAAAACTTCTATATTATTGTTATTG...

CG-pBR(AP)/LyIFN-α-3

PROMOTOR β-LACTAMASE MET

...GAGACAATAACCCTGATAAATGCTTCAATAATATTGAAAAGGAAGAGTAATG

CYS ASP LEU PRO GLU THR HIS SER LEU ASP ASN ARG ARG THR LEU MET LEU ALA GLN MET SER ARG ILE SER
TGT GAT CTC CCT GAG ACC CAC AGC CTG GAT AAC AGG AGG ACC TTG ATG CTG GCA CAA ATG AGC AGA ATC TCT 144

PRO SER CYS LEU MET ASP ARG HIS ASP PHE GLY PHE PRO GLN GLU GLU PHE ASP GLY ASN GLN PHE GLN LYS
CCT TCC TGT CTG ATG GAC AGA CAT GAC TTT GGA TTT CCC CAG GAG GAG TTT GAT GGC AAC CAG TTC CAG AAG 219

ALA PRO ALA ILE SER VAL LEU HIS GLU LEU ILE GLN GLN ILE PHE ASN LEU PHE THR THR LYS ASP SER SER ALA
GCT CCA GCC ATC TCT GTC CTC CAT GAG CTC ATC CAG CAG ATC TTC AAC CTC TTT ACC ACA AAA GAT TCA TCT GCT 294

ALA TRP ASP GLU ASP LEU LEU ASP LYS PHE CYS THR GLU LEU TYR GLN GLN LEU ASN ASP LEU GLU ALA CYS VAL
GCT TGG GAT GAG GAC CTC CTA GAC AAA TTC TGC ACC GAA CTC TAC CAG CAG CTG AAT GAC TTG GAA GCC TGT GTG 369

MET GLN GLU GLU ARG VAL GLY GLU THR PRO LEU MET ASN ALA ASP SER ILE LEU ALA VAL LYS LYS TYR PHE ARG
ATG CAG GAG GAG AGG GTG GGA GAA ACT CCC CTG ATG AAT GCG GAC TCC ATC TTG GCT GTG AAG AAA TAC TTC CGA 444

ARG ILE THR LEU TYR LEU THR GLU LYS LYS TYR SER PRO CYS ALA TRP GLU VAL VAL ARG ALA GLU ILE MET ARG
AGA ATC ACT CTC TAT CTG ACA GAG AAG AAA TAC AGC CCT TGT GCC TGG GAG GTT GTC AGA GCA GAA ATC ATG AGA 519

SER LEU SER THR ASN LEU GLN LEU GLU ARG LEU ARG ARG LYS GLU
TCC CTC TCT TTA TCA ACA AAC TTG CAA GAA AGA TTA AGG AGG AAG GAA TAA CACCTGGTCCAACATGAAACAATTCTTATTG 601

ACTCATATACCAGGTCACGCTTTCATGAATTCTGCCATTTCAAAGACTCTCACTTCTGCTATAACTATGACCATGCTGATAAACTGATTTATCTATTTA 700

AATATTTATTAGCTATTCATAAGATTTAAATTATTTTGTTCATATAACATGTGCATCTTTACACTGTGGTTAGTGTAATAAAACATGTTCCTTA 799

TATTTACTCAAATTCATTATTTT...

Fig. 13

CG-pBR(AP)/LyIFN-α-2

PROMOTOR β-LACTAMASE     MET

```
...GAGACAATAACCCTGATAAATGCTTCAATAATATTGAAAAAGGAAGAGTAATG

CYS ASP LEU PRO GLN THR HIS SER LEU GLY ASN ARG ARG ALA LEU ILE LEU ALA GLN MET ARG ARG ILE SER
TGT GAT CTG CCT CAG ACT CAC AGC CTG GGT AAC AGG AGG GCC TTG ATA CTC CTG GCA CAA ATG CGA AGA ATC TCT 144

PRO PHE SER CYS LEU LYS ASP ARG HIS ASP PHE GLU PHE PRO GLN GLU GLU PHE ASP ASP LYS GLN PHE GLN LYS
CCT TTC TCC TGC CTG AAG GAC AGA CAT GAC TTT GAA TTC CCC CAG GAG GAG TTT GAT GAT AAA CAG TTC CAG AAG 219

ALA GLN ALA ILE SER VAL LEU HIS GLU MET ILE GLN GLN THR PHE ASN LEU PHE SER THR LYS ASP SER SER ALA
GCT CAA GCC ATC TCT GTC CTC CAT GAG ATG ATC CAG CAG ACC TTC AAC CTC TTC AGC ACA AAG GAC TCA TCT GCT 294

ALA LEU ASP GLU THR LEU LEU ASP GLU PHE TYR ILE GLU LEU ASP GLN GLN LEU ASN ASP LEU GLU SER CYS VAL
GCT TTG GAT GAG ACC CTT CTA GAT GAA TTC TAC ATC GAG CTT GAC CAG CAG CTG AAT GAC CTG GAG TCC TGT GTG 369

MET GLN VAL VAL GLY VAL ILE GLU SER PRO LEU MET TYR GLU ASP SER ILE LEU ALA VAL ARG LYS TYR PHE GLN
ATG CAG GTG GGG GTG ATA TCT CCC CTG ATG TAC GAG GAC TCC ATC CTG GCT GTG AGG AAA TAC TTC CAA 444

ARG ILE THR LEU TYR LEU THR GLU LYS LYS TYR SER SER CYS ALA TRP GLU VAL VAL ARG ALA GLU ILE MET ARG
AGA ATC ACT CTA TAT CTG ACA GAG AAG AAA TAC AGC TCT TGT GCC TGG GAG GTT GTC AGA GCA GAA ATC ATG AGA 519

SER PHE SER LEU SER ILE ASN LEU GLN LYS LYS ARG LEU LYS SER LYS GLU
TCC TTC TCT TTA TCA ATC AAC TTG CAA AAA AGA TTG AAG AGT AAG GAA TGA GACCTGGTACAACACGGAAATGATTCTTATA 601

GACTAATACAGCAGCTCACACTTCGACAAGTGTGCTCTTCAAAGACCCTTGTTGTTCTGCCAAAACCATGCTATGTTTGAATCAAATGTCAAGTGT 700

TTTCAGGAGTGTTAAGCAACATCCTGTTCAGCTGTATGGGCACTAGTCCCTTACAGATGACCATGCTGATGGATCTATTCATCTATTTAAATCTT 799

TATTTAGTTAACTATCTATAGGGCTTAAATTAGTTTGTTCATATATATATTATGTGAACTTTTACATTGTGAATTGTGTAACAAAAACATGTCTTTAT 898

ATTTATTATTTTGCCTTGTTTATTAAATTTTTACTATAG...
```

POLYPEPTIDES AND PROCESS FOR THE PRODUCTION THEREOF

This is a divisional of application Ser. No. 787,892 filed on Oct. 16, 1985, now abandoned which is a continuation-in-part of application Ser. No. 422,112 filed on Sept. 23, 1982, now abandoned.

FIELD OF THE INVENTION

The invention relates to DNAs derivable from human lymphoblastoid cells coding for interferon-like polypeptides, recombinant DNAs (vectors) containing corresponding DNA sequences as inserts, hosts transformed with said recombinant DNAs, and polypeptides with interferon-like activities. The invention also provides processes for the preparation of said DNAs, said recombinant DNAs, said hosts and said interferon-like polypeptides, wherein recombinant DNA technology is applied. The polypeptides of the invention are useful as immunomodulators, especially as antiviral, antitumor and anticancer agents. Accordingly, there are also provided pharmaceutical compositions containing said polypeptides and methods for treating viral infections, tumors and cancer.

BACKGROUND OF THE INVENTION

Interferons ("IFN") are a group of mostly glycosylated polypeptides having molecular weights from 10,000 to 40,000. They are produced by vertebrate cells upon exposure to an IFN inducer, such as a virus, a double-stranded RNA, intracellular microbes, microbial products, or various chemical agents (1). IFNs are usually not found in normal healthy cells. They assist the healthy cells of the vertebrate in their defence against viral infections and other attacks. IFNs have been found to have immunomodulator activities.

The nomenclature for interferon polypeptides has not yet been clearly established. According to recent recommendations (2), the classification will be based on the animal of origin (e.g. "Hu" for human origin), the antigenic specificity (types $\alpha$, $\beta$, $\gamma$ etc., based on their antigen-antibody reactions with $\alpha$-, $\beta$- or $\gamma$-IFN-antibodies, respectively), structural and physiological differences (subtypes are indicated by Arabic numbers, e.g. $\alpha_1$, $\alpha_2$ etc.) and the type of cells of origin (Le derived from leukocytes, Ly derived from lymphoblastoid cells, F derived from fibroblasts, etc.). Thus, e.g. HuIFN-$\alpha_1$ (Ly) or HuLyIFN-$\alpha_1$ indicates an $\alpha$-type interferon of subtype 1, which is derived from human lymphoblastoid cells. In addition to these denominations it may become necessary to specify whether the interferon is obtained directly from its progenitor cell or by synthesis in a microorganism, and whether the interferon is a particular subtype or a mixture of two or more interferon subtypes.

The nomenclature concerning the DNA sequences coding for IFN polypeptides, the recombinant DNA molecules and the hosts containing them has not been clearly established either. The nomenclature used for these DNA sequences reflects the interferon which they encode in abbreviated form. E.g., *Escherichia coli* HB 101 (Z-pBR 322 (Pst)/HcIF-2h) indicates the bacterial strain (*E. coli* HB 101) containing the recombinant plasmid DNA Z-pBR 322 (Pst)/HcIF-2h, i.e. the plasmid pBR 322 containing at the Pst I site (site of insertion of the foreign DNA) a HcIF-$\alpha_1$ insert, originated in Zürich (Z). The letter "H" indicates the human origin, "c" indicates a complementary DNA and $\alpha_1$ stands for the subtype (cf. C. Weissmann, (3)). In the given nomenclature example, the source of the IFN genes (leukocytes) is not indicated. In the present application a similar nomenclature is adopted, whereby however, the source of the IFN genes (lymphoblastoid cells) is indicated.

Three classes of the HuIFNs have been identified up to now: HuIFN-$\alpha$, HuIFN-$\beta$ and HuIFN-$\gamma$. HuIFN-$\alpha$ (formerly named LeIFN, leukocyte interferon, or LyIFN, lymphoblastoid interferon) is produced by human leukocytes(fresh cells obtained from the blood of human donors) and by lymphoblastoid cells upon induction, e.g. with a virus (E. A. Havell et al. (4) and A. D. Sagar et al. (5)). It is stable at pH2 (IFNs stable to acid were formerly indicated as "type I") and consists of a mixture of individual interferon polypeptides, which differ mainly in their degree of glycosylation (e.g. M. Rubinstein et al., (6)) and amino acid composition (see below). Of the two components isolated and purified so far, the one with a molecular weight of 15,000 to 18,000 is not glycosylated, whereas the other one with a molecular weight of 21,000 to 22,000 is glycosylated. W. E. Stewart, II et al. (7) have reported that the nonglycosylated interferon has retained most or all of its HuIFN-$\alpha$ activity. Parts of the amino acid sequence of HuIFN-$\alpha$ from lymphoblastoid cells have also been reported (K. C. Zoon et al., (8)). Various forms of HuIFN-$\alpha$ differing structurally and physiologically are already known. Particular human individuals may produce allelic variations of HuIFN-$\alpha$.

HuIFN-$\beta$ (formerly FIFN or FiIFN, "type I") is produced by human fibroblasts (e.g. cells of the foreskin of newborns) upon induction with a ds RNA and, to a minor extent, together with HuIFN-$\alpha$, by human lymphoblastoid cells upon induction with a virus. HuIFN-$\beta$ is also stable at pH2 (therefore it belongs to "type I"). At least two types of HuIFN-$\beta$ have been described so far (33, 48). The molecular weights are about 20,000 and 22,000. The amino acid sequence is known in part.

HuIFN-$\gamma$ [formerly named IIFN (immune interferon or "type II" interferon)] is produced by T-lymphocytes in response to antigens or mitogens. It is acid labile at pH2 and serologically distinct from HuIFN-$\alpha$ and HuIFN-$\beta$.

HuIFNs are useful as antivirus, antitumor and anticancer agents. As antiviral agents they can be used to treat e.g. viral respiratory infections, herpes simplex keratitis, acute hemorrhagic conjunctivitis, varicella zoster, hepatitis B, cytomegalic inclusion disease and others.

As antitumor or anticancer agents HuIFNs can be used to treat e.g. osteosarcoma, acute myeloid leukemia, multiple myeloma, Hodgkin's disease, melanoma, breast carcinoma, lymphosarcoma and papilloma and others.

HuIFNs may be used in the form of pharmaceutical preparations for oral or parenteral administration, e.g. pharmaceutical preparations for topical, intravenous, intramuscular, intranasal, intradermal or subcutaneous administration, for example tablets, vials, syrups, solutions or suspensions for oral administration, powders, injection or infusion solutions or suspensions, eye drops, ointments, sprays and the like.

The preparations are usually administered e.g. intramuscularly, once to three times daily in dosages of about $10^6$ to about $10^7$ units, the treatment depending on the disease, the mode of application and the condition of the patient. Virus infections are usually treated daily or up to three times daily over several days to several weeks, whereas tumors and cancers are treated for several months or years, either one to several times daily or twice or more times weekly.

Up to now HuIFN-α has been produced only in insufficient quantities through induced human cells, e.g. human lymphoblastoid cells (e.g. from Burkitt's lymphoma "Namalwa" cells) or human leukocytes obtained from the fresh blood of donors. HuIFN-β is obtained mainly from human fibroblasts. It is reported that only $2.6 \times 10^9$ IU of crude HuIFN-α are obtained from 800 l of cultured Namalwa cells, and that only about $10^{11}$ IU of crude HuIFN-α may be obtained annually at very large blood centers, e.g. the Finnish Red Cross Center in Helsinki. The specific activity of HuIFN-α is in the order of about $4 \times 10^8$ to $10^9$ IU/mg. The amount of HuIFN-α required for widespread and commercial application would be very low compared with other pharmaceutical compounds.

One hundred grams of pure HuIFN-α would provide between 10 and 30 million doses. However, such amounts cannot be produced industrially at a reasonable cost and expense using the human tissue culture and the human leukocyte technology.

Another disadvantage of these large scale production methods is that only mixtures of interferons are obtained and it is cumbersome and expensive to separate them into individual subtypes. Therefore, it has been unsatisfactory to assess the therapeutic applications of pure, individual interferon species so far.

The industrial application of these methods is furthermore limited to HuIFNs produced by human cells which can be cultured (such as human tumor cells and certain fibroblast cells) or to human cells which are available in relatively large amounts (such as leukocytes and lymphocytes). However, all of these methods are expensive and involved.

It was recognized that the solution to the problem of the industrial synthesis of large amounts of individual species of interferons could come from advances in molecular biology, through which it became possible to express a specific non-bacterial eukaryotic gene in bacterial cells. Recently, S. N. Cohen and H. W. Boyer (9) described a general method for replicating biologically functional DNA sequences. This method comprises the steps of cleaving a circular plasmid DNA to give a first linear DNA segment; inserting into this first segment a second linear DNA segment having a gene for a phenotypical trait to give a recombinant DNA molecule (a modified circular plasmid); transforming a unicellular microorganism with this recombinant DNA molecule; growing the transformants together with the non-transformed microorganisms under appropriate nutrient conditions; and isolating the transformants from the parent unicellular microorganisms. The transformants may than produce the desired protein.

The problem of producing a linear DNA sequence coding for interferons and therefrom a recombinant DNA was not solved by Cohen and Boyer.

DESCRIPTION OF PRIOR ART

DNA sequences derived from human leukocytes and fibroblasts, coding for polypeptides with HuIFN-α- and HuIFN-β-like activity, recombinant DNA molecules containing said DNA sequences, hosts transformed with said recombinant DNA molecules, polypeptides or culture fluids containing said polypeptides, and processes for the production of these compositions of matter have been described in various patent applications and other publications.

Using as starting material human leukocytes induced with Sendai virus, several polypeptides with HuIFN-α-like activity, the DNA sequences, recombinant DNA molecules, and hosts for their preparation are described by C. Weissmann (3; see also S. Nagata et al. (10), N. Mantei et al. (11) and M. Streuli et al.(12)).

Also derived from leukocytes, especially from the human myeloblastoid cell line KG-1 induced with Sendai virus, a partially purified HuIFN-α like polypeptide with a molecular weight of 21,000, the corresponding DNAs as well as the structure of eight distinct human LeIFN cDNAs are described by D. V. Goeddel et al.(13,14).

A method for preparing a polypeptide with HuIFN-α-like activity, starting from human lymphoblastoid Namalwa cells or human blood leukocytes, both induced with Newcastle disease virus, is disclosed in general terms in European patent application No. 34 307 (15), but without any concrete data or details being given.

Starting from human fibroblasts, especially from those obtained from the foreskin of newborns and induced by poly(I): poly(C), DNAs, recombinant DNA molecules coding for HuIFN-β, and microorganisms containing them, have been described in European patent application 28 033 ((16); see also Taniguchi et al. (17), Derynck et al. (18) and Goeddel et al.(19)).

mRNAs, DNAs, recombinant DNA molecules and bacterial strains capable of producing HuIFN-$β_1$ and HuIFN-$β_2$, are obtained by genetic engineering processes starting from human fibroblasts, especially from foreskin cells FS11 or SV80, induced with a double stranded poly(I): poly(C), according to UK patent application 2.063.882 (20).

DNAs, recombinant DNA molecules, E. coli containing the latter, and polypeptides having the activity of HuIFN-β, prepared via mRNA obtained from human fibroblasts, especially human foreskin FS-4 induced with poly(1): poly(C), and processes for the preparation thereof, are also disclosed in BE patent No. 887 397 (21).

In general terms, without giving any concrete data or details, the method for preparing a polypeptide with HuIFN-β-like activity, starting from human fibroblasts (foreskin of newborns) induced with poly(I): poly(C),is disclosed in European patent application 34 306 (22).

Human lymphoblastoid interferon "HuIFN(Ly)" can be producedin varying amounts by Namalwacells upon stimulation with various inducers (M. D. Johnston et al. (24)). HuIFN(Ly) produced by Namalwa cells induced by Sendai virus has been shown to contain HuIFN-α(Ly) (70–90%) and HuIFN-β(Ly) (10–30%). It consists of at least seven components. (K. C. Zoon et al. (8) and G. Allen et al. (25); see also E. A. Havell et al. (4) and A. D. Sagar et al. (5)). Although the total structure of the lymphoblastoid interferon polypeptides remains unknown at present, it became evident that HuIFN-α (Ly) is different from HuIFN-α (Le). There appears to be little, if any, glycosylation of the major components of lymphoblastoid interferon. The various components have not yet been separated and purified.

OBJECT OF THE INVENTION

Since clinical trials are being performed with mixtures of lymphoblastoid HuIFNs it is desirable to resolve the various components and produce them individually in order to be able to determine their therapeutic potential. None of the previously described recombinant DNA processes is directed toward the synthesis of lymphoblastoid human interferons. It is an object of the present invention to solve this problem by means of the recombinant DNA technology. It is also an object of the invention to elucidate the structure (amino acid sequences) of the various subtypes of HuLyIFNs and to provide methods which allow the individual interferons to be prepared in sufficient amounts in order to secure the supply for the treatment of large numbers of possible patients.

SUMMARY OF THE INVENTION

The present invention solves the problems of producing, also in large amounts, individual polypeptides with a biological activity similar to lymphoblastoid HuIFNs. The single polypeptides are either identical to or different from the hitherto known components of HuIFN-α (Le) and HuIFN-β.

Pharmaceutical preparations containing polypeptides displaying the immunological and biological activity of HuLyIFN-α or HuLyIFN-β and methods of use are also provided.

TERMS AND ABBREVIATIONS USED IN THE DESCRIPTION

Clone: A population of cells derived asexually from a single cell. Such a population is assumed to be genetically identical.

Operon: A genetic unit consisting of adjacent genes coordinately expressed under the control of an operator and a repressor.

Expression control sequence A sequence of nucleotides that controls and regulates expression of structural genes when operatively linked to those genes. It includes, inter alia, the promoter and the ribosomal binding site.

Promoter: A DNA segment at which RNA polymerase binds and initiates transcription.

Ribosomal binding site: Sequences which allow the binding of the mRNA to the ribosomes, a prerequisite for translation.

Expression: Process consisting of transcription and translation.

Transcription: A process involving base-pairing, whereby the genetic information contained in the DNA is used to order a complementary sequence of bases in a RNA chain.

Translation: The process whereby the genetic information present in an mRNA molecule directs the order of the specific amino acids during protein synthesis.

Nucleotide: The building block of the nucleic acids that consists of a purine or a pyrimidine base, a ribose or a 2-deoxyribose residue, and a phosphoric acid residue. The ribonucleotide bases are A, G, C and U, whereas in deoxyribonucleotides U is replaced with T.

Vector (or cloning vehicle): A DNA sequence, e.g. a plasmid or a phage DNA, which is able to replicate autonomously in a host cell, which contains a marker suitable for use in the identification of transformed cells, e.g. tetracycline resistance or ampicillin resistance, and to which another DNA segment may be attached experimentally so as to bring about the replication of the attached segment.

Plasmid: An extrachromosomal, circular, double-stranded DNA which is able to replicate in a host cell.

Recombinant (hybrid) DNA: A DNA molecule consisting of segments of DNA from different genes which have been joined outside living cells and have the capacity to infect some host cell and be maintained therein.

Nucleases: Enzymes which cleave the phosphodiester bonds of nucleic acid chains.

Ribonucleases (RNAses): Enzymes which can cleave the phosphodiester bonds of RNA.

Deoxyribonucleases (DNAses): Enzymes which can cleave the phosphodiester bonds of DNA.

Restriction endonucleases: Enzymes which cut polynucleotides at specific target sequences within the polymer chain. The cleavage products give rise to DNA fragments having "blunt" ("flushed") ends or "staggered" ("sticky") ends.

Exonucleases: Enzymes that digest DNA from the ends of strands.

Lysozymes: Enzymes that degrade the polysaccharides found in the cell walls of certain bacteria.

Reverse transcriptase: An enzyme coded by RNA tumor viruses which is able to make complementary single-stranded DNA chains from RNA templates and then to convert these DNA chains to double-helical form.

DNA polymerases: Enzymes which catalyze the formation of 3'-5' phosphodiester bonds of DNA.

DNA ligase: An enzyme which catalyzes the repair of a single-stranded DNA phosphodiester bond cleavage of the type introduced by an endonuclease.

Polynucleotide kinase: An enzyme which catalyzes the phosphorylation of 5'-hydroxyl groups of DNA.

Transformation: The introduction of an exogenous DNA, e.g. a plasmid or a hybrid DNA, into a cell followed by establishment of said DNA within the cell.

| | Abbreviations: |
|---|---|
| A | adenosine or deoxyadenosine monophosphate residue |
| U | uridine monophosphate residue |
| T | deoxythymidine monophosphate residue |
| C | cytidine or deoxycytidine monophosphate residue |
| G | guanosine or deoxyguanosine monophosphate residue |
| I | inosine monophosphate residue |
| dATP | deoxyadenosine triphosphate |
| dTTP | deoxythymidine triphosphate |
| dCTP | deoxycytidine triphosphate |
| dGTP | deoxyguanosine triphosphate |
| dCMP | deoxycytidine monophosphate |
| dGMP | deoxyguanosine monophosphate |
| RNA | ribonucleic acid |
| mRNA | messenger ribonucleic acid |
| tRNA | transfer ribonucleic acid |
| rRNA | ribosomal ribonucleic acid |
| ds RNA | double-stranded ribonucleic acid |
| DNA | deoxyribonucleic acid |
| cDNA | complementary deoxyribonucleic acid (enzymatically synthesized from a mRNA sequence) |
| ds cDNA | double-stranded complementary deoxyribonucleic acid |
| ApPr | expression control sequences of the β-lactamase gene |
| IFN | interferon |
| HuLy | (from) human lymphoblastoid cells |

BRIEF DESCRIPTION OF THE DRAWINGS

FIG. 4 displays the DNA sequence of the insert of CG-pBR 322/HLycIFN'b.

FIG. 5 displays the DNA sequence of the insert of CG-pBR 322/HLycIFN-$\beta_1$.

FIG. 6 displays the DNA sequence of the insert of CG-pBR 322/HLycIFN-$4_1$.

FIG. 7 displays the DNA sequence of the insert of CG-pBR 322/HLycIFN-8'.

FIG. 8 displays the DNA sequence of the insert of CG-pBR 322/HLycIFN-$5_1$.

FIG. 10 shows the CG-pBR(AP)/LyIFN-$\alpha$-1 sequence.

FIG. 12 shows the CG-pBR(AP)/LyIFN-$\alpha$-3 sequence.

FIG. 13 shows the CG-pBR(AP)/LyIFN-$\alpha$-2 sequence.

DETAILED DESCRIPTION OF THE INVENTION

Figure 1:
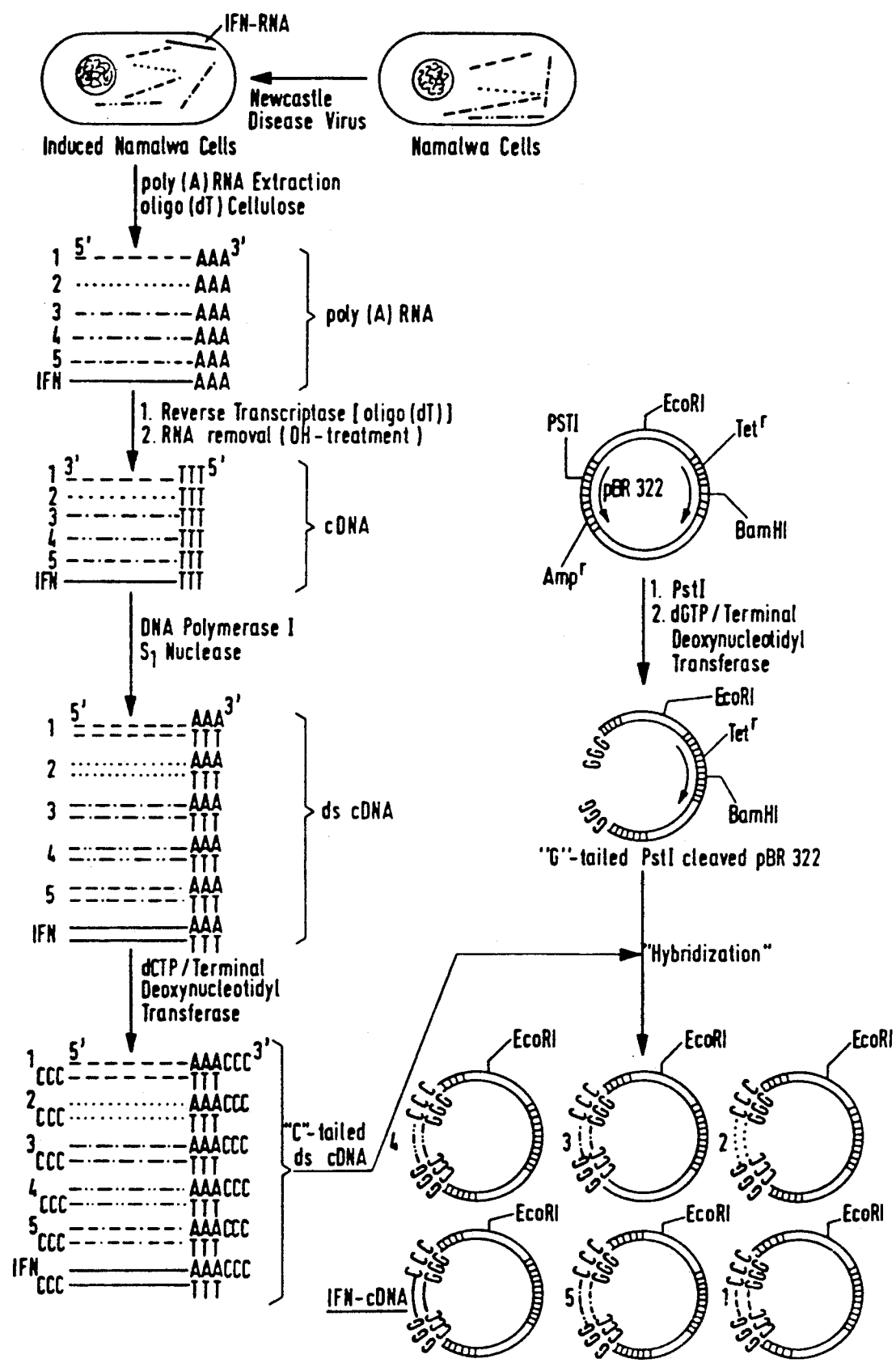
FIG. 1 shows cDNA synthesis and construction of recombinant DNA molecules.

The invention concerns a-DNA, especially a recombinant DNA, containing a DNA sequence derivable from human lymphoblastoid cells or a fragment, a variant or a mutant of said sequence, coding for an interferon-like polypeptide, or a DNA which hybridizes to said DNA, a host transformed with at least one of said recombinant DNAs, a polypeptide displaying the immunological and biological activity of a human lymphoblastoid interferon, or a fragment or a derivative thereof, a pharmaceutical composition comprising said polypeptide, and a method of treating viral infections, cancers or tumors in humans which comprises administering to said humans an effective amount of said polypeptide in the form of said pharmaceutical composition.

The invention also concerns a method for producing a polypeptide displaying the immunological and biological activity of a human lymphoblastoid interferon, characterized in that a host transformed with at least one of said recombinant DNAs is cultured and the desired polypeptide is collected, and a method for producing a transformed host microorganism.

The method for producing a transformed host microorganism comprises the steps of (1) isolating human lymphoblastoid poly(A) RNA from induced human lymphoblastoid cells and enriching it for HuLyIFN-mRNA, (2) preparing from this template a single-stranded complementary DNA and therefrom a double-stranded cDNA (3) introducing the ds cDNA into an appropriate vector DNA, (4) transforming an appropriate host microorganism with the obtained recombinant DNA, (5) culturing the host microorganisms and selecting the clones transformed with human lymphoblastoid IFN cDNA or DNA fragments, and optionally isolating the recombinant DNAs from the transformed host, if required modifying the recombinant DNAs in order to improve the level of polypeptides with IFN activity, and performing step (4) and (5) again. The invention furthermore concerns the individual steps and the combination of two or more of the individual steps.

1. Induction of human lymphoblastoid cells and isolation of human lymphoblastoid poly(A) RNA enriched for HuLyIFN mRNA The isolation of human lymphoblastoid poly(A) RNA enriched for HuLyIFN mRNA may beachieved by using various known procedures. The procedure used in the present invention comprises the following steps:

a. Induction of human lymphoblastoid cells for LyIFN synthesis,
b. Disruption of the induced cells,
c. Separation of lymphoblastoid poly(A) RNA from contaminating proteins, lipoproteins, DNAs and RNAs of a different kind,
d. Enrichment for LyIFN specific mRNA.

a. Induction of human lymphoblastoid cells for LyIFN synthesis

As a result of the exposure to an IFN inducer, human lymphoblastoid cells produce LyIFN mRNA and, subsequently, human LyIFN.

Suitable IFN inducers are, for example, various chemical agents, a double-stranded RNA. e.g. poly (I):poly (C), or especially certain viruses, above all members of the paramyxoviruses, pseudomyxoviruses, and reoviridial families, such as Newcastle disease virus (e.g. strains 110, B1, La Sota or Texas), Sendai virus, blue tongue virus, measles virus, mumps virus, parainfluenza virus type I, II or III, or Semliki Forest virus.

Human lymphoblastoid cells are advantageously those derived from patients with Burkitt's lymphoma One such cell line, Namalwa, was shown to produce high levels of IFN on viral stimulation (26). Apart from Namalwa cells, further lymphoblastoid cells can be used, such as for example, Daudi cells, Akuba cells. NC-37 cells, RN-2 cells and others known in the art.

Prior to the induction, the lymphoblastoid cells may be pretreated with a lower straight chain alkanoic acid, for example butyric acid, or a salt thereof which is known to enhance the IFN production by lymphoblastoid cells (27, 28). Furthermore, if necessary or desired, the lymphoblastoid cells may be primed by treating them with a small amount of homologous IFN.

The induction of the lymphoblastoid cells is carried out in a manner known from the literature for analogous procedures. Lymphoblastoid cells, e.g. Namalwa cells, are grown in a conventional nutrient medium (e.g. RPMI 1640 medium) supplemented with approximately 10% fetal calf serum, to a sufficient cell density (e.g. $10^6$-$10^7$ cells/ml). The cells, recovered from the medium by centrifugation and resuspended in the nutrient medium, are induced by adding a suitable virus, e.g. Newcastle disease virus, at a concentration of about 200 haemagglutination units per $10^6$ cells for an adequate period, e.g. for 5-16 hours. As soon as the induced cells produce IFN at a sufficient titer, the cells are harvested and further treated as described below. The IFN activity can be determined, for example, by the dye-uptake method developed by Armstrong (29).

b) Disruption of the induced cells

The first step in the isolation of a nucleic acid is its dissociation from the other cellular components comprising the disruption of the cells and the removal of contaminating proteins. Methods which are usable for cell disruption include repeated freezing and thawing, mechanical disruption, e.g. homogenizing with a motordriven TEFLON (polymerized tetrafluoroethylene) pestle in a glass homogenizer, bursting by osmotic shock, disruption by means of ultrasonic vibration and the use of lytic chemical agents such as anionic detergents, for example sodium dodecyl sulphate (SDS), lithium dodecyl sulphate, sodium 4-aminosalicylate, sodium dodecyl sarcosinate or sodium tri-isopropyl-naphthalene sulphonate. In certain cases, the application of anionic detergents may also result in partially releasing the nucleic acids from protein complexes and in partially inhibiting RNAse activity. Preferably, the procedure is carried out by using a high concentration of detergent and a brief exposure period in order to achieve a complete release of nucleic acids, especially RNA, with a minimum of degradation.

Advantageously, the induced cells are lysed by the action of an appropriate anionic detergent, e.g. sodium dodecyl sulphate, in a conventional buffer solution, e.g. in TNE. After a brief exposure period, the suspension is treated with a deproteinizing agent as described in paragraph c.

c) Separation of lymphoblastoid poly(A) RNA from contaminating proteins, lipoproteins, DNAs and RNAs of a different kind The deproteinization of the nucleic acid mixture obtained may be achieved by the action of chemical agents, e.g. chloroform containing 1-4% of 1-pentanol, or especially phenol. Proteins may also be removed by digestion with a protease, e.g. pronase or protease P, which digests almost any protein to amino acids. In order to ensure complete removal of proteins, a combination consisting of 2 chemical deproteinizing agents, e.g. phenol and chloroform, or treatment with a protease and subsequently with a chemical deproteinizing agent, e.g. phenol, may be used too.

In particular, the deproteinization of the nucleicacid-mixture is performed by incubation with a protease, e.g. pronase, and repeated extraction of the resulting mixture with phenol and subsequently with chloroform Employing the phenol system, nearly all of the denatured and digested proteins are transferred into the phenol and the interphase.

This and the subsequent steps for the recovery of the poly(A) RNA may be controlled for mRNA degradation by adding a small amount of a radioactively labeled marker mRNA, e.g. $^{125}$I-marked globin mRNA.

Purified deoxyribonuclease (free from RNAse) may be used to digest the contaminating DNA.

Alternatively the RNA can be received free from contaminating DNA by equilibrium centrifugation in CsCl gradients. Furthermore, the RNA can be separated from DNA by chromatographic methods, e.g. by hydroxy apatite column chromatography.

The mRNA molecules present in the purified solution differ from other RNA species, e.g. tRNA or rRNA, by a long uninterrupted sequence of adenosine nucleotides (100-200 residues long) at their 3'-end. These poly(A) chains can be utilized to select the mRNA in a manner known per se, e.g. by repeated batch adsorption to oligo(dT) cellulose or poly(U) sepharose. The bound poly(A) RNA is subsequently eluted by some washes with a solution at low ionic strength, e.g. with water.

A preferred embodiment of the isolation of poly(A) RNA comprises, for example, treating the nucleic acid mixture, obtained after lysis of the induced cells(step 1b), with a protease, extracting with phenol and subsequently with chloroform in order to remove the denatured and digested proteins, subjecting the resulting solution to oligo(dT) cellulose chromatography and eluting the bound poly(A) RNA with water. If desired or necessary, the adsorption to oligo(dT) cellulose can be repeated several times.

At this stage, the poly(A) RNA can be assayed for its capacity to direct the synthesis of polypeptides which exhibit HuIFN activity in an in vitro translation system (e.g.: reticulocyte translation system, Xenopus laevis). The IFN specific polypeptides can be identified by using a radio-immunoassay or, especially, a cytopathic bioassay. For this purpose, a sample of the recovered poly(A) RNA is dissolved in a suitable solvent, e.g. water, a diluted (for example 1 mM) EDTA solution or a conventional buffer mixture, and micro-injected into oocytes of the African claw toad (Xenopus laevis) according to Colman et al.(30). The IFN produced in the oocytes can be determined by a cytopathic bioassay, for example making use of the dye-binding assay according to Armstrong(29) or the reduction of a cytopathic effect according to Stewart et al.(31) applying a suitable challenge virus, e.g. vesicular stomatitis virus (VSV), on a human cell line, e.g. CCL-23 cells or Hep-2 cells. If desired, at any stage of the procedure described herein, the HuIF mRNA activity of a RNA, isolated in any state of purity or derived from a corresponding DNA, e.g. double-stranded cDNA, may be determined by any one of the assays mentioned.

d) Enrichment for LyIFN specific mRNA

After removal of other contaminating RNA species, e.g. tRNA and rRNA, or DNA (cf. paragraph 1c), the solution of poly(A) RNA in 0,5 mM-1 mM EDTA can further be purified by additional extractions with phenol and passing through a Chelex column in order to remove divalent cations.

The enrichment of this poly(A) RNA fraction for lymphoblastoid HuIFN mRNA can be achieved by various methods known from the literature. It is based essentially upon the differing molecular sizes of the mRNA species embodied.

The fractionation of poly(A) RNA according to size may be accomplished, for example, by gel filtration on columns of dextran derivatives or polyacrylamide, in which smaller RNA molecules penetrate the gel particles to a varying extent, whereas large molecules are not retained and pass through readily Furthermore, a mixture of poly(A) RNA species can be fractionated by zone electrophoresis through polyacrylamide, starch or agarose gels. Poly(A) RNAs can also be separated according to their sedimentation velocity by zone centrifugation through sucrose density gradients using sucrose solutions of about 5-23% as gradients.

For example, the fractionation of the poly(A) RNA mixture can be performed as follows. The poly(A) RNA solution released from other contaminating DNA and RNA species, is fractionated according to size by centrifugation through sucrose density gradients (e.g. 5-23%) in a conventional buffer system containing a small amount of EDTA. The fractions are collected and may be assayed for IFN mRNA activity as mentioned above (paragraph 1c).The fractions exhibiting the highest IFN mRNA activity, are pooled and applied to an oligo(dT) cellulose or poly(U) sepharose column. The bound poly(A) RNA which is considerably enriched forHuLyIFN mRNA is eluted with water and precipitated with ethanol.

At this stage, the HuLyIFN mRNA activity can be determined once again using the procedure mentioned above (cf. paragraph 1c). Generally, the sucrose gradient centrifugation results in a 10-20-fold enrichment for HuLyIFN mRNA.

2. Preparation of lymphoblastoid double-stranded cDNA containing HuLyIFN ds cDNA The poly(A) RNA enriched for HuLyIFN mRNA and obtained as described above (paragraph 1d) can be used as a template to prepare a double-stranded cDNA. This conversion involves the preparation of a single-stranded cDNA, the synthesis of the second DNA strand, and the digestion of the terminal "hairpin" structure generated primarily.

a. Preparation of the single-stranded cDNA

A single-stranded DNA showing complementarity to the poly(A) RNA described above (paragraph 1d) can be prepared by reverse transcription of said RNA. The synthesis is catalyzed by a RNA-dependent DNA polymerase (reverse transcriptase), for example from avian myeloblastosis virus(AMV). The AMV reverse transcriptasedoes not initiate the DNA synthesis on a single-stranded RNA. It is similar to DNA polymerase in that it requires a primer with a free 3'-hydroxyl group to be base-paired with the RNA template strand. Because of the poly(A) tails attached to the 3'-end of mRNAs, it is favourable to use, for example, oligodeoxythymidylate (oligo(dT)) or poly(U) as a primer. When sequence information is available, it is also possible to prime the cDNA synthesis selectively for the gene of interest.

For example, the synthesis of the single-stranded cDNA is accomplished as follows. The poly(A) RNA isolated and purified as described above is reacted in a conventional buffer mixture with a primer, e.g. oligo(dT), a magnesium salt, e.g. MgCl$_2$, a mercaptan, for example dithiothreitol (DTT), dATP, dGTP, dCTP, dTTP and AMV reverse transcriptase. Preferably, high concentrations of the deoxynucleosidetriphosphates are chosen in order to encourage the synthesis of full-size copies. The subsequent purification steps of the single-stranded cDNA are facilitated if one of the four deoxynucleosidetriphosphates used has been labeled, e.g., with $^{32}$P. The reaction can be terminated by the addition of an inhibition mixture, containing, for example, EDTA and SDS. After termination of the reaction, the product is deproteinized, for example by extracting the solution with phenol and chloroform, and then chromatographed on a Sephadex column to remove salts and unincorporated deoxynucleosidetriphosphates. Fractions containing the synthesized cDNA (provided that one of the deoxynucleoside-triphosphates has been labeled with $^{32}$P, the identification of usable fractions can easily be achieved by measuring the Cerenkov radiation) are pooled and the nucleic acids(RNA and cDNA) can be isolated, for example, by precipitation with ethanol. The template RNA is removed with a ribonuclease, for example RNAse A or RNAse Tl, or, preferably, by hydrolyzing with alkali, for example sodium hydroxide. The size of the remaining cDNA can be determined, for example, from its electrophoretic mobility in analkaline agarose gel or in a polyacrylamide gel relative to marker DNAs of known length (e.g. 32).

b) Preparation of the double-stranded cDNA

The single-stranded cDNA prepared as described above possesses a 3'-terminal "hairpin" structure. This "hairpin" structure constitutes a short double-stranded region which makes the cDNA self-priming for the subsequent synthesis of a second DNA strand. Hence, no additional primer is required.

The double-stranded cDNA can be synthesized by a RNA-dependent DNA-polymerase, e.g. AMV reverse transcriptase, in a manner similar to that described above in the synthesis of the single-stranded cDNA, except that poly(A) RNA is replaced by single-stranded cDNA and the primer is omitted. Alternatively, other enzymes catalyzing the synthesis of DNA from its deoxyribonucleotide precursors can be used as well, for example T4 DNA polymerase, *E. coli* DNA polymerase (Klenow fragment) or, preferably, *E. coli* DNA polymerase I.

The second strand synthesis can be performed using a buffer mixture which contains the single-stranded cDNA, a magnesium salt, e.g. MgCl$_2$, a mercaptan, e.g. dithiothreitol, the four deoxynucleoside triphosphates, one of which is radioactively labeled, e.g. with $^3$H, and a DNA polymerase, e.g. *E. coli* DNA polymerase I. After termination of the reaction and deproteinization of the mixture (cf. paragraph 2a) the DNA is precipitated with ethanol.

The obtained ds DNA contains a "hairpin" loop connecting the two DNA strands. The loop can be cut by Sl nuclease yielding a ds cDNA with base-paired ends. The digestion can be performed in a conventional buffer mixture treating the product of the second strand synthesis with Sl nuclease in the presence of a zinc salt, e.g. zinc sulphate. The digestion can be stopped by adding SDS and EDTA. After deproteinization with phenol, the solution is chromatographed on a Sephadex column. Fractions containing the ds cDNA (which can be determined, for example, by measuring the Cerenkov radiation of each fraction) are pooled and the ds cDNA is precipitated with ethanol.

Advantageously, the synthesized ds cDNA which still consists of a large member of different species is further enriched at this stage for full-sized ds cDNA. Methods suitable for this purpose include gel filtration, electrophoresis on polyacrylamide gel or on an agarose gel, or zone centrifugation in a sucrose gradient. Co-electrophoresis and co-centrifugation of DNA molecules of known molecular size, in parallel runs, permit the location of those ds cDNA molecules which possess the molecular size expected for IFN ds cDNAs (700-1200 base pairs according to the data published previously: 14, 16, 18, 33).

For example, the ds cDNA, dissolved in a conventional buffer medium, is subjected to zone centrifugation through sucrose gradients (e.g. 5-23%). DNA species which sediment faster than a suitable marker DNA run in parallel gradients (e.g. a 700-800 base pair marker), are isolated.

3. The cloning of the ds cDNA enriched for HuLyIFN ds cDNA a. General considerations The cloning of the ds cDNA obtained as described above (paragraph 2b) can be accomplished by methods known per se. The procedure involves
joining the ds cDNA to an appropriate vector DNA and transferring the resulting recombinant DNA into an appropriate host cell (transformation) in which it is able to replicate.

A vector DNA is a DNA molecule which contains genetic functions ensuring its own replication when transferred to a host cell. Furthermore, it is desirable that the vector DNA contains a gene by which plasmid-carrying host cells (transformants) can be selected from a large population of cells, most of which do not contain the plasmid. Examples of vector DNAs commonly used in genetic engineering are circular plasmid DNA and the DNA of certain bacteriophages to which the ds cDNA may be attached experimentally, for example derivatives of the bacterioplage λ and, particularly, the plasmid col E1 or its derivatives, for example pMB 9, pSF 2124, pBR 317 and, especially, pBR 322. The plasmids mentioned contain genes for ampicillin resistance and, in part, for tetracycline resistance. Therefore, host cells containing such a plasmid will exhibit a phenotype which allow the separation of transformants from the parent host.

For example, in order to obtain a recombinant DNA molecule, a suitable plasmid, e.g. pBR 322, is cleaved, the ds cDNA is inserted into the linearized plasmid, and the ring is reclosed forming an enlarged recombinant plasmid molecule comprising the inserted ds cDNA segment. Advantageously, the plasmid DNA is cleaved at defined sites. For this purpose, a large number of restriction endonucleases are available which recognize specific DNA sequences. Some restriction endonucleases cleave both DNA strands at the same point, producing "blunt" ends. Others catalyze the cleavage of bonds separated by a few nucleotides from each other, producing free single-stranded regions at each end of the cleaved molecule ("staggered" ends).

DNA segments are usually joined through their single-stranded cohesive ends and covalently closed by a DNA ligase, e.g. T4 DNA ligase. Complementary ends can be formed in two distinct ways: either by cleavage with restriction enzymes making staggered cuts and generating cohesive termini, or through the addition of defined single-stranded sequences (e.g. homopolymeric tails). Alternatively, fully base-paired DNA-duplexes, blunt-ends, can be joined by T4 ligase. For example, a plasmid, e.g. pBR 322, is cleaved by a suitable restriction endonuclease, e.g. Pst I, the linearized plasmid and the ds cDNA to be inserted are each elongated in the presence of an appropriate enzyme, e.g. terminal deoxynucleotidyl transferase, with single-stranded homopolymeric tails. For example, poly(dC) tails can be added to one DNA preparation and poly(dG) tails can be added to another (alternatively, dA and dT tails can be chosen as well). The two types of DNA can then be joined through their complementary ends.

Useful hosts include, for example, yeasts and, especially, bacteria which are susceptible to transformation and lack restriction enzymes and modification enzymes, for example strains of E. coli, e.g. E. coli X 1776, or E. coli HB 101, or strains of Bacillus subtilis, Bacillus stearothermophilus, Pseudomonas, Haemophilus, Streptococcus and other bacteria, and mutants thereof.

The recombinant DNA molecule prepared as described before can be transferred into the suitable host cell by means of common transformation procedures, including e.g. $Ca^{2+}$-pretreatment of the host cells. Cells containing a recombinant plasmid DNA which confers a phenotypical property, e.g. tetracycline resistance, to the host cell, are selected by plating in a selective, e.g. tetracycline-containing, nutrient medium on agar plates.

In the present invention, the preferred vector DNA is the plasmid pBR 322 which, after cleavage with an appropriate restriction endonuclease, especially Pst I, is linked to the ds cDNA via complementary homopolymeric tails, especially dG:dC-tails. The resulting recombinant DNA is transferred to E. coli HB 101.

Instead of IFN genes prepared via the ds cDNA synthetic route according to the preceding chapters the corresponding chromosomal DNA can likewise be used for the preparation of clones capable of producing polypeptides with IFN activity.

The chromosomal DNA may be obtained from human lymphoblastoid cells, such as Namalwa cells, by methods known in the art, e.g. by partial cleavage of the entire chromosomal DNA with Alu I, and joining the obtained fragments with EcoR I linkers to λ Charon 4A arms, or by cleaving the chromosomal DNA with a restriction enzyme, e.g. Kpn I or Hind III, and ligating the obtained fragments to a vector DNA, such as to the plasmid pBR 322 or to cosmid DNA. The recombinant vector DNA can be transformed into a host such as E. Coli. The colonies containing the chromosomal IFN α and β genes are identified by colony hybridisation (see chapter 4a) either by using a radioactively labeled synthetic oligodeoxynucleotide or a radioactively labeled α and β specific IFN cDNA as a probe. Sub-fragments can be obtained by restricting the identified fragments with an appropriate endonuclease or by digesting them with an appropriate exonuclease.

Therefore, the invention also concerns a method for the preparation of a DNA containing a DNA sequence derivable from human lymphoblastoid cells or a fragment, a variant or a mutant of said sequence, coding for an interferon-like polypeptide, or a DNA which hybridizes to said DNA, which process comprises (1) preparing from HuLyIFN-mRNA a single-stranded complementary DNA and, if required, therefrom a double-stranded cDNA, or (2) partially cleaving the chromosomal DNA of human lymphoblastoid cells and selecting fragments which contain chromosomal LyIFN genes, and, if a fragment of said sequence is required, restricting said DNA with an appropriate endonuclease or partially digesting said DNA with an appropriate exonuclease, or, if a recombinant DNA is required, introducing said DNA into an appropriate vector DNA.

b. Preparation of linearized, deoxynucleotide-elongated pBR 322

The preferred vector of the present invention, the plasmid pBR 322, is a small plasmid consisting of 4361 base pairs. It contains two genes ($amp^r$, $tet^r$) which confer ampicillin and tetracycline resistance respectively on bacterial recipient cells and which can be used for selection and identification of transformed cells. There are several restriction sites within pBR 322. A single Pst I site is within the $amp^r$ gene while the sole BamH I, Hind III and Sal I sites are within the $tet^r$ gene. A single EcoR I site is present elsewhere (34). On application of one of the surnamed restriction endonucleases, either the $amp^r$ gene or the $tet^r$ gene or both genes remain intact. Therefore, either of the enzymes cited is suitable for the cleavage and linearization of pBR 322.

After the plasmid pBR 322 has been linearized, deoxynucleotide chains may be added to both 3'-ends in the presence of terminal deoxynucleotidyl transferase. Preferably, about 20 to 50 deoxynucleotide residues are added in order to ensure a stable joint to the ds cDNA elongated by chains of the complementary deoxynucleotides. For example, the plasmid pBR 322 is treated in an adequately buffered aqueous medium containing $MgCl_2$, a mercaptan, e.g. 2-mercaptoethanol, and a carrier protein source, e.g. bovine serum albumin or gelatin, additionally with a restriction endonuclease, e.g. Pst I. After the digestion has been terminated, the solution is deproteinized with, for example, phenol. The terminal addition of deoxynucleotidyl residues is carried out in a conventional buffer system containing $MgCl_2$, sodium cacodylate and a carrier protein, e.g. bovine serum albumin, with a sufficient amount of deoxynucleosidetriphosphates, e.g. dGTP, and terminal deoxynucleotidyl transferase.

c. Preparation of deoxynucleotide-elongated ds cDNA

The elongation of the ds cDNA obtained as described above (paragraph 2b) can be accomplished in the same way as the synthesis of the linearized, deoxynucleotide-elongated plasmid pBR 322 (cf. paragraph 3b)using the complementary deoxynucleosidetriphosphate (e.g. dCTP instead of dGTP) and, preferably, using $CoCl_2$ instead of $MgCl_2$. For example, the ds cDNA is incubated in a buffer solution containing sodium cacodylate, $CoCl_2$, a protein, e.g. bovine serum albumin, the corresponding deoxynucleosidetriphosphate, e.g. dCTP, and terminal deoxynucleotidyl transferase.

d. Annealing of linearized, chain-elongated pBR 322 and chain-elongated ds cDNA

The linearized, chain-elongated plasmid pBR 322 and the chain-elongated ds cDNA can be annealed and recircularized in a conventional manner, that is to say by base-pairing of the complementary deoxynucleotide chains.

In order to promote circle formation and to prevent the formation of concatomers (joining of different linear hybrid plasmids) the reaction must be performed at low concentration of both chain-elongated ds cDNA and linearized pBR 322 molecules.

For example, a mixture of deoxynucleotide-elongated (e.g. dCMP-elongated) ds cDNA and linearized deoxynucleotide-elongated (e.g. dGMP-elongated) pBR 322 is incubated at 4 successive 1 h stages at different temperatures (e.g. 65° C., 46° C., 37° C. and 20° C.). The annealed DNA can be used directly for transformation into a compatible bacterium, e.g. E. coli HB 101.

It must be indicated at this point that the product of the annealing procedure contains recombinant DNA molecules, of which only a very few are related to HuLyIFN, since most of the recombinants contain a cDNA insert derived from a mRNA other than LyIFN mRNA.

e. Transformation of E. coli HB 101 with the dnnealed hybrid plasmids

The annealed hybrid plasmids obtained can be employed to transform E. coli HB 101. The plasmids are replicated within the cell and the plasmid replicas are distributed to the daughter cells when the cell divides.

The transformation of E. coli HB 101 with the annealed hybrid plasmids may be accomplished by procedures known from the literature. The procedure includes $Ca^{2+}$-pretreatment of the cells so as to allow DNA uptake (e.g. (35)) and incubation with the hybrid plasmid. Then the cells may be transferred to a selective growth medium which allows separation of the transformed cells from the parent cells. Since the hybrid plasmid still contains a tet$^r$ gene, an agar medium containing tetracycline as a growth inhibiting substance is advantageously chosen.

For example, the hybrid plasmid and the E. coli HB 101 cells pretreated with $Ca^{2+}$ are incubated in a buffer medium containing a $Ca^{2+}$-salt, e.g. $CaCl_2$, and a $Mg^{2+}$-salt, e.g. $MgCl_2$. After a sufficient incubation period (e.g., 10–40 min), the bacteria are subjected to a heat pulse (35–42° C.), generally for a short period (1–5 min), the cells are chilled and plated on an agar medium, e.g. tryptone agar or Mc Conkey agar, supplemented with a sufficient amount of tetracycline. Cells which survive in such a medium contain the recircularized plasmid or the hybrid plasmid DNA. Therefore, the grown colonies are used for screening for appropriate clones.

4. Identification of clones containing lymphoblastoid IFN cDNA a. Methods suitable for the identification of clones containing LyIFN cDNA Colonies containing specific genes can be identified by various methods, for example RNA selection hybridization, differential hybridization, or hybridization with a synthetic probe on the one hand, or clones producing a particular gene product can be identified by immunological or biological assays on the other hand.

While the immunological and biological approaches rely on the production of the immunologically and biologically detectable gene product, the first set of methods depends basically on the availability of an appropriate probe which is in a sufficiently purified condition to prevent unspecific hybrid formation. Suitable probes are the mRNA complementary to the desired gene or the corresponding cDNA.

Several approaches are known for screening for bacterial clones containing human leukocyte and fibroblast IFN. For example, Goeddel et al. (13) and Sugano et al. (16) identified IFN genes by visual comparison of two hybridization sets. The first set was hybridized with a radioactive cDNA which was synthesized by reverse transcription of a mRNA mixture obtained from induced cells, using $^{32}P$-labeled CTP as a labeling agent and oligo (dT) (Sugano) or a synthetic deoxyundecanucleotide (Goeddel) as a primer. The second set was hybridized with a radioactive cDNA produced in a similar manner from a mRNA mixture obtained from uninduced cells. This procedure is characterized by the lack of specificity and reproducibility, as is obvious from the data shown. Another approach, described by Weissmann (3), makes use of the RNA selection hybridization procedure, which comprises a tedious and laborious multi-step search for the desired clone.

The methods mentioned are not applicable to the purpose of the present invention to isolate both LyIFN-α and -β genes, because the concentration of IFN-β amounts only to approximately 10% of the concentration of IFN-α in human LyIFN. This small quantity is below the limit of detectability of these methods.

In consequence of the unsatisfactory approaches prior to this invention, a new screening procedure has been developed, comprising the synthesis of a 5'-terminal labeled oligodeoxynucleotide complementary to both IFN-α and IFN-β mRNAs, the reverse transcription of poly(A)RNA enriched for LyIFN mRNA using said oligodeoxynucleotide as a primer, and the in situ colony hybridization of the filter-bound plasmid DNAs with the labeled cDNA probe. This approach permits the specific, rapid and direct detection of both IFN-α and -β genes containing the base sequence of the synthesized primer oligodeoxynucleotide and does not require further cumbersome hybridization-translation assays as described in the prior art. The in situ colony hybridization is based on the general method described by Grunstein and Hogness (36) or on variants thereof. In this procedure, colonies are grown on or transferred to nitrocellulose filters, lysed by alkali treatment and fixed to the filters in situ A probe of radioactively labeled nucleic acid complementary to the desired gene is subsequently hybridized to the filter-bound DNA. As the hybridized probe can be detected autoradiographically, the corresponding colonies containing a hybridizable DNA can be isolated from a reference set of nitrocellulose filters.

A comparison of the coding stretches of the cDNAs of cloned human IFN-α and IFN-β has revealed a stretch of 13 nucleotides which both cDNAs (and, self-evidently, the corresponding mRNAs also) have in common (23). Therefore, a synthetic 13-mer oligodeoxynucleotide which has the above mentioned contiguous base sequence can be used to prime the cDNA synthesis from human lymphoblastoid IFN-α and -β mRNA.

b. Preparation of a $^{32}$p-labeled human IFN-α and IFN-β specific cDNA probe

There are several proven approaches for synthesizing an oligodeoxynucleotide of given structure (37). For example, the oligodeoxynucleotide synthesis can be effected using chemical methods, e.g. the diester or the triester method. The basic step of the diester method is the joining of two suitable protected deoxynucleotides to form a dideoxynucleotide containing a phosphodiester bond. The triester method differs from the diester method in the presence of an additional organic protective group on the phosphate groups rendering the deoxynucleotides and oligodeoxynucleotides soluble in organic solvents. Alternatively, the synthesis can be performed enzymatically using polynucleotide phosphorylase which, under controlled conditions, adds predominantly a single deoxynucleotide to a short oligodeoxynucleotide. The reactions can be carried out in solution or by solid-phase techniques which have been perfected to a high degree recently.

For example, the synthesis of the 13-mer oligodeoxynucleotide of the formula

5'-CCTTCTGGAACTG-3' complementary to both human IFN-α and -β mRNA can be accomplished by the triester-method as described by Itakura (38) and de Rooij (39) using protected mono-, di-, and trideoxynucleotides as starting materials. A single step of the procedure is illustrated by the following scheme showing the synthesis of a dinucleotide

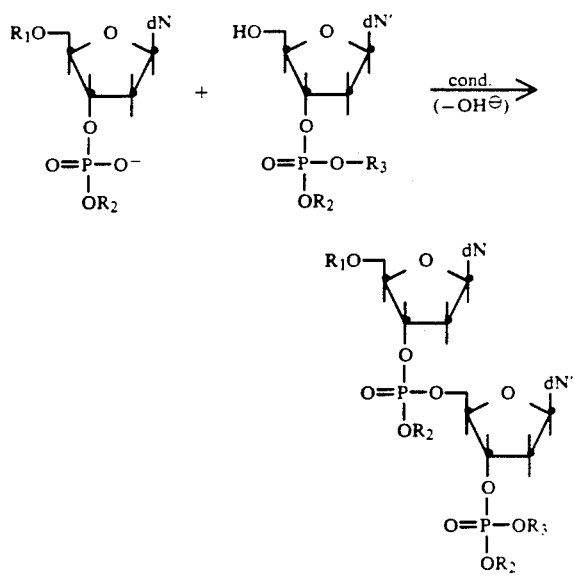

wherein $R_1$, $R_2$ and $R_3$ are protective groups, dN and dN' are purine or pyrimidine bases, and cond. is a condensing agent.

The starting materials used in the present synthesis (protected or partially protected mono-, di-, or trideoxynucleotides) are known from the literature.

The protective groups are advantageously chosen such that they can be successively removed under mild conditions without cleavage of the nucleotide 3'-5'-linkages. Suitable protective groups $R_1$ are, for example, monomethoxytrityl or dimethoxytrityl, $R_2$ is, for example, 2-chlorophenyl, and $R_3$ is, for example, 2-cyanoethyl.

Exocyclic amino functions in the adenine, guanine, and cytosine residues are protected in particular by acyl groups, for example benzoyl or isobutyryl. As condensing agent, 2,4,6-triisopropylbenzenesulphonic acid can be used, for example.

The specific removal of single protecting groups (e.g. $R_3$, $R_1$ and $R_2$) in intermediate compounds and the complete deblocking of the fully protected 13-mer oligodeoxynucleotide can be performed by known methods. For example, a 2-cyanoethyl group $R_3$ can be removed by treatment with alkali, a monomethoxytrityl group $R_1$ is removed by treatment with 80% acetic acid, and a 2-chlorophenyl group $R_2$ is removed with tetrabutylammoniumfluoride. Other methods known in the art can be used as well. The individual steps of the synthesis are outlined in FIG. 2.

The prepared 13-mer oligodeoxynucleotide primer can be purified by conventional chromatographical methods, for example by DEAE-Sephadex chromatography and/or by high performance liquid chromatography (HPLC). The primer is 5'-$^{32}$P-labeled so as to render possible the detection of the hybridized probe in the subsequent hybridization procedure. The labeling is accomplished by reacting the synthesized primer with a labeled phosphorylating agent, e.g. [γ-$^{32}$P]-ATP, with T4 polynucleotide Kinase in a conventional buffer mixture. The resulting solution containing the $^{32}$P-labeled primer is purified by deproteinization, e.g. with phenol, and by chromatographic means, e.g. by Sephadex chromatography or polyacrylamide gel electrophoresis. If desired, the nucleotide sequence can be verified at this stage by two-dimensional homochromatography.

The poly(A)RNA enriched for LyIFN mRNA (cf. step 1d) is used as a template for the synthesis of an IFN-α and -β specific cDNA probe as follows: The cDNA synthesis is effected in essentially the same manner as described above (step 2a) except that the 5'-labeled synthetic oligodeoxynucleotide is used as a primer instead of oligo(dT). The labeled cDNA product is deproteinized with, e.g., phenol and collected by precipitation with ethanol. Further purification can be effected, for example, by polyacrylamide gel electrophoresis of the cDNA product. The product can be visualized autoradiographically.

A single DNA band which is specific for poly(A)RNA from induced cells and not present in the product obtained by using poly(A)RNA from non-induced cells is extracted from the gel. Its size can be determined, for example, from its relative mobility in relation to labeled marker DNAs of known length. The product represents a $^{32}P$-labeled human LyIFN-α and -β specific cDNA probe.

c. Screening for clones containing lymphoblastoid IFN cDNA

Colonies which survive and grow on an agar medium supplemented with tetracycline (cf. paragraph 3e) are screened for clones containing lymphoblastoid IFN cDNA. For this purpose, the in situ colony hybridization procedure is chosen as depicted above (paragraph 4a). The transformant colonies are transferred to nitrocellulose filters and a reference set of these colonies is then obtained by replica plating to additional agar plates. The colonies on the filters are lysed, their DNA is denatured and fixed to the filters in situ (36).

Prior to the hybridization procedure, the denatured DNA on the filters is advantageously pre-hybridized with a mixture containing, inter alia, a DNA of foreign provenance, in order to obtain lower backgrounds and to saturate non-specific hybridizing sites. Subsequently, the radioactively labeled cDNA probe prepared as described above (paragraph 4b) is hybridized to the filter-bound DNA covered with mineral oil. After the filters have been freed from mineral oil and other contaminants, the result of the hybridization procedure can be monitored by autoradiographical analysis on an X-ray film. Colonies exhibiting a positive response on the X-ray film, can be picked from the reference set and used for further investigation.

Preferably, only one part of the transformant colonies are transferred to the nitrocellulose filters. The remaining colonies will be used for further screening procedures detailed below (paragraph 4d). For example, the DNA fixed to the nitrocellulose filters is treated with a conventional pre-hybridizing mixture containing, inter alia, a denatured DNA, e.g. denatured calf-thymus DNA, bovine serum albumin, Ficoll, and polyvinylpyrrolidone, and thereupon hybridized with the radioactively labeled cDNA probe (cf. paragraph 4b) under paraffin oil using standard hybridization procedures (cf. 36). After the hybridization has been terminated, the filters are successively washed with chloroform and with a buffer mixture containing SDS and low salt in order to remove the paraffin oil and the unhybridized cDNA, respectively. The filters are exposed to X-ray films for autoradiography. Hybridized colonies display a positive response and can be picked from the reference set.

The identified colonies contain recombinant DNAs with inserts complementary to those of the cDNA probe, i.e. DNA segments which correspond to human lymphoblastoid genes or fragments thereof. Since the primary clones of transformed cells occasionally contain more than one species of recombinant DNA molecules, the hybrid plasmid DNAs are isolated from the positively hybridized clones and used to retransform E. coli HB 101 as described before (paragraph 3e). The hybrid plasmid DNAs can be isolated, for example, by the following procedure. At first, each colony identified is cultured in an appropriate nutrient medium, e.g. in tryptone medium, in the presence of tetracycline to eliminate those contaminating cells which do not contain any plasmid. The surviving cells are harvested, dissolved in a conventional buffer system and disrupted in a gentle manner so that the chromosomes remain inside the cell envelopes. This process involves, for example, the successive addition of lysozyme, EDTA and an nonionic detergent, e.g. Triton. Then, the cell debris and the chromosomal DNA are removed by centrifugation. The supernatant solution is deproteinized, e.g. with phenol, and the RNA degraded with a RNAse, e.g. RNAse A. The hybrid plasmid DNA can be separated from RNA fragments by precipitation with polyethylene glycol and purified by reprecipitation with ethanol.

At this stage, the cleavage pattern of each isolated hybrid DNA can be determined by cleavage with an appropriate restriction endonuclease, especially that which has been used to linearize the plasmid pBR 322, the site at which the ds cDNA is inserted (cf paragraph 3b). The size of the restriction fragments can be determined, for example, from their electrophoretic mobility in an agarose gel relative to marker DNAs of known length.

Each of the isolated hybrid DNAs is retransformed into E. coli HB 101 and grown on an appropriate agar medium (cf. paragraph 3e) containing tetracycline From each retransformation, some clones are picked and the hybrid plasmid DNA of each clone is isolated as described above. The hybrid plasmid DNAs are subjected to restriction analysis once again and a complete or a partial nucleotide sequence analysis of the cDNA insert is performed in order to select hybrid DNAs which are suitable for further proceedings. Furthermore, the partial sequence analysis may clarify whether the inserted IFN cDNA segments correspond to the human lymphoblastoid IFN-α or -β genes.

At present, several rapid methods are available for sequencing DNA molecules. The primed synthesis methods, developed especially by Sanger (40), make use of the ability of DNA polymerases to synthesize accurately a complementary copy of a single-stranded DNA template using radioactively labeled DNA fragments generated by restriction endonuclease digestion as primers. Alternatively, the chemical DNA sequencing method developped by Maxam and Gilbert (41) can be chosen. In this method, the DNA to be sequenced is end-labeled, partially cleaved at each of the four bases in four different reactions and the products are fractionated by size, e.g. by means of gel electrophoresis under denaturing conditions The DNA sequence can be read from the pattern of the radioactive bands. In order to determine the complete nucleotide sequence of a chosen stretch of DNA, a restriction endonuclease is required which cuts the DNA in that region.

By means of the method of Maxam and Gilbert, the sequence of up to 100-150 bases in both directions from the cut can be resolved in one experiment.

For example, the isolated hybrid DNAs can be digested with suitable restriction endonucleases, e.g. Pst I, EcoR I, Bgl II, Pvu II or Alu I, at sites which occur within the cDNA insert. The resulting DNA fragments are terminally labeled, for example, with $[\gamma\text{-}^{32}P]$-ATP in the presence of a polynucleotide kinase, and cleaved with a second restriction endonuclease such that only one strand of the ds DNA remains terminally labeled. The appropriate DNA fragments are isolated by, for example, polyacrylamide gel electrophoresis. Subsequently the DNA fragments are subjected to the base-specific cleavage reactions described by Maxam and Gilbert (41). The products are fractionated by electrophoresis, e.g. on polyacrylamide gel under denaturing conditions, e.g. in 7M urea, and the DNA fragments can be visualized autoradiographically.

d. Identification of additional clones containing lymphoblastoid IFN cDNA

As described above (paragraph 4c), one part of the transformant colonies is transferred to nitrocellulose filters and their fixed DNA is subjected to in situ colony hybridization using a radioactively labeled cDNA as a probe, e.g. an IFN specific cDNA probe. The recombinant DNAs of positively hybridizing colonies can be used to screen for additional clones containing recombinant DNA molecules having the same or a related DNA insert (e.g. IFN related sequences).

For this purpose, the plasmid DNAs of each of the identified colonies (corresponding to different IFN genes or gene fragments) obtained in the first screening procedure (paragraph 4c) are isolated as described above and cleaved with restriction endonucleases such that plasmid fragments containing the IFN cDNA insert or part thereof are obtained. After these plasmid fragments have been 5'-terminally labeled and the appropriate DNA fragments (e.g. containing a radioactively labeled IFN insert or a part thereof) isolated, e.g. by polyacrylamide gel electrophoresis, they can be used either singly or, alternatively, as a mixture. For hybridization, transformant colonies (see above) are transferred to nitrocellulose filters and lysed. Their DNA is denatured, fixed to the filters in situ and hybridized with the IFN specific, radioactively labeled DNA fragments according to Grunstein and Hogness (36). Hybridizing colonies can be visualized autoradiographically and picked from a reference set.

The identified colonies contain recombinant DNA molecules having an identical or a similar cDNA insert as the probes used. By this screening procedure, additional clones can hence be identified which contain lymphoblastoid IFN-α or -β IFN genes or fragments thereof. The plasmid DNA of each identified colony can be isolated and characterized by restriction analysis and (partial) sequence analysis as described above (paragraph 4c).

5. Synthesis of polypeptides having HuLyIFN-like activity by E. coli containing HuLyIFN-specific recombinant DNAs The HuLyIFN cDNA inserts of the present invention have been inserted via hybridization into the Pst I site of pBR 322 (see above) Since the Pst I site of pBR 322 lies within the β-lactamase gene, a fused protein may result when the cDNA insert is ligated into that position in the proper orientation in regard to transcription and in the proper reading frame in regard to translation If the inserted cDNA has its own initiation signal and/or a termination signal in phase with the β-lactamase sequence, initiation and/or reinitiation may occur also at the second initiation signal and a non-fused protein may result. Nevertheless, even those clones are valuable which do not display any IFN activity although a HuLyIFN cDNA is present In that case, the cDNA insert may be isolated and ligated to the expression control region in an appropriate fashion (see paragraph 6) in order to obtain high levels of expression of the desired polypeptide.

Clones containing a recombinant DNA with a HuLyIFN cDNA insert can be tested for IFN activity by conventional means. For example, cultures may be grown to an adequate cell density. The cells are harvested, resuspended and lysed (cf. paragraph 1b) The cell free extracts can be assayed for IFN activity using, for example, a cytopathic bioassay (e.g. 29).

Clones which synthesize polypeptides with HuLyIFN activity to a satisfactory degree are suitable for large-scale production. The clones can be cultured and the polypeptides can be recovered as described in chapters 7 and 8.

6. Construction of recombinant plasmids capable of expressing high levels of polypeptides with HuLyIFN activity In order to be efficiently expressed, a gene must be properly located with respect to the control region including the initiator of transcription (promoter) and translation (ribosomal binding site).

As described above (paragraph 3d), the plasmid pBR 322 has been cleaved with an appropriate restriction endonuclease and linked to HuLy cDNA. The resulting recombinant plasmid DNA has been used to transform E. coli HB 101. If, for example, Pst I is used as a restriction endonuclease, the insertion of the HuLy cDNA will occur within the β-lactamase gene of pBR 322. Furthermore, if the ligation has been achieved in the proper orientation and proper reading frame, a fused protein may result consisting of part of the β-lactamase chain followed by the HuLyIFN amino acid sequence. In case the cDNA has not been inserted in the proper reading frame and/or orientation, the resulting protein will not display any IFN activity. In the event of improper orientation, the plasmid can be re-oriented by excising the cDNA insert with a suitable restriction endonuclease (in the present invention all inserts are excisible by Pst I) and re-ligating the cDNA and the linearized plasmid. The resulting hybrid plasmid can be transformed into E. coli HB 101, which in turn can be assayed for IFN activity as usual.

In order to enhance the efficiency of the HuLyIFN cDNA insert expression, it is necessary to locate the HuLyIFN cDNA insert at the vicinity of the expression control sequence mentioned above such that no extra nucleotides (and therefore amino acids) are preceding the gene (and therefore the polypeptide with HuLyIFN activity). Furthermore in the case of HuLyIFNs, the primary translation products are pre-interferons consisting of signal peptides attached to the N-terminus of mature interferons. The signal peptide sequences are post-translationally removed in the original progenitor cell. However, E. coli will not be able to remove the presequences proteolytically. Therefore, the presequences are advantageously removed from the cDNA insert by appropriate methods (see below) such that the primary translation product will be a mature IFN-like polypeptide. For this purpose, the gene coding for mature HuLyIFN is reconstituted in vitro and reinserted into a plasmid close (operably linked) to an expression control sequence, e.g. the expression control sequence of the β-lactamase gene. Other expression control sequences, including, inter alia, the promoter and the ribosomal binding site, can be used as well, e.g. the control sequence of the lactose operon, tryptophan operon, arabinose operon and the like, the corresponding sequences of the phage λ N-gene and the phage fd coat protein gene, or other sequences known in the art. The expression control sequence can be inserted in a plasmid already containing the cDNA insert, or the cDNA can be inserted in a plasmid already containing the expression control sequence, or both DNA fragments can successively be inserted into the plasmid.

For example, the mature HuLyIFN cDNA can be placed under the control of the β-lactamase expression control sequence Since the mature cDNA insert coding for a mature HuLyIFN-like polypeptide does not start with the codon ATG which is necessary for the initiation of translation, the ATG-triplet has to be entered synthetically. For example, knowing the nucleotide base sequences and, consequently, the restriction endonuclease patterns of both pBR 322 and the HuLyIFN cDNA, the following approach can be used. The plasmid pBR 322 is cleaved with Pst I within the β-lactamase gene and digested with an exonuclease, e.g. Bal 31, to shorten the β-lactamase coding sequence. Alternatively, a combination of λ-exonuclease (5'-exonuclease) or 3'-exonuclease from E. coli and S1 nuclease, can be used as well. The restricted plasmid is ligated with a ds DNA linker which can be synthesized, e.g. by the triester approach described above (paragraph 4b). The linker includes the recognition sequence of an appropriate restriction endonuclease, e.g. Bcl I (Sau 3A). The resulting plasmid fragment is cleaved with the restriction endonuclease characteristic of the annealed linker (e.g. Bcl I) and, subsequently, with EcoR I (there is an EcoR I site within pBR 322 which is located in the vicinity of the β-lactamase expression control sequence). The resulting DNA fragment, e.g. EcoR I - Bcl I DNA fragment, essentially consists of the expression control sequence of β-lactamase (ApPr) and the annealed linker, and can be isolated by polyacrylamide electrophoresis.

On the other hand, the HuLyIFN cDNA insert is excised from a recombinant DNA molecule containing it (paragraph 4d), e.g. by digestion with the restriction endonuclease Pst I. The isolated HuLyIFN cDNA insert is further cleaved with another restriction endonuclease (or, if necessary, with two other restriction endonucleases and partially re-ligated) in order to remove the DNA sequence which is coding for the signal peptide The resulting mature HuLyIFN cDNA has a sticky end complementary to that of the ApPr DNA fragment mentioned above (e.g. a Sau 3A sticky end). The mature HuLyIFN cDNA and the ApPr DNA fragments are annealed by ligase as usual (cf. paragraph 3d). The annealing must result in the formation of an ATG codon preceding the first codon of the mature cDNA in order to establish a proper reading frame. The resulting hybrid DNA contains the β-lactamase expression control region, an ATG translation start codon, a DNA sequence coding for the complete HuLyIFN and two restriction endonuclease ends (e.g. EcoR I and Pst I ends) which are suitable for inserting the hybrid DNA in the plasmid pBR 322 cleaved accordingly.

The resulting hybrid plasmid can be used to transform E. coli HB 101 and to direct the synthesis of high levels of a polypeptide with HuLyIFN activity.

7. Cultivation of clones containing HuLyIFN-specific recombinant DNAs

The transformed hosts according to the present invention can be used for the production of polypeptides with HuLyIFN activity. The method for producing said polypeptides is characterized in that the transformed host, especially a transformed E. coli strain, is cultured in a liquid nutrient medium containing assimilable sources of carbon and nitrogen and inorganic salts.

Various carbon sources can be used. Examples of preferred carbon sources are assimilable carbohydrates, such as glucose, maltose, mannitol or lactose, or an acetate, which can be used either alone or in suitable mixtures. Suitable nitrogen sources include, for example, amino acids, such as casamino acids, peptides and proteins and their degradation products, such as tryptone, peptone or meat extracts, furthermore yeast extract, malt extract, corn steep liquor, as well as ammonium salts, such as ammonium chloride, sulphate or nitrate, which can be used either alone or in suitable mixtures.

Inorganic salts which may be used include, for example sulphates, chlorides, phosphates and carbonates of sodium, potassium, magnesium and calcium.

Additionally, the nutrient medium may also contain growth promoting substances and/or substances exerting a selection pressure in order to prevent the loss of the HuLyIFN-specific recombinant DNA. Substances which promote growth include, for example, trace elements, such as iron, zinc, manganese and the like, or individual amino acids. Apart from the gene coding for a polypeptide with HuLyIFN activity, the recombinant DNAs according to the invention preferably contain a gene conferring antibiotic resistance, for example resistance against ampicillin and/or tetracycline. If such an antibiotic substance is added to the culture medium, cells containing the recombinant DNA will survive and grow whereas cells which have lost said recombinant DNA or foreign antibiotic-sensitive microorganisms contaminating the culture medium will not.

The cultivation is carried out employing conventional techniques. The culturing conditions, such as temperature, pH of the medium and fermentation time are selected in such a way that maximal levels of IFN-like polypeptides are produced. A chosen E. coli strain is preferably grown under aerobic conditions in submerged culture with shaking or stirring at a temperature of about 20° to 40° C., preferably at about 30° C., at a pH value of from 4 to 9, preferably at pH 7, and for about 4 to 20 hours, preferably for 8 to 12 hours. As a result of the cultivation, IFN-like polypeptides are accumulated intracellularly.

8. Isolation and purification of polypeptides with IFN activity

The human lymphoblastoid interferons according to the present invention can be recovered from the culture broth comprising the steps of liberating said polypeptides from the cells of the transformed host and purifying them.

After the transformed E. coli cells have been grown to a satisfactory cell density, the first step for the recovery of the expressed polypeptide consists in liberating it from the cell interior. To this purpose the cells are lysed by treatment with a detergent, such as SDS or Triton. Alternatively, mechanical forces, such as shearing forces (for example X-press, French press) or shakening with glass beads or alumina, may be used to break cells. The resulting polypeptide mixture can be enriched for human LyIFN by conventional means, such as precipitation with ammonium sulphate or trichloroacetic acid, gel electrophoresis, dialysis, chromatography, for example, ion exchange chromatography, size-exclusion chromatography or reverse phase HPLC, and the like. The final purification of the pre-purified product can be achieved, for example, by means of antibody affinity chromatography. In principle, the purification steps can be accomplished according to the method of Staehelin et al. (51) developed for the purification of human leukocyte interferon.

For example, the isolation and purification of human LyIFN can be performed using the following steps:
(1) lysis of the *E. coli* cells,
(2) removal of part of the non-proteinaceous material by treatment with polyethyleneimine,
(3) precipitation of the polypeptides by saturating the solution with ammonium sulphate,
(4) dialysis in an appropriate buffer mixture,
(5) column chromatography on DEAE-cellulose,
(6) affinity chromatography on a monoclonal antibody column, and
(7) molecular sizing on a suitable Sephadex ®-column.

In order to obtain a sufficiently pure product additional purification steps may turn out to be necessary, e.g. cation or anion exchange chromatography, adsorption on hydroxylapatite, reverse phase HPLC etc. On the other hand, one or more of the above steps may be omitted if possible, or the order of steps may be altered.

The present invention also comprises fragments and derivatives of the polypeptides of the present invention, for example proteolytically cleaved polypeptides, fully or partially protected, e.g. acylated, silylated and especially glycosylated polypeptides, and salts thereof, and conventional processes for their preparation.

The invention concerns in particular the DNAs and the polypeptides of the present invention in substantially pure form and especially DNAs, transformed hosts, polypeptides and processes for their preparation as described in the Examples.

The polypeptides of the present invention and suitable derivatives thereof, e.g. glycosylated products, are used in analogy to the known interferons for the treatment of viral infections, tumors and cancers of the human body, optionally in combination with other antiviral, antitumor or anticancer agents, preferably in the form of pharmaceutical preparations that contain an effective amount of the active ingredient together or in admixture with inorganic or organic, solid or liquid, pharmaceutically acceptable carriers which are suitable preferably for parenteral administration.

The pharmacologically active compounds of the present invention are preferably used in the form of preparations or infusion solutions for parenteral, for example intramuscular or intravenous, administration. Such solutions are preferably isotonic aqueous solutions or suspensions which can be prepared before use, for example from lyophilised preparations which contain the active ingredient alone or together with a pharmaceutically acceptable carrier. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations, which may, if desired, contain further pharmacologically valuable substances, are produced in a manner known per se, for example by means of conventional dissolving or lyophilising processes, and contain from approximately 0.1% to 100%, especially from approximately 1% to approximately 50%, and in the case of lyophilisates up to 100%, of the active ingredient.

The invention also concerns a method for producing a pharmaceutical composition characterized in that a pharmacologically active compound of the present invention is admixted with a pharmaceutically acceptable carrier.

Depending upon the nature of the disease and the condition of the patient, the preparations are usually administered, e.g. intramuscularly, one to three times daily in dosages of about $10^6$ to about $10^7$ units.

The following Examples serve to illustrate the present invention but should not be construed as a limitation thereof.

EXAMPLES

The following abbreviations are used in the Examples:

| | |
|---|---|
| EtBr: | ethidium bromide |
| BSA: | bovine serum albumin |
| DTT: | 1,4-dithiothreitol (1,4-dimercapto-2,3-butanediol) |
| EDTA: | ethylenediaminetetraacetic acid |
| SDS: | sodium dodecyl sulphate |
| TNE: | solution containing 100 mM NaCl, 50 mM Tris.HCl (pH 7.5), and 5 mM EDTA. |
| Tris (Trizma): | tris-(hydroxymethyl)-aminomethane |
| Tris.HCl: | monohydrochloride of Tris |

1. Isolation of poly(A) RNA enriched for HuIFN mRNA (FIG. 1) a) Induction of the Namalwa cells Namalwa cells are grown in culture medium RPMI 1640 containing 10% fetal calf serum at 37° C. When a cell density of $3 \cdot 10^6$ cells/ml is reached, the suspension is centrifuged at 800×g for 10 minutes at room temperature. The collected cells are resuspended in 200 ml of culture medium containing glutamine (0.027% by volume), penicillin (200 units/ml) and streptomycin (50 µg/ml). The cells are incubated for 90 minutes at 37° C. with Newcastle diseasevirus (NDV 110) at a ratio of 190 HAU/$10^6$ cells (HAU: haemagglutination units). By adding fresh culture medium the cell density is adjusted to $1.3 \cdot 10^6$ cells/ml and the cell suspension is shaken at 34° C. at 100 rpm. After 12 h, $6 \cdot 10^9$ cells are harvested and resuspended in 50 ml phosphate-buffered saline ("PBS"; 1 l PBS contains 80 g NaCl, 2 g KCl, 14.4 g Na$_2$HPO$_4$ and 2 g KH$_2$PO$_4$). Before harvesting the cells, a sample is removed and the interferon activity is determined according to the procedure of Armstrong (29) using human CCL-23 cells and vesicular stomatitis virus (VSV) as the challenge virus. 4300 IFN units/ml are found.

b) Disruption of the cells and deproteinization

The cell suspension ($6 \cdot 10^9$ cells in 50 ml PBS) is added at room temperature to 800 ml lysis buffer consisting of 0.05M Tris-HCl (pH 7.5), 0.1M NaCl, 5 mM EDTA and 2% SDS (cryst. research grade, Serva). The lysate is digested with 0.2 mg/ml of preincubated (2 h at 37° C.) protease (Protease P, type VI, Sigma) at room temperature for 1 h while stirring the solution. The solution is deproteinized by extracting 3 times with 500 ml phenol satured with TNE and 5 times with 500 ml chloroform. 500 mg of nucleic acids are obtained as measured by absorbance at 260 nm.

c) Removal of contaminating DNA and RNA

The slightly viscous aqueous solution obtained as described above (step 1b) is adjusted to 0.3M NaCl and 1 g of oligo(dT) cellulose (type 7, P-L Biochemicals) is added. After stirring for 30 min at room temperature the suspension is centrifuged in 1 l Sorvall bottles in a Sorvall RC-3 centrifuge at 4,000 rpm for 10 min at room temperature and the oligo(dT) qellulose slurry is washed twice with 40 ml 2×TNE containing 0.5% SDS. The bound poly(A) RNA is then eluted by five successive washes with 2.5 ml H$_2$O. The yield is 720 μg poly(A) RNA as determined by measuring the optical density. The supernatant RNA solution from the first adsorption is adsorbed a second time to 1 g of oligo(dT) cellulose and eluted as described above, yielding 320 μg poly(A) RNA. The eluates are pooled, adjusted to TNE and the poly(A) RNA is precipitated with 67% ethanol at −20° C. for 10 hours. The RNA is collected by centrifugation at 10,000 rpm in a Sorwall RC-5B centrifuge for 10 min at 0° C. The precipitate (1 mg) is redissolved in 1 ml of 1 mM EDTA.

The RNA is assayed for HuIFN mRNA activity by injection into oocytes of Xenopus laevis as follows:

50 nl of the RNA solution is injected into each of 20 oocytes. The oocytes are incubated in Barth medium (2 mM Tris, 88 mM NaCl, 1 mM KCl, 0.33 mM Ca(NO$_3$)$_2$·H$_2$O, 0.41 mM CaCl$_2$.2H$_2$O, 0.82 mM MgSO$_4$.7H$_2$O, 2.4 mM NaHCO$_3$, 0.01 mg/ml penicillin, 0.01 mg/ml streptomycin; the solution is adjusted to pH 7.6 with HCl) according to Gurdon (42), Barth (43) and Colman et al.(30). The injected oocytes are incubated for 42-48 hours and the incubation medium is removed, centrifuged for 5 min in an Eppendorf centrifuge, and the supernatant is stored at −20° C. or −80° C. until it is used for assay. The IFN activity is assayed essentially according to Armstrong (29), except that VSV is used as the challenge virus on Hep-2-cells (Flow Laboratories). The oocyte extract has a specific activity of 600 IU interferon per μg RNA injected.

d) Enriching the poly(A) RNA for HuIFN mRNA

The poly(A) RNA is passed through a Chelex-100 column (200–400 mesh, Bio-Rad) of 0.5 ml bed volume. The column is rinsed with 1 ml of 1 mM EDTA.

The eluate (1 mg poly(A) RNA in 2 ml EDTA) is heated for 2 min at 100° C. and subjected to centrifugation through a sucrose density gradient (6 14 ml sucrose solutions increasing in sucrose concentration from 5% to 23% (m/v) and containing 50 mM Tris-HCl [pH 7.5], 0.2M NaCl and 1 mM EDTA). The centrifugation is carried out in a TST 41 rotor (Kontron AG) at 35,000 rpm for 16 h at 5° C. 0.3 ml fractions are collected with an ISCO gradient collector. 2 volumes of ethanol are added to each fraction and the solution is allowed to stand for 10 h at −20° C. The precipitated mRNA is collected by centrifugation (Sorvall, HB-4 rotor at 0° C., 10,000 rpm for 10 min). The precipitate of each fraction is redissolved in 25 μl of 1 mM EDTA and each fraction is assayed for human IFN mRNA activity as described above (step 1c), except that only 10 oocytes are injected per RNA sample instead of 20. The results are given in table 1.

TABLE 1

| HuIFN mRNA activity from fractions of sucrose-density gradient. | |
|---|---|
| fraction No. | IFN activity (units/ml) |
| 1–18 | — |
| 19 | 162 |
| 20 | 162 |
| 21 | 162 |
| 22 | 162 |
| 23 | not tested |
| 24 | 729 |
| 25 | not tested |
| 26 | 405 |
| 27 | not tested |
| 28 | 486 |
| 29 | not tested |
| 30 | 162 |
| 31 | not tested |
| 32 | 162 |
| 33 | not tested |
| 34 | 54 |
| 35–40 | not tested |

The fractions 23–29 are pooled and the poly(A) RNA is purified further as follows:

The poly(A) RNA solution is adjusted to 2×TNE in 0.5% SDS and applied on a 200 μl oligo(dT) cellulose column. The column is washed with 2 ml of 2×TNE in 0.5% SDS and the poly(A) RNA is eluted by 5 washes with 0.5 ml H$_2$O. The eluate is adjusted to TNE and the solution is extracted twice with an equal volume of phenol (saturated in TNE) and twice with an equal volume of chloroform. The poly(A) RNA is precipitated with 2 volumes of ethanol at −20° C. for 10 hours and collected by centrifugation in a HB-4 rotor as described before.

The poly(A) RNA is dissolved in 100 μl of 0.5 mM EDTA. The yield is 40 μg as determined by measuring the optical density.

A portion of the poly(A) RNA is assayed for human IFN activity as described above by using 20 oocytes per assay. The poly(A) RNA preparation has a specific activity of 8100 IU interferon per μg RNA.

2. Preparation of double-stranded cDNA (FIG. 1)

Poly(A) RNA enriched for HuIFN mRNA (see step 1d) is used as a template to prepare double-stranded cDNA essentially as described by Efstratiadis et al. (44), Maniatis et al. (45) and Hoeijmakers et al. (46).

a) First strand synthesis

250 μl reaction mixture containing 40 mM Tris-HCl (pH 7.5), 30 mM NaCl, 5 mM MgCl$_2$, 0.5 mM DTT (Calbiochem.), 1 mM dGTP, dCTP, dTTP (P-L Biochemicals) and 1 mM $^{32}$P-dATP (Amersham, specific activity 50,000 cpm/nmole), 20 μg/ml oligo(dT)$_{12-18}$ (P-L Biochemicals), 40 μg/ml poly(A) RNA and 100 units of avian myeloblastosis virus (AMV) reverse transcriptase (Life Sciences, Inc., St. Petersburg, Florida) are incubated for 80 min at 37° C. The reaction is terminated by adjusting the solution to 10 mM EDTA and 0.1% SDS. The mixture is extracted once with 1 volume of phenol. The aqueous phase is reextracted with 1 volume of chloroform and applied on a 3 ml Sephadex G-50 (Pharmacia, fine) column. 0.1 ml fractions are collected. The radioactivity of each fraction is determined by measuring the Cerenkov radiation. Radioactive fractions are pooled and the nucleic acids are precipitated with 2 volumes of ethanol at −20° C. for 10 h. The sample is centrifuged in a HB-4 rotor for 20 min at 10,000 rpm at 0° C. The precipitate is dissolved in 95 μl of H₂O. 5 μl of 10N NaOH is added and the mixture is incubated at 25° C. for 40 min. After neutralization with 5M acetic acid, 50 μl H₂O and 2 volumes of ethanol are added and the sample is stored at −20° C. for 10 hrs. The precipitate is collected by centrifugation as described before and redissolved in 200 μl of 0.1 mM EDTA. The yield of single-stranded cDNA is 3.7 μg. The size of the cDNA is 700–1500 nucleotides in length, as determined from its electrophoretic mobility in a 6% polyacrylamide gel in Tris-borate-EDTA (108 g of Tris, 9.3 g of disodium EDTA, and 55 g of boric acid per one 1 solution of pH 8.3) containing 7M urea relative to marker DNAs of known length (32).

b) Second strand synthesis and S₁ endonuclease digestion

The obtained cDNA solution is heated at 100° C. for 90 sec, chilled and incubated in a 400 μl reaction mixture comprising 0.1M potassium phosphate buffer (pH 6.9), 10 mM MgCl₂, 10 mM DTT (Calbiochem), 1 mM dATP, 1 mM dCTP, 1 mM dTTP (P-L, Biochemicals), 1 mM ³H-dGTP (Amersham, specific activity 94,000 cpm/nmole) and 165 units/ml of *E.coli* DNA polymerase I (Biolabs, New England) for 8 h at 15° C. The reaction is terminated by adding EDTA and SDS to final concentrations of 10 mM and 0.1%, respectively. The mixture is extracted with phenol and chloroform, chromatographed over Sephadex G-50 (Pharmacia, fine, 2 ml bed volume) and ethanol precipitated as described above (step 2a).

The resulting DNA is treated in a 50 μl incubation mixture containing 0.25M NaCl, 50 mM sodium acetate (pH 4.5) and 1 mM ZnSO₄ with 6 units of S₁ endonuclease (P-L Biochemicals) at 37° C. for 30 min. The reaction is stopped with 0.1% SDS and 10 mM EDTA. The reaction mixture is deproteinized with 1 volume of phenol (saturated in 50 mM sodium acetate, pH 4.5) and chloroform. The aqueous phase is chromatographed on a 2 ml Sephadex G-50 (Pharmacia, fine) column in TNE. 100 μl fractions are collected and the Cerenkov radiation of each fraction is determined. The excluded fractions are pooled and the DNA is precipitated with 2 volumes of ethanol at −20° C. for 10 h as described above. The precipitate is centrifuged in a HB-4 rotor (see above) and the collected precipitate is dissolved in a 100 μl solution containing 10 mM Tris·HCl (pH 7.5) and 0.5 mM EDTA. 4 μg of DNA are obtained.

The DNA is fractionated through a sucrose density gradient (5–23%) in 50 mM Tris-HCl (pH 7.5) and 1 mM EDTA in a TST-60 rotor (Kontron AG). Centrifugation is carried out at 55,000 rpm for 5 h at 15° C. The DNA, which sediments faster than a 800 base pair marker DNA, run in a parallel gradient, is pooled, adjusted to TNE and precipitated with 67% ethanol at −20° C. for 10 hrs. 0.4 μg double-stranded cDNA are obtained 3. Preparation of pBR 322—linked cDNA (FIG. 1)

a) Preparation of dCMP-elongated cDNA

The 3'-termini of 0.1 μg of the obtained ds cDNA are provided with poly(dC) tails in a 10 μl reaction volume containing 100 mM sodium cacodylate (pH 7.2), 2.5 mM CoCl₂, 50 μg BSA (Calbiochem.) per ml, 1 mM dCTP and 10 units of terminal deoxynucleotidyl transferase (P-L Biochemicals) per μg of ds cDNA. After incubation (20 min at 27° C.), EDTA is added to 10 mM and the sample is stored at −20° C. until use.

b) Preparation of Pst I cleaved, dGMP elongated pBR 322

10 μg of pBR 322 plasmid DNA is digested with 10 units of Pst I endonuclease (Biolabs) in a 100 μl solution containing 50 mM NaCl, 6 mM Tris·HCl (pH 7.5), 6 mM MgCl₂, 6 mM 2-mercaptoethanol and 100 μg/ml gelatine for 1 h at 37° C. The solution is extracted with 1 volume of phenol and chloroform. The solution is adjusted to TNE and the linearized DNA is precipitated with 2 volumes of ethanol at −20° C. for 5 h.

The linearized plasmid DNA is elongated with dGMP in a 200 μl reaction volume containing 100 mM sodium cacodylate (pH 7.2), 5 mM MgCl₂, 20 mM NaH₂PO₄, 50 μg BSA per ml, 1 mM dGTP and 100 units of terminal deoxynucleotidyl transferase (P-L Biochemicals). After incubation for 20 min at 37° C., EDTA is added to 10 mM and the reaction mixture is frozen at −20° C. until use.

c) Annealing of dGMP-elongated pBR 322 to dCMP-elongatedds cDNA

A mixture of dCMP-elongated double-stranded cDNA (0.1 μg) and dGMP-tailed linearized pBR 322 (0.5 μg) in 500 μl TNE buffer is incubated at 65° C. for one hour, at 46° C. for one hour, at 37° C. for one hour and at 20° C. for one hour. The solution containing the pBR 322-linked cDNA is put on ice and used isrsediately for transformation.

4. Transformation of *E. coli* HB 101 with the annealed hybrid plasmid

Calcium treated *E. coli* HB 101 is prepared for transformationby the method of Mandel et al. (35).

10 μl of the reaction mixture containing the annealed pBR 322 hybrid plasmid DNAs prepared as described above (step 3c) are added to a mixture containing 150 μl calcium-treated *E. coli* HB 101 in 10 mM MgCl₂, 10 mM CaCl₂ and 10 mM Tris·HCl (pH 7.5) in a total volume of 200 μl.

The mixture is cooled in ice for 20 min, heated to 42° C. for 1 min and incubated at 20° C. for 10 min. 1 ml of tryptone medium (tryptone medium contains 10 g Bacto-Trypton (Difco); 1 g yeast extract (Difco); 1 g glucose; 8 g NaCl and 294 mg CaCl₂.2 H₂O in 1 l of distilled water) is added and the mixture is incubated for 30 min at 37° C. by shaking at 300 rpm. The mixture is plated onto 2 agar plates (Mc Conkey agar, Difco; 0,6 ml/plate) supplemented with 10 μg/ml of tetracycline (Sigma). The plates are incubated at 37° C. for 12–17 hrs. About 5600 tetracycline resistant colonies of transformed *E.coli* HB 101 are prepared.

Figure 2:
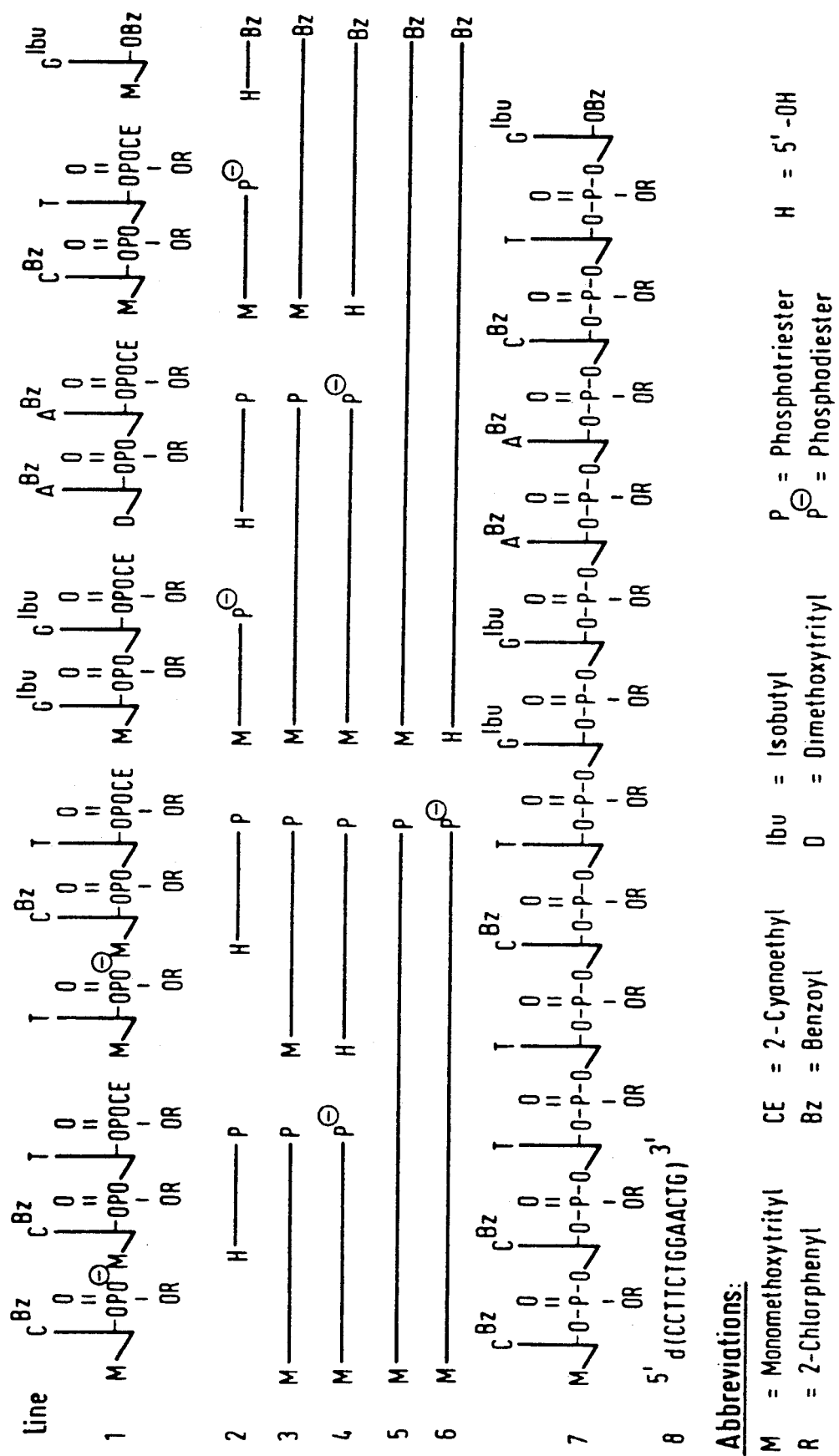
FIG. 2 shows synthesis of DNA primers.

5. Identification of clones containing HuIFN cDNA a) Synthesis of a 13-mer oligodeoxynucleotide primer (FIG. 2)

Figure 3:
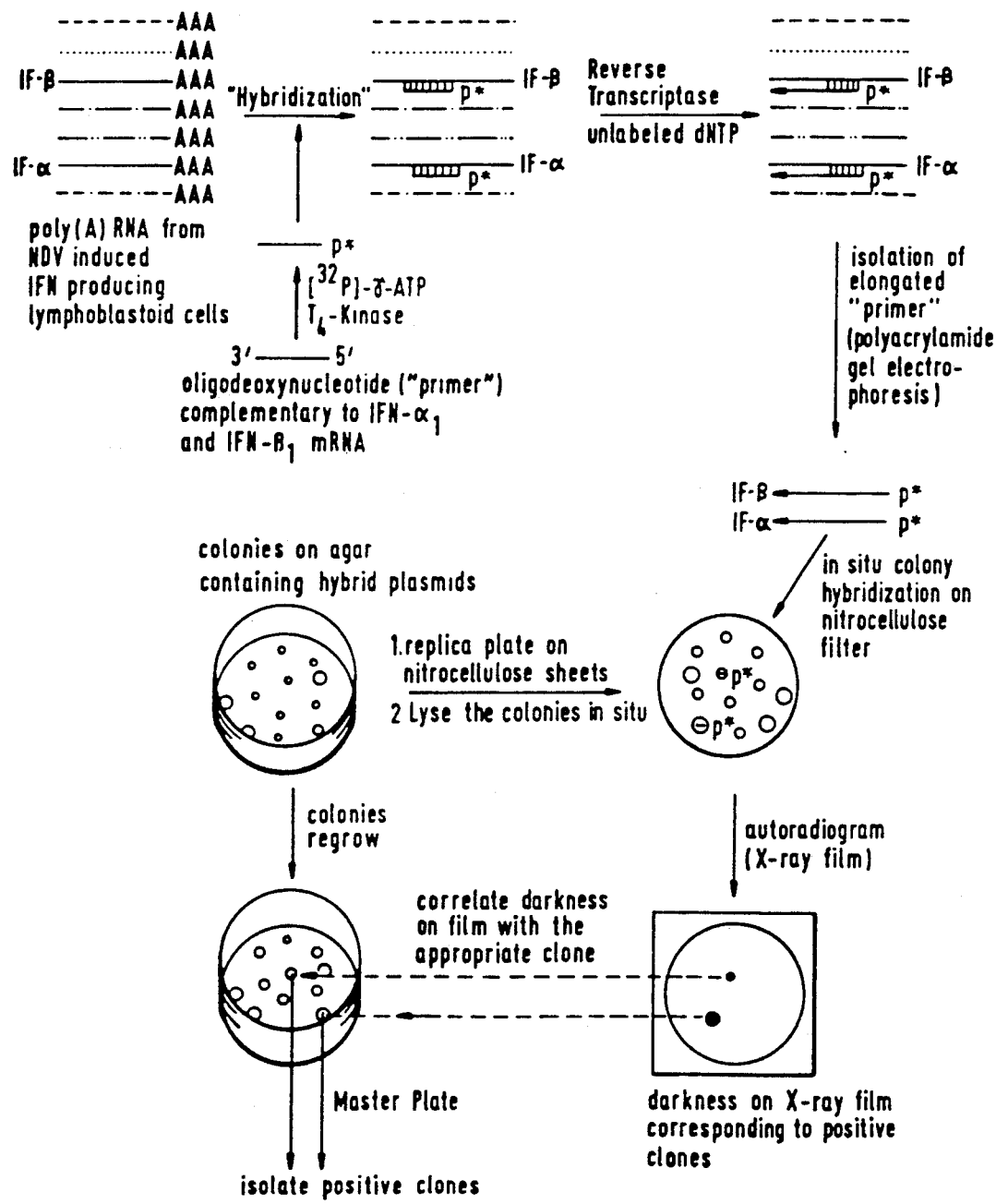
FIG. 3 shows synthesis of HuIFN-β and HuIFN-α specific probes and their use.

An oligodeoxynucleotide complementary to a stretch of 13 nucleotides which both HuIFN-α₁ and HuIFN-β mRNA share in common is chemically synthesized by the phosphotriester method (cf. Itakura et al. (38), de Rooij et al (39)). The individual steps of the synthesis are outlined in FIG. 2. The starting materials indicated in line 1 of FIG. 2 (mono- and dideoxynucleotides carrying protective groups) are known from the literature The protective groups are split off by the methods described by Itakura et al.: the deblocking of 5'-monomethoxytrityl (M) or dimethoxytrityl (D) substituted hydroxyl groups is performed with acetic acid (80%) at room temperature, and the β-cyanoethyl phosphate groups are cleaved with 0.1N sodium hydroxide in dioxane-water (4:1) at room temperature. The condensation of the building blocks is accomplished by using triisopropylbenzenesulfonyl chloride as an activating agent to afford oligodeoxynucleotides up to the fully protected 13-mer primer represented in line 7 of FIG. 2. The last step (complete removal of all protective groups) is achieved in the following manner:

A solution containing 64.6 mg of the fully protected 13-mer oligodeoxynucleotide in 3 ml dioxane and 1 ml acetonitrile is treated with 200 mg syn-p-nitrobenzaldoxime and 124 mg $N^1,N^1,N^3,N^3$-tetramethylguanidine and allowed to stand for 27 hours. 10 ml ammonia (25%) is added and the solution is stored for 24 hours at 50° C. After the solvent has been evaporated in vacuo, the residue is dissolved in water, adjusted to pH 4 with acetic acid and the solution is extracted 20 times with chloroform. The aqueous solution is evaporated in vacuo and the residue is dissolved in 1 ml acetic acid (80%). The solution is allowed to stand for 1 hour, diluted with 6 ml water, extracted 3 times with chloroform and lyophilized. The third part of the raw product obtained is purified by chromatography on DEAE-Sephadex A 25 (column size: 10·1.3 cm) through a 200 ml 0.2–1.2M triethylammonium bicarbonate gradient. Elution of the main fraction occurs at a gradient concentration of 0.87M. The main fraction, which consists of the pure product as indicated by a HPLC test, is evaporated 3 times with water, filtered through 10 ml Dowex 50W (NH$_4$-salt) and lyophilized. HPLC (permaphase AAX, column size 90·0.3 cm, 60° C., 2 ml/min; gradient A=0.005M KH$_2$PO$_4$, B=0.5M KH$_2$PO$_4$, 0.5M KCl, pH 4.5; 20% A→100% B in 30 min): t$_R$ 11.8 min.

b) Preparation of a $^{32}$P-labeled human IFN-α and IFN-β specific cDNA probe (FIG. 3)

40 pmol of the synthetic 13-mer oligodeoxynucleotide primer (cf. step 5a) and 40 pmol of [γ-$^{32}$P]-ATP (5,700 Ci·mmol$^{-1}$, Amersham) are combined in 100 μl of 50 mM Tris·HCl (pH 9.5), 10 mM MgCl$_2$ and 5 mM DTT. 50 units of T$_4$ polynucleotide kinase (P-L Biochemicals) are added and after 30 min at 37° C. additional 20 units of the enzyme are added, and incubation is continued for another 15 min at 37° C. The aqueous solution containing the $^{32}$P-labeled primer is purified by phenol extraction. Further purification is accomplished by chromatography on a 4 ml Sephadex G-50 (Pharmacia, fine) column in 1 mM Tris·HCl (pH 8.0). 0.1 ml fractions are collected. The radioactivity of each fraction is determined by measuring the Cerenkov radiation. A specific activity of 4·10$^6$ Cerenkov cpm per pmole of oligodeoxynucleotide is obtained. The $^{32}$P-labeled primer (40 pmol) is lyophilized, resuspended in 91 μl of H$_2$O containing 14 μg of poly(A) RNA (from induced Namalwa cells, prepared as described in step 1) and heated for 60 sec at 100° C. 9 μl of 4M KCl is added and the mixture is incubated at 25° C. for 60 minutes. 450 μl reverse transcriptase mix is added such that the reaction volume comprises 40 mM Tris·HCl (pH 8), 4 mM MgCl$_2$, 1 mM DTT (Calbiochem, Inc.), 74 mM KCl, 1 mM each of dATP, dGTP, dCTP, dTTP (P-L Biochemicals) and 90 units of avian myeloblastosis virus (AMV) reverse transcriptase. The incubation is continued for 1 h at 37° C. The solution is extracted with 1 volume of phenol (saturated in TNE) and the nucleic acids are precipitated with 2 volumes of ethanol at −20° C. for 10 h. The precipitate is collected by centrifugation(HB-4 rotor, 20 min, 10,000 rpm, 0° C.) and dissolved in 20 μl dye mix containing 90% (v/v) formamide (Merck, pro analysis), 1 mM EDTA, 0.05% bromo.phenol blue and 0.05% xylene cyanol blue. The sample is heated at 90° C. for 2 min and applied on a 5% polyacrylamide gel in Tris-borate-EDTA(cf.Peacock et al. (32). A single band is visible on the autoradiogram which migrates between the 267 bp and 435 bp $^{32}$P-labeled marker DNA fragments obtained from the Hae III digest of the plasmid pBR 322. The $^{32}$P-labeled cDNA fragment is extracted from the gel and purified as described by Mueller et al. (47). 20,000 Cerenkov cpm of the $^{32}$P-labeled human IFN-α and IFN-β specific cDNA probe are obtained c) Screening for colonies containing HuIFN cDNA (FIG. 3)

1650 of the transformant colonies prepared as described above (step 4) are transferred to nitrocellulose filters BA 85 (Schleicher & Schuell, 8 cm diameter). The cells are lysed and their DNA is denatured and fixed to the filters in situ, according to Grunstein and Hogness (36). The filters bearing the colonies are prehybridized in 4×SET (a solution containing 0.15M NaCl, 30 mM Tris·HCl (pH 8.0), 1 mM EDTA) 0.1% (w/v) Ficoll 400 (Pharmacia), 0.1% (w/v) polyvinylpyrrolidone (PVP-360, Sigma), 0.1% (v/v) BSA, 0.5% SDS, 50 μg/ml denatured calf-thymus DNA (prepared as follows: 5 mg calf-thymus DNA (type I, Sigma) is boiled for 10 min in 0.5M NaOH to shear the DNA, neutralized with 5M acetic acid and precipitated with 2 volumes of ethanol at −20° C. The precipitate is collected by centrifugation in a HB-4 rotor for 10 min at 0° C. and redissolved in 500 μl 0.5 mM EDTA) at 65° C. for 4 h using 20 ml mixtures per filter and hybridized with 10$^3$ Cerenkov cpm of the $^{32}$P-labeled probe per nitrocellulose filter in 5×SET, 0.02% (w/v) Ficoll, 0.01% polyvinylpyrrolidone, 0.02% (v/v) BSA, 0.2% SDS and 50 μg/ml denatured calf-thymus DNA. The hybridization is performed at 65° C. for 36 h.

The filters are rinsed once in chloroform, twice in SET, 0.5% SDS at room temperature and twice in SET, 0.5% SDS for 1 h at 60° C. and once with 3 mM Trizma base at room temperature for 1 h. The filters are dried by blotting on 3 MM-paper (Whatman), and an X-ray film (Fuji) is exposed to the filters using a screen (Ilford intensifying screen) at −80° C. for 72 h.

Nine positive colonies are identified on the autoradiogram and are used for further investigation.

Since the primary clones of transformed cells occasionally contain more than one species of recombinant DNA molecules, the hybrid plasmid DNAs are isolated from the 9 positively hybridizing clones and used to retransform E. coli HB 101 as described before.

The hybrid plasmid DNA is isolated as follows: 1 colony is used to inoculate 10 ml of tryptone medium, supplemented with 10 μg/ml of tetracycline as above in a 25 ml Erlenmeyer flask. The culture is shaken for 15-18 hrs at 37° C. at 300 rpm. The cells are harvested by centrifugation (Sorvall, HS-4 rotor, 10 min at 4,000 rpm, 4° C.). About 0.1 g of cells are obtained and are resuspended in 1 ml 50 mM Tris·HCl (pH 8.0). 0.25 ml of lysozyme solution (10 mg/ml in 50 mM Tris·HCl (pH 8.0),lysozyme is purchased from Sigma) ,are added and after incubation at 0° C. for 10 min, 0.15 ml of 0.5M EDTA (pH 7.5) is added. After another 10 min at 0° C., 60 μl of 2% Triton X-100 (Merck) is added. After 30 min at 0° C., the sample is centrifuged for 30 min at 15,000 rpm and 4° C. in a Sorvall SA-600 rotor. The supernatant is deproteinized with 1 volume of phenol (saturated in TNE). The phases are separated by centrifugation (Sorvall HB-4 rotor) for 10 min at 5,000 rpm at 4° C. The upper phase is extracted twice with 1 volume of chloroform. Pancreatic RNAse A (Sigma; 10 mg/ml in TNE, preheated 10 min at 85° C.) is added to a final concentration of 25 μg/ml and the mixture is incubated for 40 min at 37° C. The solution is then adjusted to 1M NaCl and 10% polyethylene glycol 6000 (Fluka, autoclaved for 20 min at 120° C.) and incubated at −10° C. for 2 hrs. The precipitate is collected in a Sorvall HB-4 rotor (20 min at 10,000 rpm, 0° C.) and redissolved in 100 μl of TNE. The DNA solution is extracted with 1 volume of phenol and the DNA is precipitated with 2 volumes of ethanol at −80° C. for 10 min.

The precipitate is collected by centrifugation in an Eppendorf centrifuge and the DNA is redissolved in 20 μl of 10 mM Tris·HCl (pH 7.5) and 0.5 mM EDTA. 8-10 μg of hybrid plasmid DNA are recovered from a 10 ml culture.

*E coli* HB 101 is transformed with each of the nine isolated hybrid DNAs and the transformed cells are plated on agar plates containing tetracycline, as described before (step 4). From each transformation, 3 tetracycline resistant clones are picked, 10 ml cultures are prepared and the hybrid DNAs are isolated from the cultures as described before.

All the DNA samples before and after retransformation are analyzed by cleavage with Pst I endonuclease and electrophoresis through a 1% agarose gel in 50 mM Tris-acetate (pH 7.8) and 1 mM EDTA. All the samples display identical cleavage patterns before and after retransformation.

One of the recloned recombinant DNA molecules gives 2 bands, one with the mobility of Pst I-cleaved pBR 322, the other with a mobility corresponding to about 1,000 bp. It is denoted CG-pBR 322/HLycIFN-1'b.

Another recombinant DNA gives 3 bands, one with the mobility of Pst I-cleaved pBR 322, one with a mobility of about 600 bp and one with a mobility of about 150 bp. The recombinant DNA molecule in this clone is designated CG-pBR 322/HLycIFN-$\beta_1$.

d. Characterization of the clones CG-pBR 322/HLycIFN-1'b and CG-pBR 322/HLycIFN-$\beta_1$ The recombinant plasmid DNAs of the clones CG-pBR 322/HLycIFN-1'b and CG-pBR 322/HLycIFN-$\beta_1$ are isolated from the cultures as described above (step 5c) and characterized by establishing the nucleotide sequence of the cDNA insert using the method described by Maxam and Gilbert (41) Basically, the following approach is used:

The isolated recombinant plasmid DNA is digested with various restriction endonucleases. The enzymes are applied essentially as described by the supplier (New England Biolabs),except that BSA is replaced by gelatin in the enzyme buffers The solution containing the restricted DNA is deproteinized with phenol (saturated with TNE) The DNA is precipitated with ethanol, redissolved in 50 mM Tris-HCl (pH 8.0) at a DNA concentration of 50 μg/ml and incubated with 0.1 units of calf intestinal alkaline phosphatase (Boehringer) perpmole DNA 5' ends for 30 min at 37° C. The enzyme is inactivated by heating the solution for 60 min at 65° C. The DNA is purified by DEAE-cellulose chromatography as described by Mueller et al.(47) and precipitated with ethanol. The DNA is then 5'-terminally labeled with [γ-$^{32}$P]-ATP (>5,000 Ci/mmole, Amersham) and T4 polynucleotide Kinase (P-L Biochemicals) essentially as described by Maxam and Gilbert (41) except that the DNA is not denatured before the Kinase reaction In general, the specific activities amount to 1-3·10$^6$ cpm/pmole 5'-ends.

The labeled DNA fragments are cleaved with a second restriction endonuclease and the products are separated by electrophoresis through a 6%, 8% or 10% polyacrylamide gel in Tris-borate-EDTA buffer. The DNA fragments are extracted from the gel and purified as described by Mueller et al. (47). For the determination of the nucleotide sequences, the DNA fragments are chemically degraded and the products are separated by polyacrylamide gel electrophoresis as described by Maxam and Gilbert (41).

In particular, the isolated plasmid DNAsof the clone CG-pBR 322/HLycIFN-1'b are treated as follows. On the one hand, 5 μg of the plasmid DNA is digested with Bgl II, 5' terminally labeled, and cleaved with Pvu II. The Pvu II-Bgl II* (*indicates the labeled site) and Bgl II- Pvu II* DNA fragments are isolated on a 6% polyacrylamide gel. On the other hand, 5 μg of the plasmid is digested with Alu I, 5'-terminally labeled, and cleaved with Pst I. The Pst I - Alu I* DNA fragment is isolated on a 8% polyacrylamide gel. The individual fragments are subsequently degraded and sequenced according to Maxam and Gilbert. The nucleotide sequence obtained is depicted in FIG. 4. A stretch of about 25-35 deoxyguanosine residues is preceding at the 5'-end of the cDNA insert. The nucleotide sequence shown is somewhat similar to that of IFN-α (type F) cDNA described by Goeddel et al. [(14), cf. also Weissmann (3)], nevertheless displaying a lot of distinct deviations (point mutations) some of which are affecting the resulting aminoacids (cf. FIG. 4).

The isolated plasmid DNA of the clone CG-pBR 322/HLycIFN-$\beta_1$ is treated in a similar manner. 5 μg of the plasmid is digested with Pvu II and 5'-terminally labeled. One half of the mixture is cleaved with Pst I, and the rest with Bgl II. The Pst I-Pvu II* and Bgl II-Pvu II* fragments are isolated by electrophoresis on a 6% polyacrylamide gel and degraded as mentioned above. The nucleotide sequence (N-terminal sequence) is depicted in FIG. 5 and reveals that the cDNA insert starts at nucleotide number 102 of the IFN-$\beta_1$ cDNA as described by Taniguchi et al. (17). Therefore, the cDNA insert has the capacity to code for human IFN-$\beta_1$ lacking 11 amino acids at the N-terminus. The cDNA insert is flanked at its 5' end by a stretchof about 20-25 deoxyguanosine residues and shows a point mutation at position 153, converting a C to a T residue without affecting the resulting amino acid.

e. Identification of clones containing recombinant DNA molecules cross-hybridizing to the inserts of CG-pBR 322/HLycIFN-1'b and CG-pBR 322/HLycIFN-$\beta_1$ The recombinant plasmid DNAs of the clones CG-pBR 322/HLycIFN-1'b and CG-pBR 322/HLycIFN-$\beta_1$ are isolated from the cultures as described above (step 5c). The CG-pBR 322/HLycIFN-1'b plasmid DNA (5 μg) is digested with Bgl II, 5' terminally labeled, and cleaved with Pvu II. On the other hand, the isolated CG-pBR 322/HLycIFN-β plasmid DNA (5 μg) is digested with Pvu II, 5'-terminally labeled, and cleaved with Bgl II. The Pvu II-Bgl II* (351 bp) DNA fragment (probe A) and the Pvu II*-Bgl II (368 bp) DNA fragment (probe B) are isolated from a 8% polyacrylamide gel as described above (step 5d) and used for in situ colony hybridization (see below). The restriction of the plasmid DNAs, the labeling, and the purification of the DNA fragments are accomplished in the same manner as described above (step 5d).

4,000 of the transformant colonies prepared as described above (step 4) are transferred to nitrocellulose filters BA 85 (Schleicher & Schuell, 8 cm diameter). The cells are lysed and their DNA is denatured and fixed to the filters in situ, according to Grunstein and Hogness (36). Hybridizations to the probes A and B (both probes are mixed) are performed as described before (step 5c). 6 positive colonies are identified by autoradiography, 3 of which, designated E. coli HB 101 CG-pBR 322/HLycIFN-$4_1$,
E. coli HB 101 CG-pBR 322/HLycIFN-$5_1$ and
E. coli HB 101 CG-pBR 322/HLycIFN-$8'_1$ are used for further investigation. The plasmid DNAs of these clones are isolated, retransformed, and reisolated as described above (step 5c, 5d).

In order to establish the nature of the inserts of the recombinant DNAs, the nucleotide sequences of the cDNA inserts (partial or complete) are established by using the general approach as described above (step 5d).

In particular, 5 μg of the isolated plasmid DNAs CG-pBR 322/HLycIFN-$4_1$ and CG-pBR 322/HLycIFN-$8'_1$ are each digested with Pvu II, 5'-terminally labeled and cleaved with Pst I. The DNA fragments are fractionated on a 8% polyacrylamide gel and the Pst I-Pvu II* (~120 bp) from $8'_1$ DNA and Pst I-Pvu II* (82 bp) from $4_1$ DNA are isolated as usual.

The isolated plasmid DNA CG-pBR 322/HLycIFN-$5_1$ is treated as follows. On the one hand, 5 μg of the plasmid DNA is digested with Hae III, 5'-terminally labeled and cleaved with Pst I. The Pst I-Hae III* (57 bp) DNA fragment is isolated on a 10% polyacrylamide gel. On the other hand, 5 μg of the plasmid is digested with EcoR I, 5'-terminally labeled and cleaved with Pst I. The Pst I-EcoR I* (235 bp) and EcoR I*-Pst I (~700 bp) DNA fragments are isolated on a 8% polyacrylamide gel. The various DNA fragments are subjected to sequence analysis according to Maxam and Gilbert (41).

The nucleotide sequences of the cDNA inserts are depicted in FIGS. 6-8. In FIG. 6, the nucleotide sequence of the cDNA insert of CG-pBR 322/HLycIFN-$4_1$ is shown. The insert is flanked at the 5' end by a stretch of 23 deoxyguanosine residues and comprises part of the IFN-$α_2$ (Le) cDNA described by Streuli et al. (12). In the 3'-extracistronic region, thereare some minor deviations (point mutations) and a stretch of additional 318 nucleotides.The nucleotide sequence of the cDNA insert of CG-pBR322/HLycIFN-$8'_1$ is depicted in FIG. 7. The insert is flanked at the 5' end by a stretch of 20-23 deoxyguanosine residues and is similar but not identical, to the IFN-α (type D) cDNA described by Goeddel et al.[(14); cf. also Mantei et al. (11)]. Apart from differences in the cDNA regions preceding and following the IFN coding sequence, the IFN gene contains at positions 28-30 a GCC triplet and at positions 409-411 a GCG triplet coding for alanine instead of GTC and GTG, respectively, coding for valine. Finally, the nucleotide sequence ofthe cDNA insert of CG-pBR 322/HLyc IFN-$5_1$ (see FIG. 8) reveals a stretch of 17 deoxyguanosine residues at the 5' end The nucleotide sequenceisrelated tothatof IFN-α (type B) cDNA describedbyGoeddeletal. (14). However, thereare additional nucleotides at the 5' end of the cDNA insert of HLycIFN-$5_1$, point mutations, excisions and insertions in the extracistronic region and in the IFN coding sequence, especially at positions 22 and 361-372, are evident as well.

6. Synthesis of human interferons by E. coli containing human IFN-specific recombinant DNA molecules The 5 clones which have been shown to contain human IFN specific recombinant DNA molecules, namely E. coli HB 101 CG-pBR 322/HLycIFN-1'b
E. coli HB 101 CG-pBR 322/HLycIFN-$4_1$,
E. coli HB 101 CG-pBR 322/HLycIFN-$5_1$,
E. coli HB 101 CG-pBR 322/HLycIFN-$8'_1$, and
E. coli HB 101 CG-pBR 322/HLycIFN-$β_1$, are tested for IFN activity, which, in each case, is accomplished in the following manner:

Cultures of the corresponding E. coli clone (30 ml suspensions) are grown in tryptone medium to an optical density (OD$_{650}$) of about 1. The cells are harvested and resuspended in 0.5 ml of an aqueous solution containing 30 mM NaCl and 50 mM Tris-HCl (pH 8.0). Lysozyme (Sigma) is added to 1 mg/ml. After 30 min at 0° C., the suspensions are frozen (liquid nitrogen) and thawed (at 37° C.) 5 times, and centrifuged for 20 min at 20,000 rpm in a SS 34 Sorvall rotor at 4° C. The supernatants are assayed for IFN activity using the cythopathic bioassay according to Armstrong (29) as described in step 1c. The following activities are found:

| Source of extract<br>E. coli HB 101 containing recombinant DNA | IFN activity<br>(IU/ml) |
| --- | --- |
| CG-pBR 322/HLycIFN-1'b | 0;0 |
| CG-pBR 322/HLycIFN-$4_1$ | 0;0 |
| CG-pBR 322/HLycIFN-$5_1$ | 10 000;10 000 |
| CG-pBR 322/HLycIFN-$8'_1$ | 100;100 |
| CG-pBR 322/HLycIFN-$β_1$ | 0;0 |

Possibly, clones exhibiting no measurable IFN activities contain recombinant DNAs in which the HuLyIFN-cDNA insert is in an improper orientation in regard to the direction of transcription. Therefore, the recombinant DNA of one such clone (CG-pBR 322/HLycIFN-1'b) containing a full length cDNA insert is reoriented as follows: The plasmid DNA of the clone E. coli HB 101 CG-pBR 322/HLycIFN-1'b is isolated as described above (step 5c) and cleaved with Pst I. 0.5 μg of the cleaved DNA in 20 μl of a buffer mixture, containing 20 mM Tris-HCl (pH 7.8), 10 mM MgCl$_2$, 10 mM DTT, 25 mM NaCl and 50 μg/ml gelatin, is treated with 0.2 units of T4 DNA ligase (Biolabs) and 0.5 mM ATP for 2 h at 15° C. E. coli HB 101 is transformed with the cDNA mixture as described above (step 4). Transformed colonies are selected on Mc Conkey agar plates supplemented with tetracycline and, subsequently, replica-plated to nitrocellulose filters. 4 bacterial colonies hybridizing to the $^{32}$P-labeled Pvu II-Bgl II* fragment (351 bp) of the recombinant DNA CG-pBR 322/HLycIFN-1'b (cf. step 5e) are designated E. coli HB 101 CG-pBR 322/HLycIFN-1'b to -1'b₄. Extracts of the 4 clones are prepared and tested for IFN activity as described above. The following activities are found:

| Source of extract<br>E. coli HB 101 containing recombinant DNA | IFN activity<br>(IU/ml) |
|---|---|
| CG-pBR 322/HLycIFN-1'b₁ | 0;0 |
| CG-pBR 322/HLycIFN-1'b₂ | 0;0 |
| CG-pBR 322/HLycIFN-1'b₃ | 0;0 |
| CG-pBR 322/HLycIFN-1'b₄ | 30;30 |

Hence, the plasmid CG-pBR 322/HLycIFN-1'b₄ contains a cDNA insert capable of directing the synthesis of a polypeptide with IFN activity.

Figure 9:
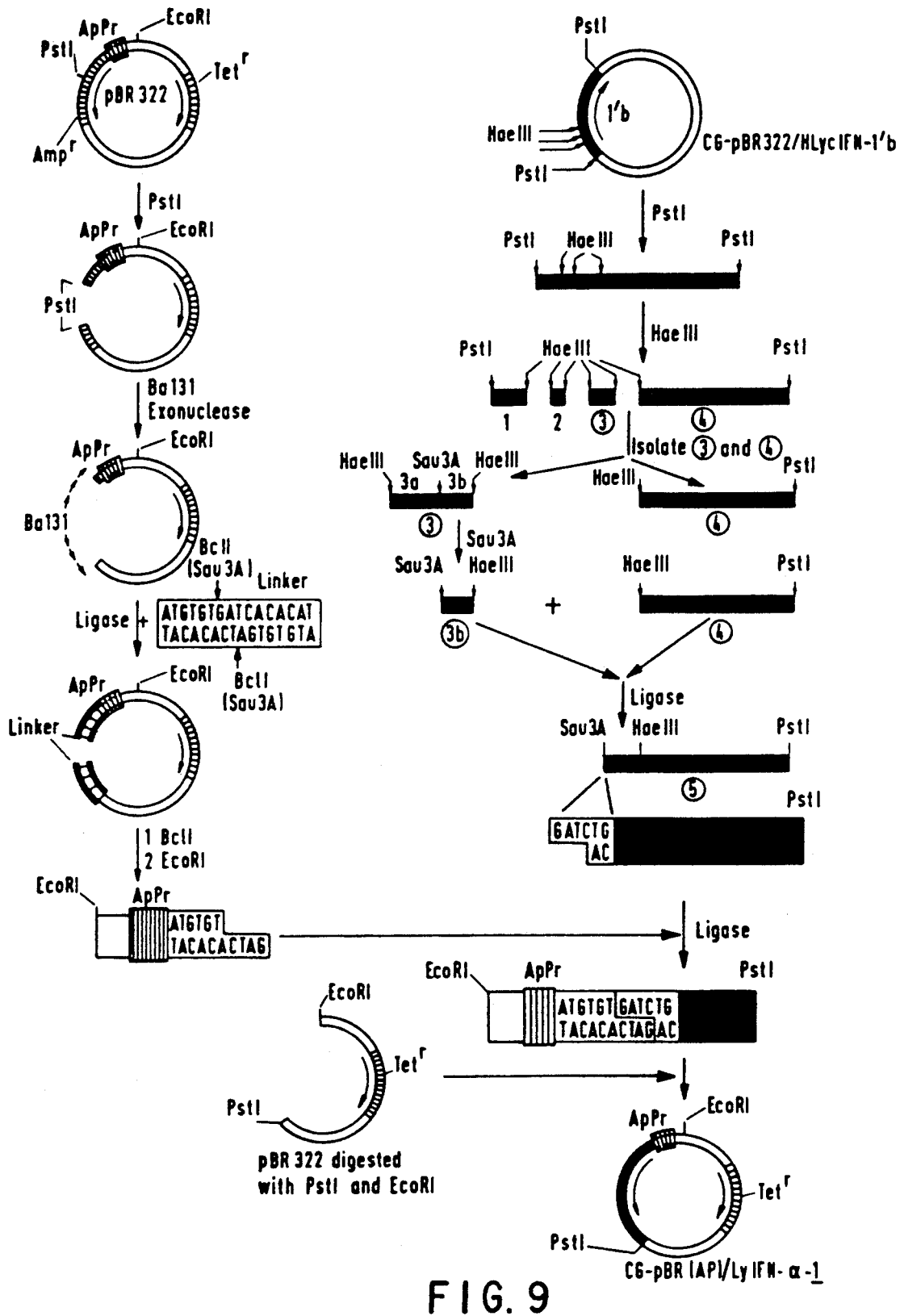
FIG. 9 shows the construction of CG-pBR(AP)-/LyIFN-$\alpha$-1.

7. Construction of recombinant plasmids capable of producing high levels of polypeptides with IFN activity and transformation of E. coli HB 101 with these plasmids A. Construction of CG-pBR (AP)/LyIFN-α-1 recombinant plasmid In order to improve the IFN specific protein yield of the clone E. coli HB 101 CG-pBR 322/HLycIFN-1'b, the following construction is performed as indicated schematically in FIG. 9.

a. Preparation of the cDNA insert

The recombinant plasmid DNA (150 μg) of the clone E. coli HB 101 CG-pBR 322/HLycIFN-1'b is cleaved with Pst I (Biolabs) using standard procedures (cf step 5d) Following phenol extraction and ethanol precipitation, the excised insert is isolated by means of sucrose density gradient centrifugation (5–23%) in 50 mM Tris-HCl (pH 8.0) and 1 mM EDTA. The centrifugation is performed at 35,000 rpm in a TST 41 rotor (Kontron AG) at 15° C. for 16 h. 0.3 ml fractions are collected with an ISCO gradient collector at 1 ml/min. The fractions containing the small fragment (i.e. the insert) are pooled. The DNA is precipitated with ethanol as usual, and the precipitate is collected by centrifugation in a HB-4 rotor (Sorvall) at 10,000 rpm at 0° C. for 10 min. The precipitate is redissolved in 60 μl 10 mM Tris-HCl (pH 7.5) and 0.05 mM EDTA. 30 μg DNA are recovered as determined by measuring the optical density.

The insert DNA (10 μg) is digested with Hae III (Biolabs) and the fragments are fractionated on a 2% agarose gel in a solution containing 50 mM Tris, 50 mM boric acid, 1 mM EDTA and 0.5 μg/ml ethidium bromide. The largest DNA fragments, Hae III-Pst I (869 bp) and Hae III-Hae III (82 bp, cf. FIG. 9, fragments 3 and 4 respectively), are each excised from the gel, squirted through a thin needle with a syringe into 5 ml of 0.15M NaCl, 50 mM Tris-HCl (pH 8.0), 1 mM EDTA, and eluted overnight by shaking. The eluate is passed through a 100 μl DE-52 (Whatman) Pasteur-pipette column to adsorb the DNA. The column is washed with 2 ml of the same buffer and the DNA is eluted with 400 μl of a solution containing 1.5M NaCl, 50 mM Tris (pH 8.0) and 1 mM EDTA. The DNA is precipitated with 2 volumes of ethanol at −20° C. overnight. The precipitate is collected by centrifugation in an Eppendorf centrifuge.

The Hae III-Hae III DNA fragment (82 bp) is redissolved and digested with Sau 3A (Biolabs). The enzyme is heat-inactivated at 65° C. for 30 min. 1 μg of the Hae III-Pst I DNA fragment (869 bp) is added, the solution is adjusted to 10 mM MgCl₂, 10 mM DTT and 0.5 mM ATP, and T4 DNA ligase (Biolabs) is added to 30 units/μl reaction volume. The solution is incubated for 10 h at 15° C. Following extraction with phenol and chloroform, the mixture is fractionated on a 2% agarose gel in Tris-borate-EDTA in the presence of ethidium bromide. The Sau 3A-Pst I DNA fragment (cf. FIG. 9, fragment 5) is extracted as described before, precipitated with ethanol and redissolved in 10 μl of a solution containing 10 mM Tris·HCl (pH 7.5) and 0.05 mM EDTA.

b. Preparation of the DNA fragment containing the β-lactamase regulatory region (ApPr) of pBR 322

The plasmid pBR 322 is cleaved with Pst I (cf. step 3b) and treated with 4 units/ml of the exonuclease Bal 31 (Bethesda Research Lab.) at 30° C. for 4–10 min to remove the β-lactamase coding segment.

A chemical DNA linker of the formula

5'-ATGTGTGATCACACAT-3' is synthesized using the method described above (step 5a). The linker is added to the Bal 31 treated pBR 322 DNA by conventional ligating. The resulting hybrid molecule is cleaved with the restriction endonucleases Bcl I (Biolabs) and EcoR I. The digestion products are fractionated on a 8% polyacrylamide gel in Tris-borate-EDTA as described before (step 2a). DNA fragments (ApPr DNA fragments), migrating between 184 bp and 234 bp marker DNAs, are isolated as described above (step 7aA),and precipitated with ethanol as usual. The precipitate is redissolved in a solution containing 10 mM Tris·HCl (pH 7.5) and 0.05 mM EDTA.

c. Ligation of the ApPr DNA fragment to the cDNA insert and preparation of the plasmid CG-pBR(AP)/LyIFN-α-1

The solutions containing the ApPr DNA fragments and the cDNA insert are pooled. The mixture is adjusted to 10 mM MgCl₂, 10 mM DTT and 0.5 mM ATP, and incubated with 30 units/μl T4 DNA ligase (Biolabs) at 15° C. for 12 h. Following extraction with phenol and chloroform, the mixture is fractionated on a 1% low melting agarose gel (Biorad). The obtained ApPr-cDNA fragment is joined to the large fragment of pBR 322 cleaved with both Pst I (Biolabs) and EcoR I (Biolabs) in the following manner The gel piece, containing the ApPr cDNA fragment (about 20 μl ) is mixed with the Pst I-EcoR I fragment of pBR 322, melted at 65° C. for 2 min,cooled to 37° C., adjusted to 0.5 mM ATP, 10 mM DTT and 10 mM MgCl₂, and incubated with 30 units/μl of T4 DNA ligase (Biolabs) for 12 h at 15° C. to give a solution containing the recombinant plasmid named CG-pBR(AP)/LyIFN-α-1.

d. Transformation of E. coli HB 101 with the plasmid CG-pBR(Ap)/LyIFN-α-1

One tenth volume of a solution containing 100 mM Tris·HCl (pH 7.5), 100 mM CaCl₂ and 100 mM MgCl₂, is added to the solution containing the plasmid CG-pBR (AP)/LyIFN-α-1. The combined solutions are heated for 10 min at 65° C. to inactivate the ligase and cooled to 37° C. The solution is then taken to transform Ca²⁺-treated E. coli HB 101 as described above (step 4) and plated onto Mc Conkey agar plates supplemented with 10 μg/ml tetracycline. The transformed colonies are screened for IFN activity (cf. step 6). The clone synthesizing the highest level of IFN activity is selected and designated E. coli HB 101 CG-pBR(AP)/LyIFN-α-1. An activity of 40,000 (IU/ml) is found which represents a 1300 fold stimulation compared to the original clone E. coli HB 101 CG-pBR322/HLycIFN-1'b.

The recombinant plasmid DNA of the clone CG-pBR (AP)/LyIFN-α-1 is isolated from the culture as described above (step 5c) and characterized by establishing the nucleotide sequence of the cDNA insert (IFN gene) and the β-lactamase regulatory region. The result is summarized in FIG. 10.

B. Construction of the recombinant plasmid CG-pBR (AP)/LyIFN-α-3

Figure 11:
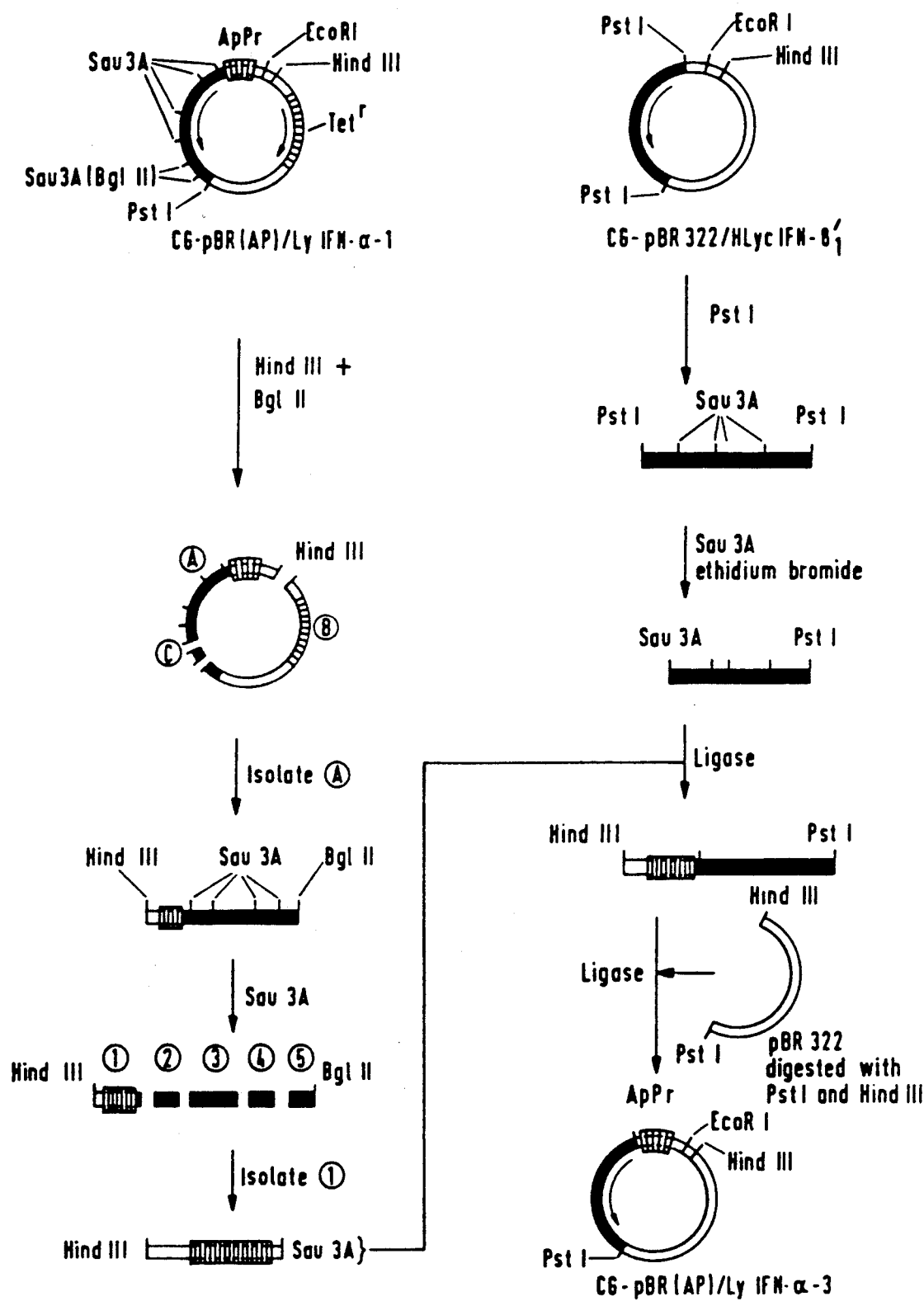
FIG. 11 shows the construction of CG-pBR(AP)-/LyIFN-$\alpha$-3.

The IFN specific protein yields of the clone E. coli HB 101 CG-pBR 322/ HLycIFN-8'$_1$ is improved as follows (cf. FIG. 11):

a. Preparation of the DNA fragment containing the β-lactamase regulatory region from CG-pBR (AP)/LyIFN-α-1

CG-pBR (AP)/LyIFN-α-1 DNA (100 μg) is cleaved with Hind III (Biolabs) and Bgl II (Biolabs). Following phenol extraction and ethanol precipitation, the excised DNA fragment is isolated by means of sucrose density gradient centrifugation (5–23%) in 50 mM Tris-HCl (pH 8.0) and 1 mM EDTA. The centrifugation is performed at 58,000 rpm in a TST60 rotor (Kontron AG) at 15° C. for 4 hours. 0.2 ml fractions are collected as described before. The fractions containing the small fragment (Hind III-Bgl II) are pooled and the DNA is precipitated with ethanol as usual. The precipitate is redissolved in 80 μl 10 mM Tris-HCl (pH 7.5) and 0.05 mM EDTA. 16 μg DNA are recovered as determined by measuring the optical density.

The DNA fragment (Hind III-Bgl II) (4 μg) is cleaved with Sau 3A (Biolabs) and the digestion products are fractionated on a 6% polyacrylamide gel in Tris-borate-EDTA as described before. The DNA fragments are stained in EtBr (0.5 μg/ml), the Hind III-Sau 3A DNA fragment (239 bp) is extracted and isolated as before. The DNA is precipitated with ethanol as usual. The precipitate is redissolved in 20 μl 10 mM Tris-HCl (pH 7.5) and 0.05 mM EDTA.

b. Preparation of the cDNA insert

The cDNA insert is excised from the recombinant plasmid CG-pBR 322/HLycIFN-8'$_1$ with Pst I as described above (section 7aA).

The cDNA insert (2 μg) is digested with 2.5 units of Sau 3A (Biolabs) in 10 μg/ml EtBr and incubated at 37° C. for 60 min. The digests are phenol extracted and the DNA is precipitated in ethanol as above. The DNA fragments are fractionated on a 1.2% agarose gel in a solution containing 50 mM Tris, 50 mM boric acid, 1 mM EDTA and 0.5 μg/ml ethidium bromide.

The second largest DNA (Sau 3A-PstI 693 bp) is extracted from the gel and purified as described in section 7aA). The DNA is redissolved in 20 μl 10 mM Tris-HCl (pH 7.5) and 0.05 mM EDTA.

c. Ligation of the Hind III-Sau 3A DNA fragment to the cDNA insert (Sau 3A-PstI)

Equal amounts of both DNA fragments (~50 ng) are incubated in a solution containing 10 mM MgCl$_2$, 10 mM DTT, 0.5 mM ATP and 30 units/μl T4 DNA ligase (Biolabs) at 15° C. for 3 hours. The mixture is incubated for 15 min. at 80° C. and adjusted to 50 mM NaCl. The DNA mixture is digested with 0.5 units PstI (Biolabs) and 1 unit Hind III (Biolabs) for 20 min at 37° C. The DNA is phenol extracted, ethanol precipitated and redissolved in 20 μl 10 mM Tris-HCl (pH 7.5) and 0.05 mM EDTA.

One half of the resulting mixture is ligated to the large Hind III-PstI DNA fragment of the plasmid pBR 322 (~100 ng) in 10 mM MgCl$_2$, 10 mM DTT, 0.5 mM ATP containing 30 units/μl of T4 DNA ligase (Biolabs) for 2 h at 15° C. to give a solution containing the recombinant plasmid CG-pBR(AP)/LyIFN-α-3.

d. Transformation of E. coli HB 101 with the plasmid CG-pBR(AP)/LyIFN-α-3

One tenth volume of the above solution is used to transform E.coli HB 101 as described in step 4). The transformed colonies are used to test for IFN activity as described earlier (cf. step 6).

The clone synthesizing the highest level of IFN activity is selected and designated E. coli HB 101 CG-pBR (AP)/LyIFN-α-3.

The IFN activity is determined as described above (step 6). An activity of 70,000 (IU/ml) is found which represents a 700 fold stimulation compared to the original clone E. coli HB 101 CG-pBR 322/HlycIFN-8'$_1$.

The recombinant plasmid DNA of the clone CG-pBR (AP)/LyIFN-α-3 is isolated from the culture as described above (step 5c) and characterized by establishing the nucleotide sequence of the cDNA insert (IFN gene) and the β-lactamase regulatory region. The result is summarized in FIG. 12.

The construction protocol for the plasmid CG-pBR (AP)/LyIFN-α-3 can be used for all α-IFN cDNA genes or appropriately cut chromosomal α-IFN genes in general.

For example, starting from the plasmid CG-pBR322/HLycIFN-5$_1$, the plasmid CG-pBR (AP)-/LyIFN-α-2 is obtained in an identical manner as described for the plasmid CG-pBR(AP)/LyIFN-α-3. This new plasmid contains the DNA insert of CG-pBR 322/HLycIFN-5$_1$ and the β-lactamase regulatory region from CG-pBR (AP)/LyIFN-α-1. A clone designated E. coli HB 101 CG-pBR (AP)/LyIFN-α-2 is selected as described above. An IFN activity of 50,000(IU/ml) is found which represents a 5 fold stimulation compared to the original E. coli HB 101 CG-pBR 322/HLycIFN-5$_1$. The nucleotide sequence of the cDNA insert and the β-lactamase regulatory region of the plasmid CG-pBR (AP)/LyIFN-α-2 is established as described above and depicted in FIG. 13.

8. Cultivation of the strain E. coli HB 101 CG-pBR (AP)/LyIFN-α-3 on fermentor scale The strain E. coli HB 101 CG-pBR(AP)/LyIFN-α-3 is cultivated in medium no. X which contains the following ingredients per 1 solution:

| | |
|---|---|
| Na$_2$HPO$_4$.7H$_2$O | 13.25 g |
| KH$_2$PO$_4$ | 3.0 |
| NaCl | 0.5 |
| NH$_4$Cl | 1.0 |
| CaCl$_2$.2H$_2$O | 0.015 |
| MgSO$_4$.7H$_2$O | 0.25 |
| iron-(III)-citrate | 0,006 |
| casamino acids | 18,0 |
| yeast extract | 2,0 |
| cerelose | 8,0 |
| tetracycline | 0,01 |

Separately from the bulk of the medium cerelose and tetracycline are sterilized by heat sterilization and sterile filtration, respectively. Three 2 l-shake flasks containing 500 ml of medium no. X are inoculated each with the cells from a well grown agar plant. The shake flasks are equipped with four baffles and are incubated on a rotary shaker at 120 rpm at 30° C. for 11 hours 1.5 liters of this preculture are transferred to the baffle of a 500 l fermentor containing 300 l of medium no. X and cultivated under the following conditions: agitation at 350–500 rpm with a flat blade turbine, aeration rate 0.3–1.0 l/l·min, fermentor head pressure 0.3 bar, temperature 30° C. The level of dissolved oxygen is prevented from dropping below 50% saturation by increasing the aeration rate and, if necessary, also the agitation rate to maximal values. The pH is kept above 6.8 by controlled addition of NaOH. After cultivation for about 10 hours the culture has reached the maximal interferon titre [determined according to Armstrong (29)] and is harvested.

9. Isolation and purification of HLyIFN-α-3 a. Preparation of the polypeptide solution for the monoclonal antibody column 280 l culture broth of pH 7.2 is cooled to 10° C. and the cells are separated with an Alfa-Laval BRPX-207 de-sludger. The clear supernatant contains no IFN-activity. Before collecting the cell mass accumulated inside the solid bowl of the de-sludger, the supernatant is displaced with 20 l Lysis Buffer A [50 mM Tris·HCl, 50 mM EDTA, 0.2M NaCl, 10 mM PMSF (phenylmethylsulphonylfluoride); 1 mM L-cysteine, adjusted with HCl to pH 8.2] and the content of the centrifuge bowl (7 l) is ejected with full de-sludging. The de-sludger is washed three times with 2 l Lysis Buffer A. The obtained cell mass is adjusted with Buffer A to 20 l and has a pH value of 6.9. After cooling to 5–10° C. the suspension is passed through a DYNO ® - Mill (type KDL-Pilot, 1.4 l) provided with polyurethane agitator disks and 1170 ml glass beads of 0.5–0.75 mm diameter at an agitation speed of 3,350 rpm and a feed rate of 5 l/h, whereby the cells are disrupted. 800 ml of Lysis Buffer A (containing in addition 100 g of polyethyleneimine adjusted to pH 8.2 with HCl) are added to the obtained suspension of the disrupted cells at 2° C. with gentle stirring. The suspension having a pH of about 7.6 is cooled for three hours to −2° C. and centrifuged. To the supernatant (17.2 l) are added 3,028 g of ammonium sulphate The slightly turbid mixture is centrifuged after 1 hour of standing at 6° C. The supernatant is treated with 4,324 g of ammonium sulphate and, after standing over night, is centrifuged at 3,000 rpm. The wet centrifugate (about 1,224 g) is dissolved in Buffer B (25 mM Tris·HCl, 10 μM PMSF, adjusted to pH 8.5 with HCl) to give 2,800 ml of a solution containing the desired polypeptide.

An aliquot of 700 ml of this polypeptide solution is diafiltrated at room temperature through a H1P10 Hollow filter cartridge by means of an Amicon DC-2 Hollow Fibre System using 7 l of the buffer system B. The filter cartridge is washed with Buffer B, the diafiltrated solution and the washings are combined (1,440 ml) and passed with a flow rate of 200 ml/h onto a DEAE column (Trisacryl ® M DEAE, LKB 2205-300) with a bed volume of 450 ml which has been pre-equilibrated with Buffer B. The first polypeptide fraction with a UV-absorption at 280 nm wavelength is discarded. The column is further washed with Buffer B, until at least five bed volumes of the washings have the base line absorption at 280 nm. The adsorbed polypeptides are then eluted with 2.8 l of Buffer C. (0.2M NaCl, 25 mM Tris-HCl, pH 8.5). The column chromatography is performed at 4° C. The eluate shows in the assay according to Armstrong (29) on IFN activity of $1.4 \cdot 10^5$ IU/mg polypeptide. The eluate is adjusted with 2M HCl to pH 7.4 and 100 ml aliquots thereof are frozen at −20° C. until they are used on the monoclonal antibody column.

b) Purification of human LyIFN-α-3 on a monoclonal antibody column

The monoclonal antibody column 1K2-20 (bed volume 0,8 ml, see below) is equilibrated with PBS (phosphate-buffered saline: 0,137M NaCl, 0.0027M KCl, 0.0077M $Na_2HPO_4.12H_2O$, 0.0015M $KH_2PO_4$, pH 7.4) and 10 ml portions of the above polypeptide solution are applied onto the column at room temperature with a flow rate of 10 ml/h. The first fractions containing the nonadsorbed polypeptides and 3 ml of PBS washings are discarded. Further non specific bound polypeptides are eluted with 3 ml of PBS containing additional 0.5M NaCl and 0.2% Triton X 100. The column is washed with 3 ml of PBS, whereupon the specifically adsorbed polypeptides are eluted with 3 ml of Buffer D (0.1M citric acid, 0.3M NaCl, pH 2. This fraction and 4 ml of a consequent PBS washing are combined, adjusted to pH 6.3 with 2N NaOH and concentrated tenfold at 4° C. with the aid of an immersible-CX$^{TM}$ molecular separator (Millipore ®). The concentrate is applied onto a Sephadex G-25 fine column (2.6×34 cm, 200 ml bed volume) equilibrated with 0.025M histidin·HCl of pH 6.3. At 4° C. and with a flow rate of 42 ml/h the column is eluted with the same histidin·HCl of pH 6.3, whereby 20 fractions are collected of each 10.5 ml. Polypeptide containing fractions are detected by their optical absorption at 280 nm. Fractions 7 and 8 contain the polypeptide with IFN activity as localised by the assay according to Armstrong (29). The active fractions containing LyIFN-α-3 are stored at −20° C. or in an ice bath until further use. The IFN activity of the fractions is $1.8 \cdot 10^8$ IU/mg polypeptide (29).

By lyophilizing the above fractions from 1 ml solution 20–40 μg of polypeptide are obtained.

SDS polyacrylamide gel electrophoresis (cf. (49))reveals a molecular weight for the obtained LyIFN-α-3 of about 18 kDaltons.

Ultrathinlayer isoelectric focusing on polyacrylamide gel (100 μM), carried out according to B. J. Radola (50) within a pH range from 4.5 to 6.5 reveals the pure active human LyIFN-α-3 at the isoelectric point of 5.3–5.4 pH units.

c) Preparation of the monoclonal antibody column 1K2-20

(A) Immunization of mice

Balb/c mice (8 weeks old, obtained from Tierfarm Sisseln, Switzerland) are injected with $3 \times 10^5$ units of human leukocyte IFN-α (purity 1%) in complete Freund's adjuvant (Difco) distributed into 4 footpads At day 30, the same amount of IFN in incomplete Freund's adjuvant is injected the same way. Third injection is made on day 85, when $4 \times 10^5$ units of human leukocyte IFN is given intraperitoneally in saline. Four days later spleens are taken for the fusion

(B) Preparation of hybridomas

All the fusion experiments using X63-Ag8-653 myeloma line (52) are essentially performed according to the method of Köhler and Milstein (53), by mixing $10^8$ spleen cells with $10^7$ myeloma cells using 1 ml of 50% polyethylene glycol (PEG 1500, Serva) (54). After washing, the cells are resuspended in 48 ml standard Dulbecco's minimum essential medium (Gibco). 15% fetal calf serum and $3 \times 10^6$ normal mouse peritoneal exudate cells per fusion are added as feeder cells. Cells are distributed into $48 \times 1$ ml Costar wells. The cultures are fed twice weekly with standard selective medium (53) for 3 to 6 weeks. When the hybrids have grown they are frozen and the supernatants are tested for anti-IFN activity as described below. The cloning of the hybridoma cells is done by limiting dilution in microtiter plates.

(C) Antibody Assays

To test the anti-IFN activity of the supernatant 50 μl of IFN-α (final 10-20 units IFN/ml) are incubated with 50 μl of the culture supernatant at room temperature, and 30-60 minutes later the residual activity of IFN is tested in a standard IFN assay. This method which works for conventional antibodies either fails or gives unreproducible results for the assay of hybridoma supernatants. The following combined immunoprecipitation-bioassay is therefore developed for this purpose. Fifty μl of crude IFN-α ($10^4$ U/ml) is mixed (in microtubes 3810, Eppendorf) with equal amount of culture supernatant and the mixture is incubated at 37° C. for 2-4 hours. Subsequently 50 μl of previously titrated rabbit anti-mouse Ig antibody (Nordic) is added and the mixture is incubated first at 37° C. for 1 hour and then at +4° C. for 16 hours to form immune complexes. The tubes are then centrifuged at 12.000 rpm for 5 min in a cold room. The supernatant is saved and the precipitate is washed once with 1 ml buffered saline pH 7.2. After washing, the precipitate is dissolved in 200 μl of saline pH 2.2. The IFN activity is assayed according to Armstrong (29).

(D) Purification of anti-IFN antibody isolated form ascitic fluid

Balb/c mice are primed with 0,4 ml Pristan (Carl Roth) intraperitoneally. One week later the mice are injected i.p. with $2-5 \times 10^6$ hybridoma cells. Ascitic fluid is collected repeatedly from each mouse. The fluids are pooled and frozen at −80° C. After thawing the pool is centrifuged at 16.000 rpm for 30 minutes. The fat at the top is sucked off and the supernatant free of debris is saved. When necessary the centrifugation is repeated A crude immunoglobulin fraction is obtained from the ascitic fluid by 18% $Na_2SO_4$ precipitation at room temperature. Subsequently this fraction is passed through Sephacryl G 200 (Pharmacia) according to manufacturer's instructions using 0,1M Tris-HCl buffer pH 8.2. Active fractions are pooled and concentrated by Amicon XM 50 filters (Amicon). Protein determination is done by $OD_{280}$ measurement assuming that 1 mg of protein gives rise to an absorbance of 1.2 at 280 nm in a 1 cm cuvette.

(E) Immunoadsorbent column 1K2-20

One ml of settled Affi-Gel 10 (Bio-Rad) is coupled to 15 mg of immunoglobulin of monoclonal anti-IFN antibody according to the manufacturer's instruction: Affi-Gel 10 is washed on glass fritted funnel first with cold distilled water and then with a 0,1M $NaHCO_3$ solution pH 8,0 (coupling buffer). 50% gel in coupling buffer is transferred into a plastic tube, mixed with equal amounts of purified antibody solution and rotated for 4 hours at room temperature. After coupling the gel is washed with coupling buffer and, in order to block the unreacted sites, it is treated with 0,1 ml of 1M ethanolamine-HCl (pH 8.0) per ml of gel for 1 to 2 hours at room temperature. The gel is washed with phosphate-buffered saline in the presence of 10 mM $NaN_3$ and kept therein at 4° C. 0.8 ml of the resulting gel is used to prepare the monoclonal antibody column (named 1K2-20) used for the preparation of human LyIFN (cf. above).

10. Pharmaceutical preparations (parenteral administration)

2 mg of lymphoblastoid interferon, for example LyIFN-α-3 isolated from the clone E. coli HB 101 CG-pBR(AP)/LyIFN-α-3 (see Example 9), having a specific activity of $1.8 \cdot 10^8$ units/mg, are dissolved in 30 ml of 5N human serum albumin. The resulting solution is passed through a bacteriological filter and the filtered solution is subdivided under aseptic conditions into 100 vials each containing $3.6 \times 10^6$ units of pure lymphoblastoid interferon. The vials which are suitable for parenteral administration are preferably stored in the cold, for example at −20° C.

In the samer manner, vials containing $7.2 \times 10^6$ or $1.08 \times 10^7$ units, may be prepared by using 4 or 6 mg, respectively, of the above lymphoblastoid interferon.

11. Determination of the N-terminal sequence of recombinant interferons α-1 and α-2

A. Cultivation on fermentar scale

The strains E. coli HB101 CG-pBR(AP)/LyIFN-α-1 and E. coli HB 101 CG-pBR(AP)/LyIFN-α-2 are each cultivated in 500 ml shake flasks for 17 hours. The composition of the culture medium is as follows (medium no. X; ingredients per 1 l solution):

| | |
|---|---|
| $Na_2HPO_4.7H_2O$ | 13.25 g |
| $KH_2PO_4$ | 3.0 g |
| NaCl | 0.5 g |
| $NH_4Cl$ | 1.0 g |
| $CaCl_2.2H_2O$ | 0.015 g |
| $MgSO_4.7H_2O$ | 0.25 g |
| iron-(III)-citrate | 0.006 g |
| casamino acids | 18.0 g |
| yeast extract | 2.0 g |
| cerelose | 8.0 g |
| tetracycline | 0.01 g |

A 1% inoculum (300 ml) of the preculture is used to inoculate a 30 l fermenter containing medium with the same composition as the shake flask cultures (medium no. X). This fermenter runs for 10 h before transfer of 1% inoculum to the production fermenter. The 30 l production stage is carried out in a fermenter having a single disc turbine agitator and four baffles. The agitation rate and aeration rate are adjusted during the fermentation to maintain an adequate oxygen transfer rate. The culture medium has the following slightly nodified composition (medium no. X'; ingredients per 1 l solution):

| | |
|---|---|
| Na$_2$HPO$_4$.7H$_2$O | 13.25 g |
| KH$_2$PO$_4$ | 3.0 g |
| NaCl | 0.5 g |
| NH$_4$Cl | 2.5 g |
| CaCl$_2$.2H$_2$O | 0.015 g |
| MgSO$_4$.7H$_2$O | 0.25 g |
| iron-(III)-citrate | 0.006 g |
| casamino acids | 9.0 g |
| yeast extract | 2.0 g |
| cerelose | 20.0 g |
| tetracycline | 0.005 g |

The temperature is maintained at 32° C. and the pH at 6.8. The culture is harvested when the optical densityreaches 6.0 (after about 8h).

60 l culture broth from two 30 l fermenters of pH 5.8 is cooled to 10° C. and the cells are separated with a Sharples centrifuge. The clear supernatant contains noIFN activity. The obtained cell mass is adjusted with Buffer X (2 mM Tris pH 8.0, 5 mM EDTA, 0.5M NaCl, 20 μM phenylmethylsulphonylfluoride) to 4150 ml and has a pH value of 8.0. After cooling to 5-10° C. the suspension is passed through a DYNO ® -Mill (type KDL Pilot, 0.6 l) provided with polyurethane agitator disks and 500 ml glass beads of 0.5-0.75 mm diameter and having an agitation speed of 3,000 rpm and a feed rate of 10 l/h, whereby the cells are disrupted. The suspension has a pH value of 8. The suspension containing the broken cells is clarified by centrifugation. The centrifugation is performed in a Sorvall GS-3 rotor at 8,000 rpm at 4° C. for 30 min.

B. Purification of the recombinant interferons α-1 and α-2 a. Immunization protocol and cell fusion

Seven female Balb/c mice (Tierfarm Sisseln, Switzerland) 10-14 weeks old are immunized by injection into the four footpads of 4×10$^5$ IU of LyIFN-α-2 emulsified in complete Freund's adjuvant (Difco). A further injection of 4×10$^5$ IU of LyIFN-α-2 in incomplete Freund's adjuvant is given at day 30, and a booster injection (i.p.) of 6×10$^5$ IU of IFN-α-2 in PBS at day 60. Three days later the spleens are taken for the fusion.

All fusion experiments are performed according to the procedure of G. Köhler and C. Milstein (Nature 256, 495 (1975)) using the non-secreting Sp 2/0-Ag14 myeloma line (M. Shulman, C. D. Wilde and G. Köhler, Nature 276, 269 (1978)). 10$^8$ spleen cells are mixed with 10$^7$ myeloma cells in the presence of 1 ml of 50% polyethylene glycol (PEG 1500, Serva). After washing, the cells are resuspended in 48 ml of standard Dulbecco's minimum essential medium (Gibco No. 0422501). 3×10$^6$ normal mouse peritoneal exsudate cells per fusion are added as feeder cells. The cells are distributed into 48×1 ml costar wells and fed 3 times per week with standard HAT selection medium for 3 to 6 weeks. When the growth of hybridoma cells becomes visible, the supernatants are screened by a combined immuno-precipitation-bioassay. Out of a total of 221 hybridomas, 10 hybridomas are found to produce anti-IFN-α antibodies. The hybridoma cells are cloned by limiting dilution in microtiter plates at least once. Hybridoma 144BS is selected because it is particularly stable and secretes large quantities of immunoglobulin. Hybridoma cell line 144BS ("1.144 BS 22-6-19") has been deposited on March 14, 1985 at the "Collection Nationale de Cultures de Microorganismes", Institut Pasteur, Paris, under the number I-424.

b. Isolation and purification of monoclonal antibody 144BS

Balb/c mice 8-10 weeks of age (Tierfarm Sisseln, Switzerland) are pretreated intraperitoneally with 0.3 ml pristane (Aldrich). 2-3 weeks later, 2-5×10$^6$ cloned hybridoma cells and 0.2 ml pristane are inoculated intraperitoneally. After 8-10 days ascites fluid is collected, centrifuged at 800×g and stored at −20° C.

Defrosted ascites fluid is centrifuged at 50,000×g for 60 min. A fat layer floating on the surface is carefully removed, and the protein concentration is adjusted to a concentration of 10-12 mg/ml. Crude immunoglobulin is precipitated by dropwise addition of 0.9 volume equivalents of saturated ammonium sulphate at 0° C., then dissolved in 20 mM Tris-HCl/50 mM NaCl (pH 7.9) and dialysed against the same buffer. An immunoglobulin fraction is obtained by DEAE-D52 cellulose (Whatman) chromatography using a buffer gradient system of 20 mM Tris-HCl/25–400 mM NaCl, pH 7.9. The immunoglobulin is again precipitated with ammonium sulphate and dissolved in PBS at a concentration of 10 mg/ml.

Sodium dodecyl sulphate polyacrylamide gel electrophoresis (SDS-PAGE) demonstrates a purity grade of more than 95 percent for the monoclonal antibodies 144BS.

c. Preparation of the polypeptide solution for the monoclonal antibody column All manipulations are performed at 4° C. To the interferon containing solution clarified by centrifugation polyethyleneimine (Polymin P ® pH 8.0) is added to a final concentration of 0.25% (w/v). The solution is stirred for 1 h and subsequently centrifuged. The pellet is discarded and the supernatant is brought to 30% saturation with solid ammonium sulfate.

The solution is stirred for 1 h and subsequently centrifuged (Sorvall GS-3 rotor, 8,000 rpm for 30 min. at 4° C.). The pellet is discarded and the supernatant is brought to 65% saturation with solid ammonium sulfate. This mixture is stirred for 1 h and then centrifuged (Sorvall GS-3 rotor, 8,000 rpm for 30 min. at 4° C.). The supernatant is discarded and the pellet is suspended in 1/10 volume (15-20 ml) of buffer containing 20 mM NaH$_2$PO$_4$, 80 mM K$_2$HPO$_4$, 150 mM NaCl, pH 7.2 (PBS). The solution is dialysed overnight against PBS containing 0.02% NaN$_3$.

d. Immunoaffinity chromatography

The dialysed solution is mixed with 2 ml Affigel 10 to which 17 mg of monoclonal antibody 144BS is coupled. This mixture is gently agitated for 1 hour. The gel matrix is packed into a column and washed with 5 column volumes of PBS, 5 column volumes of PBS containing 0.5M NaCl and 0.2% Triton X-100 and again with 5 column volumes of PBS. The interferon is eluted from the column at pH 2.5 with buffer containing 0.1M citric acid and 0.3 M NaCl. The active interferon fractions are neutralised (1M Tris), dialysed against PBS and concentrated to about 0.1 mg/ml protein using ultrafiltration flat bed membranes XM 10 (Amicon).

C. Physicochemical characterization of interferons α-1 and α-2

Interferons α-1 and α-2 purified as described above are each subjected to polyacrylamide SDS-gelelectrophoresis according to the literature (U. K. Lämmli, Nature, (1970) 227, 680.) The antibody purified materials show apparent molecular weights of 27,000 daltons (interferon α-2) and 21,000 daltons (interferon α-1), respectively. The purity of the interferons is better than 95%.

D. Determination of the N-terminal sequences 1 mg of antibody purified interferon α-1 or α-2 is each dialysed against 0.1M $NH_4HCO_3$ (Spectrapor dialysis tubing MW cut off 3,500) and then lyophilised. Carboxymethylation is performed according to the literature (A. M. Crestfield et. al., Biol.Chem. (1963) 238, 622) with the following modifications:

The lyophilised protein is dissolved in 0.5M Tris buffer pH 7.5 containing 5M guanidinium-HCl, 0.2% disodium EDTA and 1% β-mercaptoethanol. After denaturation and carboxymethylation using iodoacetate the sample is dialysed in the dark against 0.1M $NH_4HCO_3$ and lyophilised.

The lyophilised samples of each of the interferons α-1 and α-2 are subjected to automated Edman degradation in a model 470 A gasphase protein sequencer from Applied Biosystems. The amino acids derivatives produced in the sequencer are analysed by high performance liquid chromatography (M. W. Hunkapiller et. al. (1983) Methods in Enzymology Vol. 91, 399-413).

Results of automated Edman degradation of interferons α-1 and α-2 with subsequent HPLC analysis:

|  | a. Interferon α-1 | | | |
|---|---|---|---|---|
| degradation step | 1 | 2 | 3 | 4 |
| amino acid | CMCys | Asp | Leu | Pro |
| yield (nmoles) | (1) | 1.29 | 3.80 | 2.14 |
|  | b. Interferon α-2 | | | |
| degradation step | 1 | 2 | 3 | 4 |
| amino acid | CMCys | Asp | Leu | Pro |
| yield (nmoles) | (1) | 1.1 | 3.2 | 1.7 |

(1) CMCys (carboxymethyl cysteine) can only be determined qualitatively because it is converted into various products in the sequencer. The main peak in HPLC analysis has the expected absorptions at 254 nm and 313 nm. Compared to the corresponding Leu absorption the yield is assessed at about 10%.

The results establish that both interferons α-1 and α-2 have a N-terminal sequence of Cys-Asp-Leu-Pro- . . . No methionine is detectable in step 1.

Deposition of the prepared microorganisms

Micro-organisms and recombinant DNA molecules prepared by the processes described herein are exemplified by cultures deposited in the culture collection of the Agricultural Research Culture Collection (NRRL) on September 14, 1981 and are assigned the following accession numbers:

| | |
|---|---|
| E. coli HB 101 CG-pBR 322/HLycIFN-β₁: | NRRL B-12528 |
| E. coli HB 101 CG-pBR 322/HLycIFN-4₁: | NRRL B-12529 |
| E. coli HB 101 CG-pBR 322/HLycIFN-1'b: | NRRL B-12530 |
| E. coli HB 101 CG-pBR 322/HLycIFN-5₁: | NRRL B-12531 |
| E. coli HB 101 CG-pBR 322/HLycIFN-8'₁: | NRRL B-12532 |

REFERENCES

1. W. E. Stewart, II, The Interferon System, Springer Verlag, Vienna (1979)
2. Interferon nomenclature, Nature 286, 110 (1980)
3. C. Weissmann, "DNA Sequences, recombinant DNA molecules and processes for producing human interferon-like polypeptides", European patent application No. 32134 (Biogen N. V.)
4. E. A. Havell et al., "Characteristics of Human Lymphoblastoid (Namalva) Interferon", J. Gen. Virol. 38, 51-59 (1977)
5. A. D. Sagar et al., "Heterogeneity of interferon mRNA species from Sendai virus-induced human lymphoblastoid (Namalva) cells and Newcastle disease virus-induced murin fibroblastoid (L) cells", Nucl. Acids Res. 9, 149-160 (1981)
6. M. Rubenstein et al., "Human Leukocyte Interferon: Production, Purification to Homogeneity and Initial Characterization", Proc. Natl. Acad. Sci. USA 76, 640-644 (1979)
7. W. E. Steward, IIetal., "Effect of Glycosylation Inhibitors on the Production and Properties of Human Leukocyte Interferon", Virology 97, 473-476 (1979)
8. K. C. Zoon et al., "Amino Terminal Sequence of the Major Component of Human Lymphoblastoid Interferon", Science 207, 527-528 (1980)
9. S. N. Cohen and H. W. Boyer, "Process for Producing Biologically Functional Molecular Chimeras", U.S. Pat. No. 4,237,224 (Leland Stanford Jr. University)
10. S. Nagata et al., "Synthesis in E. coli of a polypeptide with human leukocyte interferon activity", Nature 284, 316-320 (1980)
11. N. Mantei et al., "The nucleotide sequence of a cloned human leukocyte interferon cDNA", Gene 10, 1-10 (1980)
12. M. Streuli et al., "At least Three Human Type α Interferons: Structure of α2", Science 209, 1343-1347 (1980)
13. D. V. Goeddel et al, "Human leukocyte interferon produced by E. coli is biologically active", Nature 287, 411-416 (1980)
14. D. V. Goeddel et al., "The structure of eight distinct cloned human leukocyte interferon cDNAs", Nature 290, 20-26 (1981)
15. J. Groneberg et al., "Mikrobiologisch hergestelltes Polypeptid mit der Aminosäuresequenz des menschlichen Interferons, DNA und Plasmide, die für diese Sequenz codieren, Mikroorganismen, die diese genetische Information enthalten, und Verfahren zu deren Herstellung", European patent application No. 34307 (Hoechst Aktiengesellschaft)
16. H. Sugano et al., "Novel DNA, cloned DNA, recombinant plasmid containing the DNA, microorganism containing the recombinant plasmid and process for their production", European patent application No. 28033 (Japanese Foundation of Cancer Research)
17. T. Taniguchi et al., "The nucleotide sequence of human fibroblast interferon cDNA", Gene 10, 11-15 (1980)
18. R. Derynck et al., "Isolation and structure of a human fibroblast interferon gene", Nature 285, 542-547 (1980)
19. D. V. Goeddel et al., "Synthesis of human fibroblast interferon by E. coli", Nucl. Acids Res. 8, 4057-4075 (1980)

20. M. Revel et al., "Production of interferon by genetic engineering", UK patent application No. 2,063,882 (Yeda Research and Development Company)

21. "Gene for expressing protein similar to human interferon, derived plasmid recombinants, and modified bacterial cells", BE patent No. 887,397 (Searle & Co.)

22. J. Groneberg et al., "Mikrobiologisch hergestelltes Polypeptid mit der Aminosäuresequenz des menschlichen Interferons, DNA und Plasmide, die für diese Sequenz codieren, Mikroorganismen, die diese genetische Information enthalten, und Verfahren zu ihrer Herstellung", European patent application No. 34306 (Hoechst Aktiengesellschaft)

23. T. Taniguchi et al., "Human leukocyte and fibroblast interferons are structurally related", Nature 285, 547–549 (1980)

24. M. D. Johnston et al., "Factors influencing production of interferon by human lymphoblastoid cells", Adv. Exp. Med. Biol. 110, 61–74 (1978)

25. G. Allen et al., "A family of structural genes for human lymphoblastoid (leukocyte-type) interferon", Nature 287, 408–411 (1980)

26. H. Strander et al., "Production of human lymphoblastoid interferon", J. Clin. Microbiol. 1, 116–117 (1975)

27. M. D. Johnston, "Improvement in or relating to a process for producing interferon", European patent application No. 520 (Wellcome Foundation)

28. P. Swetly et al., "Verbessertes Verfahren zur Herstellung von Humaninterferon aus lymphoblastoiden Zellen", German Offenlegungsschrift No. 2,946,275 (Thomae)

29. J. A. Armstrong, "Semi-Micro Dye-Binding Assay for Rabbit Interferon", Appl. Microbiol. 21, 723–725 (1971)

30. A. Colman et al., "Export of Proteins from Oocytes of Xenopus laevis", Cell 17, 517–526 (1979)

31. W. E. Stewart, II et al., "Interferon Production in Hamsters Experimentally Infected With Rabies Virus", Proc. Soc. Exp. Biol. Med. 123, 650–653 (1966)

32. A. C. Peacock et al., "Resolution of Multiple Ribonucleic Acid Species by Polyacrylamide Gel Electrophoresis", Biochemistry 6, 1818–1827 (1967)

33. P. B. Sehgal et al., "Heterogeneity of poly(I)·poly(C)-induced human fibroblast interferon in RNA species", Nature 288, 95–97 (1980)

34. J. G. Sutcliffe, "pBR 322 restriction map derived from the DNA sequence: accurate DNA size markers up to 4361 nucleotide pairs long", Nucl. Acids Res. 5, 2721–2728 (1978)

35. M. Mandel et al., "Calcium-dependent Bacteriophage DNA Infection", J. Mol. Biol. 53, 159–162 (1970)

36. M. Grunstein and D. S. Hogness, "Colony hybridization: A method for the isolation of cloned DNAs that contain a specific gene", Proc. Natl. Acad. Sci. 72, 3961–3965 (1979)

37. K. Itakura et al., "Chemical DNA Synthesis and Recombinant DNA studies", Science 209, 1401–1405 (1980)

38. K. Itakura et al., "Improved Triester Approach for the Synthesis of Pentadecathymidylic Acid", J. Am. Chem. Soc. 97, 7327–7332 (1975)

39. J. F. M. de Rooij et al., "Synthesis of complementary DNA fragments via phosphotriester intermediates", Recl. Trav. Chim. Pays-Bas 98, 537–548 (1979)

40. F. Sanger et al., DNA sequencing with chain-terminating inhibitors, Proc. Natl Acad. Sci. USA 74, 5463–5467 (1977)

41. A. M. Maxam and W. Gilbert, "A new method for sequencing DNA", Proc. Natl. Acad. Sci. USA 74, 560–564 (1977); see also Meth. Enzym. 65, 499–559 (1980)

42. J. B. Gurdon, J. Embryol. Exp. Morph. 20, 401–414 (1968)

43. Barth, J. Embryol. Exp. Morph. 7, 210–222 (1959)

44. A. Efstratiadis et al., Full Length and Discrete Partial Reverse Transcripts of Globin and Chorion mRNAs, Cell 4, 367–378 (1975)

45. T. Maniatis et al., "Amplification and Characterization of a β-Globin Gene Synthesized in Vitro", Cell 8, 163–182 (1976)

46. J. H. J. Hoeijmakers et al., "The isolation of plasmids containing DNA complementary to messenger RNA for variant surface glycoproteins of Trypanosoma brucei", Gene 8, 391–417 (1980)

47. W. Mueller et al., "Site-directed Mutagenesis in DNA: Generation of Point Mutations in Cloned β Globin Complementary DNA at the Positions Corresponding to Amino Acids 121 to 123", J. Mol. Biol. 124, 343–358 (1978)

48. J. Weissenbach et al., "Two interferon mRNAs in human fibroblasts: In vitro translation and Escherichia coli cloning studies", Proc. Natl. Acad. Sci. USA 77, 7152–7156 (1980).

49. U. K. Laemmli, Nature 227, 680–685 (1970).

50. B. J. Radola, "Electrophoresis", p. 79–94, Walter de Gruyter, Berlin-N.Y. 1980.

51. T. Staehelin et al., J. Biol. Chem. 256, 9750–9754 (1981).

52. J. F. Kearney et al., J. Immunolog. 123, 1548 (1979).

53. G. Köhler and C. Milstein, Nature 256, 459 (1975).

54. G. Galfre et al., Nature 266, 550 (1977).

I claim:

1. A method for producing a polypeptide selected from HLycIFN-1'b, HLycIFN-5₁, LyIFN-α-1, and LyIFN-α-2 which comprises:
   (a) preparing from HuLyIFN-mRNA a single-stranded complementary DNA and, if required, therefrom a double-stranded cDNA coding for any of said polypeptides; or
   (b) partially cleaving the chromosomal DNA of human lymphoblastoid cells and selecting DNA fragments which contain chromosomal LyIFN genes coding for any of said polypeptides;
   (c) introducing into a vector DNA the complementary DNA from step (a) or the DNA fragments which contain chromosomal LyIFN genes from step (b);
   (d) transforming a host cell with the vector from step (c);
   (e) culturing the transformed host; and
   (f) recovering said polypeptide.

2. A method according to claim 1 wherein the interferon is LyIFN-α-1.

3. A method according to claim 1 wherein the interferon is LyIFN-α-2.

4. A DNA in substantially pure form containing a DNA sequence which codes for HLycIFN-1'b and consists of:
ACATCCCAATGGCCCTGTCCTTTTCTTTACT-
GATGGCCGTGCTGGTGCTCAGC- TACAAATCCATCTGT
TCTCTGGGCTGTGATCTCCCTCAGACC-
CACAGCCTGGGTAATAGGAGGGCCTT-
GATACTCCTGGCACA AATG-
GGAAGAATCCCCCCTTTCTCCTGCCT-
GAAGGACAGACATGACTTTGGATTTCC-
CCAGGAGGACT TTGATGGCAACCAGTT-
CCAGAAGGCTCAAGCCATCTCTGTCCT-
CCATGAGATGATCCAGCACACCTTC
AATCTCTTCAGCACAAAGGACTCATCTG-
CTACTTGGGAACAGAGCCTC-
CTAGAAAATTTTCCACTGA ACTTAAC-
CAGCAGCTGAATGACCT-
GGAAGCCTGCGTGATACAG-
GAGGTTGGGGTGGAAGAGACTCCCC-
TGATGAATGTGGACTCCATCCTGGCTGT-
GAAGAAATACTTCCAAACAATCACTCTT-
TATCTGACAGAG AAGAAATA-
CAGCCCTTGTGCCTGGGAGGTTGT-
CAGAGCAGAAATCATGAGATCCTTCTCTT-
TATCAAA AATTTTTCAAGAAAGATTAAG-
GAGGAAGGAATGAAACCTGTTT-
CAACATGCAAATGATCTGTATTGAC
TAATACACCAGTCCACACTTCTAT-
GACTTCTGCCATTTCAAAGACT-
CATTTCTCCTATAACCACCGCA TGAGTT-
CAATCAAAATTTTCAGATCTTTTCAG-
GACTGTAAGGAAACATCATGTTTACCTGT-
GCAGGCA CTAGTCCTTTACAGATGAC-
CATGCTGATAGATCTAATTATCTATC-
TATTGAAATATTTATTTATTTAT TAGATT-
TAAATTATTTTTGTCCATGTAATAT-
TATGTGTACTTTTACATTGTGTTATAT-
CAAAATATGT TATTTATATTTAGT-
CAATATATTATTTTCTTTTTATTAATTTT-
TACTATTAAAACTTCTTATATTATT
TGTTTATTG, HLyclFN-5₁ and consists of:

ATCTGAACCAGCTCAGCAGCATC-
CACAACATCTACAATGGCCTTGACTTTT-
TATTTACTGGTGGCCC TAGTGGTGCT-
CAGCTACAAGTCATT-
CAGCTCTCTGGGCTGCGATCTGCCT-
CAGACTCACAGCCTGGG TAACAG-
GAGGGCCTTGATACTCCTGGCACAAATG-
CGAAGAATCTCTCCTTTCTCCTGCCT-
GAAGGAC AGACATGACTTTGAATTCCC-
CCAGGAGGAGTTTGATGATAAACAGTT-
CCAGAAGGCTCAAGCCATCT
CTGTCCTCCATGAGATGATCCAG-
CAGACCTTCAACCTCTTCAGCACAAAG-
GACTCACCTGCTGCTTT GGAT-
GAGACCCTTCTAGATGAATTCTACACT-
GAACTTGACCAGCAGCTGAATGACCT-
GCAG TCCTGTGTGATGCAG-
GAAGTGGGGGTGATAGAGTCTCCCCT-
GATGTACGAGGACTCCTCTCTGGCTG
TGAGGAAATACTTCCAAAGAATCACT-
CTATATCT-
GACAGAGAAGAAATA-
CAGCTCTTGTGCCTGGGA
GGTTGTCAGAGCAGAAATCAT-
GAGATCCTTCTCTTTATCAATCAACTT-
GCAAAAAGATTGAAGAGT AAGGAAT-
GAGACCTGGTACAACACGGAAAT-
GATTCTTATAGACTAATACAGCAGCT-
CACACTCTGAC AAGTTGTGCTCTTT-
CAAAGACCCTTGTTTCTGCCAAAACCATG-
CTATGTTTTGAATCAAATGTGTCA
ATGTTTTTCAGGAGTGTTAAG-
CAACATCCTGTTCAGCTGTATGGGCAC-
TAGTCCCTTACAGATGACC ATGCTGATG-
GATCTATTCATCTATTTATTTAAATCTT-
TATTTAGTTAACTATCTATAGGGCT-
TAAAT TATGTTTGTTCATATTATAT-
TATGTGAACTTTTATATGATGAATTGT-
GTAACAAAAACATGTCTTTT ATATTAAT-
TATTTTGCCTTCTTTATTAAATTTTTAC-
TATAG for LyIFN-α-1 and consists of:

GAGACAATAACCCTGATAAATGCTT-
CAATAATATTGAAAAAGGAAGAG-
TAATGTGTGATCTGCCTCA GACC-
CACAGCCTGGGTAATAGGAGGGCCTT-
GATACTCTCGGCACACATG-
GAAGAATCCCCCCTTTC TCCTGCCTGAAG-
GACAGACATGACTTTGGATTTCCCCAC-
GAGGAGTTTGATGGCAACCAGTTCCAGA
AGGCTCAAGCCATCTCTGTCCTCCAT-
CAGATGATCCAGCAGACCTTCAATCTCT-
CTAGCACAAGG ACTCATCTGCTACTTG-
GGAACAGAGCCTCCTAGAAAATTTT-
CCACTGAACTTAACCAGCAGCTGAA
TGACCTGGAAGCCTGCGTGATACAG-
GAGGTTGGGGTGGAAGAGACTCCCCT-
GATGAATGTGGACTCC ATCCTGGCTGT-
GAAGAAATACCCTCAAAGAATCACTCTT-
TATCTGACAGAGAAGAAATACAGCCCTT
GTGCCTGGGAGGTTGTCAGAGCAGAAAT-
CATGAGATCCCTCTCTTTAT-
CAAAAATTTTTCAAGAAAG ATTAAGGAG-
GAAGGAATGAAACCTGTTTCAACATG-
GAAATGATCTGTATTGACTAATACAC-
CAGTCC AATTTTCAGATCTTTTCAGGAGT-
GTAAGGAAACATCATGTTTACCTGT-
GCAGGCACTATGCCTTTAC AGATGAC-
CATGCTGATAGATCTAATTATCTATC-
TATTGAAATATTTATTTATTTATTAGATT-
TAAAT TATTTTTGTCGATGTAATAT-
TATGTGTACTCTTACATTGTGTTATAT-
CAAAATATGTTATTTATATT TAGT-
CAATATATTATTTTTCTTTTATTAATTTT-
TACTATTAAAACTCTTTATATTATTTGTT-
TATTC or for LyIFN-α-2 and consists of: GAGACAA-
TAACCCTGATAAATGCTTCAATAATATT-
GAAAAAGCAAGAGTAATGTGT-
GATCTGCCTC AGACTCACAGCCTGG-
GTAACAGGAGGGCCTTGATACTCCTG-
GCACAAATAAGAATCTCTCCTT
TCTCCTGCCTGAAGGACAGACATCACTTT-
GAATTCCCCCAGGAGGAGTTTGAT-
GATAAACAGTCCC AGAAGGCTCAAGC-
CATCTCTGTCCTCCATGAGATGATCCAG-
CAGACCTTCAACCTCTTCAGCACAA AG-
GACTCATCTGCTGCTTTGGATGAGACCCTT-
CTAGATGAATTCTACATCGAACTTGACCAG-
CAGC TGAATGACCTGGAGGTCTCTGT-
GATGCAGGAAGTGGGGGT-
GATAGAGTCTCCCCTGATGTACGAGG ACT-
CCATCCTGGCTGTGAGGAAATACTT-
CCAAAGAATCACTCTATATCT-
GACAGAGAAGAAATACA
GCTCTTGTGCCTGGGAGGTTGTCAGAG-
CAGAAATCATGAGATCCTTCTCTTTAT-
CAATCAACTTGC AAAAAAGATTGAAGAG- TAAGGAATGAGACCTCGTACAACACG-
GAAATGATTCTTATAGACTAATAC AG-
CAGTCTACACTTCGACAAGTTGTGCTCTTT-
CAAAGACCCTTGTTTCTGCCAAAACCATG-
CTATG TTTTGAATCAAATGTGT-
CAAGTGTTTTCAGGAGTGTTAAG-
CAACATCCTGTTCAGCTGTATGGGCA
CTAGTCCCTTACAGATGACCATCTTGATG-
GATCTATTCATCTATTTATTTAAATCTT-
TATTTAGTT AACTATCTATAGGGCTTAAAT-
TAGTTTTGTTCATATTATATTATGT-
GAACTTTTACATTCTGAATT
GTGTAACAAAAACATGTTCTTTATATTTAT-
TATTTTGCTCTGTTTATTAAATTTTTAC-
TATAG 5. A DNA according to claim 4 wherein the DNA sequence code for HLycIFN-1′b.

6. A DNA according to claim 4 wherein the DNA sequence code for HLycIFN-5₁.

7. A DNA according to claim 4 wherein the DNA sequence code for LyIFN-α-1.

8. A DNA according to claim 4 wherein the DNA seuqence code for LyIFN-α-2.

9. A recombinant DNA containing a DNA sequence coding for an interferon selected from HLycIFN-1′b, HLycIFN-5₁, LyIFN-α-1 or LyIFN-α-2.

10. The recombinant DNA CG-pBR 322/HLycIFN-1′b, according to claim 9.

11. The recombinant DNA CG-pBR 322/HLycIFN-5₁, according to claim 9.

12. A recombinant DNA according to claim 9 containing the expression control sequence of the β-lactamase gene.

13. A host cell transformed with at least one recombinant DNA containing a DNA sequence coding for an interferon selected from HLycIFN-1′b, HLycIFN-5₁, LyIFN-α-1 and LyIFN-α-2 and mutants of said host cell containing any of said DNA sequences.

14. A transformed host cell according to claim 13 selected from a bacillus, a yeast, a fungi, an animal or plant host cell or a human tissue cell.

15. A transformed *E. coli* strain according to claim 13 and mutants thereof.

16. The transformed host *E. coli* HB 101 CG-pBR 322/HLycIFN-1′b (NRRL B-12530), and mutants thereof, according to claim 13.

17. The transformed host *E. coli* HB 101 CG-pBR 322/HLycIFN-5₁ (NRRL B-12531) and mutants thereof, according to claim 13.

18. A method for the preparation of DNA containing a DNA sequence coding for an interferon selected from HLycIFN-1′b, HLycIFN-5₁, LyIFN-α-1, or LyIFN-α-2 which comprises:
(a) preparing from HyLyIFN-mRNA a single-stranded complementary DNA and, therefrom a double-stranded cDNA coding for any of said polypeptides; or
(b) partially cleaving the chromosomal DNA of human lymphoblastoid cells and selecting DNA fragments which contain chromosomal LyIFN genes coding for any of said polypeptides.

19. A method according to claim 18 comprising the additional step of introducing into a vector DNA the complementary DNA from step (a) or the fragments from step (b).

20. A method according to claim 19 wherein the interferon is LyIFN-α-1.

21. A method according to claim 19 wherein the interferon is LyIFN-α-2.

22. A method according to claim 18 wherein the interferon is LyIFN-α-1.

23. A method according to claim 18 wherein the interferon is LyIFN-α-2.

24. A method for producing a transformed host cell containing a DNA sequence coding for an interferon selected from HLycIFN-1′b, HLycIFN-5₁, LyIFN-α-1 and LyIFN-α-2 which comprises:
(a) preparing from HuLyIFN-mRNA a single-stranded complementary DNA and, if required, therefrom a double-stranded complementary DNA and, therefrom a double-stranded cDNA coding for any of said polypeptides; or
(b) partially cleaving the chromosomal DNA of human lympholastoid cells and selecting DNA fragments which contain chromosomal LyIFN genes coding for any of said polypeptides;
(c) introducing into a vector DNA the complementary DNA from step (a) or the DNA fragments which contain chromosomal LyIFN genes from step (b); and
(d) transforming a host cell with the vector from step (c).

25. A method according to claim 24 wherein the interferon is LyIFN-α-1.

26. A method according to claim 24 wherein the interferon is LyIFN-α-2.

27. A DNA in substantially pure form which, on expression, codes for a polypeptide selected from the group consisting of HLycIFN-1′b having the sequence
MET ALA LEU SER PHE SER LEU LEU MET
ALA VAL LEU VAL LEU SER TYR LYS SER
ILE CYS SER LEU GLY CYS ASP LEU PRO
GLN THR HIS SER LEU GLY ASN ARG ARG
ALA LEU ILE LEU LEU ALA GLN MET GLY
ARG ILE PRO PRO PHE SER CYS LEU LYS
ASP ARG HIS ASP PHE GLY PHE PRO GLN
GLU GLU PHE ASP GLY ASN GLN PHE GLN
LYS ALA GLN ALA ILE SER VAL LEU HIS
GLU MET LLE GLN GLN THR PHE ASN LEU
PHE SER THR LYS ASP SER SER ALA THR
TRP GLU GLN SER LEU LEU GLU LYS PHE
SER THR GLU LEU ASN GLN GLN LEU ASN
ASP LEU GLU ALA CYS VAL ILE GLN GLU
VAL GLY VAL GLU GLU GLU THR PRO LEU MET
ASN VAL ASP SER ILE LEU ALA VAL LYS
LYS TYR PHE GLN ARG ILE THR LEU TYR
LEU THR GLU LYS LYS TYR SER PRO CYS
ALA TRP GLU VAL VAL ARG ALA CLU ILE
MET ARG SER PHE SER LEU SER LYS ILE
PHE GLN GLU ARG LEU ARG ARG LYS GLU,
HLycIFN-5₁ having the sequence
MET ALA LEU THR PHE TYR LEU LEU VAL
ALA LEU VAL VAL LEU SER TYR LYS SER
PHE SER SER LEU GLY CYS ASP LEU PRO
GLY THR HIS SER LEU GLY ASN ARG ARG
ALA LEU ILE LEU LEU ALA GLY MET ARG
ARG ILE SER PRO PHE SER CYS LEU LYS
ASP ARG HIS ASP PHE GLU PHE PRO GLN
GLU GLU PHE ASP ASP LYN GLN PHE GLN
LYS ALS GLN ALA ILE SER VAL LEU HIS
GLU MET ILE GLN GLN THR PHE ASN LEU
PHE SER THR LYS ASP SER SER ALA ALA
LEU ASP GLU THR LEU LEU ASP GLU PHE
TYR ILE GLU LEU ASP GLN GLN LEU ASN
ASP LEU GLU SER CYS VAL MET GLN GLU VAL GLY VAL ILE GLU SER PRO LEU MET TYR GLU ASP SER ILE LEU ALA VAL ARG LYS TYR PHE GLN ARG ILE THR LEU TYR LEU THR GLU LYS LYS TYR SER SER CYS ALA TRP GLU VAL VAL ARG ALA GLU ILE MET ARG SER PHE SER LEU SER ILE ASN LEU GLN LYS ARG LEU LYS SER LYS GLU, an interferon having the sequence MET CYS ASP LEU PRO GLN THR HIS SER LEU GLY ASN ARG ARG ALA LEU ILE LEU LEU ALA GLN MET GLY ARG ILE PRO PRO PHE SER CYS LEU LYS ASP ARG HIS ASP PHE GLY PHE PRO GLN GLU GLU PHE ASP GLY ASN GLN PHE GLY LYS ALA GLN ALA ILE SER VAL LEU HIS GLU MET ILE GLN GLN THR PHE ASN LEU PHE SER THR LYS ASP SER SER ALA THR TRP GLU GLN SER LEU LEU GLU LYS PHE SER THR GLU LEU ASN GLN GLN LEU ASN ASP LEU GLU ALA CYS VAL ILE GLN GLU VAL GLY VAL GLU GLU THR PRO LEU MET ASN VAL ASP SER ILE LEU ALA VAL LYS LYS TYR PHE GLN ARG ILE THR LEU TYR LEU THR GLU LYS LYS TYR SER PRO CYS ALA TRP GLU VAL VAL ARG ALA GLU ILE MET ARG SER PHE SER LEU SER LYS ILE PHE GLN GLU ARG LEU ARG ARG LYS GLU, and an interferon having the sequence MET CYS ASP LEU PRO GLN THR HIS SER LEU GLY ASN ARG ARG ALA LEU ILE LEU LEU ALA GLN MET ARG ARG ILE SER PRO PHE SER CYS LEU LYS ASP ARG HIS ASP PHE GLU PHE PRO GLN GLU GLU PHE ASP ASP LYS GLN PHE GLN LYS ALA GLN ALA ILE SER VAL LEU HIS GLU MET ILE GLN GLN THR PHE ASN LEU PHE SER THR LYS ASP SER SER ALA ALA LEU ASP GLU THR LEU LEU ASP GLU PHE TYR ILE GLU LEU ASP GLN GLN LEU ASN ASP LEU GLU SER CYS VAL MET GLN GLU VAL VLY VAL ILE GLU SER PRO LEU MET TYR GLU ASP SER ILE LEU ALA VAL ARG LYS TYR PHE GLN ARG ILE THR LEU TYR LEU THR GLU LYS LYS TYR SER SER CYS ALA TRP GLU VAL VAL ARG ALA GLU ILE MET ARG SER PHE SER LEU SER ILE ASN LEU GLN LYS ARG LEU LYS SER LYS GLU.

* * * * *